US006845204B1

(12) United States Patent
Broeng et al.

(10) Patent No.: US 6,845,204 B1
(45) Date of Patent: Jan. 18, 2005

(54) PHOTONIC BAND GAP FIBER

(75) Inventors: Jes Broeng, Lyngby (DK); Stig Eigil Barkou, Gentofte (DK); Anders Overgaard Bjarklev, Roskilde (DK)

(73) Assignee: Crystal Fibre A/S, Brondby (DK)

(*) Notice: Subject to any disclaimer, the term of this patent is extended or adjusted under 35 U.S.C. 154(b) by 0 days.

(21) Appl. No.: 09/282,303

(22) Filed: Mar. 31, 1999

(30) Foreign Application Priority Data

Jun. 9, 1998 (DK) ........................................ 1998 00779

(51) Int. Cl.[7] .............................................. G02B 6/02
(52) U.S. Cl. ...................... 385/126; 385/123; 385/125
(58) Field of Search .................. 385/126, 123, 385/124, 125, 127, 147; 65/409, 411

(56) References Cited

U.S. PATENT DOCUMENTS

| 5,802,236 | A | * | 9/1998 | DiGiovanni et al. ........ 385/127 |
| 5,907,652 | A | * | 5/1999 | DiGiovanni et al. ........ 385/125 |
| 6,243,522 | B1 | * | 6/2001 | Allan et al. ................ 385/123 |
| 6,301,420 | B1 | * | 10/2001 | Greenaway et al. ........ 385/126 |
| 6,404,966 | B1 | | 6/2002 | Kawanishi et al. ......... 385/125 |
| 6,418,258 | B1 | * | 7/2002 | Wang ........................ 385/125 |

FOREIGN PATENT DOCUMENTS

| EP | 0 810 453 | 3/1997 | |
| EP | 0 905 834 A2 | 3/1999 | |
| WO | WO 99/00685 | 1/1999 | |
| WO | WO 00/49436 | 8/2000 | ............ G02B/6/17 |

OTHER PUBLICATIONS

Jonathan C. Knight, et al.; "Bragg scattering from an obliquely illuminated photonic crystal fiber"; Jan. 20, 1998.
J.C. Knight et al., Optical Materials, "Photonic Crystals as Optical Fibers—Physics and Applications", Jan. 1999.
T.A. Birks, et al., Electronics Letters, "Full 2-D Photonic Bandgaps in Silica/Air Structures", Oct. 26, 1995, vol. 31, No. 22.
J.C. Knight et al., Optics Letters, "All-silica Single-mode Optical Fiber With Photonic Crystal Cladding: Errata", Apr. 1, 1997, vol. 22, No. 7.
Jes Broeng et al, Electromagnetic Optics, "Waveguiding by the Photonic Band Gap Effect", Sep. 1998.
Jes Broeng et al., Optics Communications 156, "Highly Increased Photonic Band Gaps in Silica/Air Structures", Nov. 1998.

(List continued on next page.)

*Primary Examiner*—Frank G. Font
*Assistant Examiner*—Michael P. Mooney
(74) *Attorney, Agent, or Firm*—Morgan & Finnegan, LLP

(57) ABSTRACT

An optical fiber having a periodical cladding structure providing an photonic band gap structure with superior qualities. The periodical structure being one wherein high index areas are defined and wherein these are separated using a number of methods. One such method is the introduction of additional low index elements, another method is providing elongated elements deformed in relation to a circular cross section. Also described is a cladding structure comprising elongated elements of a material having an index of refraction higher than that of the material adjacent thereto. Using this additional material, prior art structures may obtain much better qualities.

54 Claims, 82 Drawing Sheets

OTHER PUBLICATIONS

Stig E. Barkow, Optics Letters, "Silica–air Photonic Crystal Fiber Design That Permits Waveguiding by a True Photonic Bandgap Effect", Jan. 1999, vol. 24, No. 1.

Stig E. Barkou, et al., OFD/IOOC'99, Novel Fiber Structures, "Dispersion Properties of Photonics Bandgap Guilding Fibers", Feb. 26, 1999.

Anders Bjarklev, et al., EPOC'98, 20–24, "Dispersion Properties of Photonic Crystal Fibers", Sep. 1998.

J.C. Knight, et al., Optical Fiber Communication, "Pure Silica Single–mode Fiber With Hexagonal Photonic Crystal Cladding", Feb. 29, 1996.

J.C. Knight, et al., Optics Letters, "All–silica Single–mode Optical Fiber with Photonic Crystal Cladding", Oct. 1, 1996, vol. 21, No. 19.

T.A. Birks et al., Optics Letters, "Endlessly Single–mode Photonic Crystal Fiber", Jul. 1, 1997, vol. 22, No. 13.

J.C. Knight et al., Electronics Letters, "Large Mode Area Photonic Crystal Fiber", Jun. 25, 1998, vol. 34, No. 13.

J.C. Knight et al., Optical Society of America, "Properties of Photonic Crystal Fiber and the Effective Index Model", Mar. 1998, vol. 15, No.3.

Philip St. J. Russell et al, Jpn. J. Appl. Phys, "Silica/Air Photonic Crystal Fibers", 1998, vol. 37.

J.C. Knight et al., Applied Optics, "Bragg Scattering from an Obliquely Illuminated Photonic Crystal Fiber", Jan. 20, 1998,vol. 37, No. 3.

T.A. Birks et al., Photonic Band Gap Materials Kluwer 1996, "2D Photonic Band Gap Structures in Fiber Form", 1996.

P. St. J. Russell et al., ECOC 97 Conference Publication, No. 448, "Photonic Crystal Fibers", Sep. 1997.

T.A. Birks et al., OFC/IOOC'99, Novel Fiber Structures, "The Analogy Between Photonic Crystal Fibers and Step Index Fibers", Feb. 1999.

T.A. Birks et al., OFC/IOOC'99, Novel Fiber Structures, "Single Material Fibers for Dispersion Compensation", Feb. 1999.

Robert S. Windeler et al., OFC/IOOC'99, Novel Fiber Structures, "Silica–air Microstructured Fibers: Properties and Applications", Feb. 1999.

Tanya M. Monro et al., OFC/IOOC'99, Novel Fiber Structures, "Efficient Modelling of Holey Fibers", Feb. 1999.

A. Ferrando et al., Optical Letters, "Full vector Analysis of a Realistic Photonic Crystal Fiber", Mar. 1999, vol. 24, No. 5.

A. Ferrando et al., Electronics letters, "Designing a Photonic Crystal Fiber With Flattened Chromatic Dispersion", Feb. 1999, vol. 35, No. 4.

M.J. Gander et al., Electronics Letters, "Experimental Measurement of Group Velocity Dispersion in Photonic Crystal Fiber", Jan. 7, 1999, vol. 35, No. 1.

R.P. Espindola et al., Electronics Letters, "External Refractive Index Insensitive Air–clad Long Period Fiber Grating", Feb. 18, 1999, vol. 35, No. 4.

Jes Broeng et al. , Center for Communications, Optics, and Materials (COM), "Polarizaton Properties of Photonic Bandgap Fibers".

Jes Broeng et al. , Optics Letters, "Analysis of Air–Guiding Photonic Bandgap Fibers", Jan. 15, 2000, vol. 25, No. 2.

Tanya M. Monro et al, Optics Letters, "Holey Fibers With Random Cladding Distributions", Feb. 15, 2000, vol. 25, No. 4.

D. Mogilevtsev et al., "Group–velocity Dispersion in Photonic Crystal Fibers", Optical Letters, Nov. 1, 1998.

J.C. Knight et al., "Photonic Band Gap Guidance in Optical Fibers", Science, Nov. 20, 1998.

Broeng et al., Polarization Properties of Photnic Bandgap Fibres.

Bjarklev, Microstructured Fibres, May 23–28, 1999.

Russell et al., Microscopic Glass Fibre Crystals.

Rosenberg et al., Out–of–plane two–dimensional photonic band structure effects observed in the visible spectrum, Sep. 9, 1997.

Cassagne et al., Hexagonal photonic–band–gap structures, Oct. 19, 1995.

Cassagne et al., Optical properties of two–dimensional photonic crystals with graphite structure, Nov. 13, 1996.

Gadot et al., Experimental demosntration of complete photonic band gap in graphite structure, Jul. 24, 1997.

Barra et al., Existence of two–dimensional absolute photonic band gaps in the visible, Dec. 6, 1994.

* cited by examiner

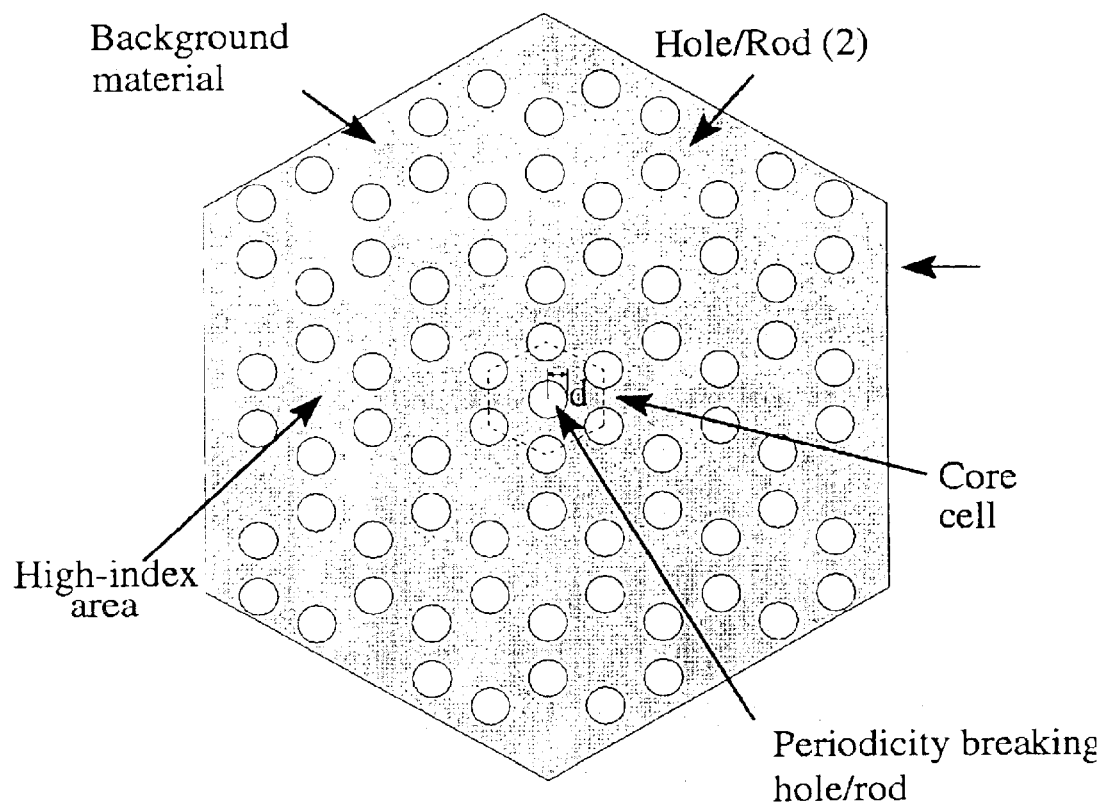

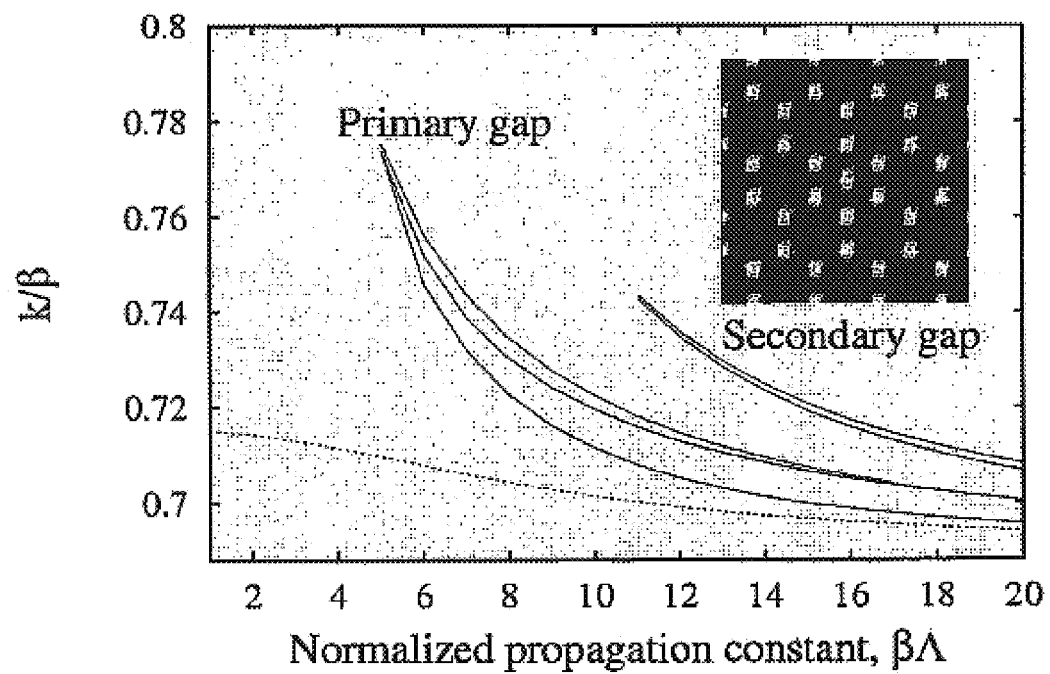

Triangular lattice

Triangular lattice

Honeycomb lattice

Honeycomb lattice

Kagomé lattice

Kagomé lattice

PHOTONIC BAND GAP FIBER

FIELD OF INVENTION

The present invention relates to a novel group of cladding designs, especially for use in optical fibres, wherein a larger photonic band gap may be provided while retaining the stability and physical properties of the fibre.

BACKGROUND OF THE INVENTION

Optical fibres and integrated optical waveguides are today applied in a wide range of applications within areas such as optical communications, sensor technology, spectroscopy, and medicine. These waveguides normally operate by guiding the electromagnetic field (the light or the photons) through a physical effect, which is known as total internal reflection. By using this fundamental effect, the propagation (or loss) of optical power in directions perpendicular to the waveguide axis is reduced.

In order to obtain total internal reflection in these waveguides, which are often fabricated from dielectric materials (in optical fibres) or semiconductors (in integrated optics), it is necessary to use a higher refractive index of the core compared to the refractive index of the surrounding cladding.

Today the preferred signal transmission medium over long and medium distances is the optical fibre, and total internal reflection is, consequently, a physical property, which has been known and used in technological development for decades. During the past ten years, however, the development within the area of new materials has opened up the possibilities of localisation of light or control of electromagnetic fields in cavities or waveguides by applying a completely new physical property—the so-called photonic band gap (PBG) effect.

The PBG effect may be introduced by providing a spatially periodic lattice structure, in which the lattice dimensions and applied materials are chosen in such a way that electromagnetic field propagation is inhibited in certain frequency intervals and in certain directions. These PBG materials have been described in one-, two-, and three-dimensional cases in the scientific literature and in several patents (see for instance U.S. Pat. No. 5,356,215, U.S. Pat. No. 5,335,240, U.S. Pat. No. 5,440,421, U.S. Pat. No. 5,600,483, U.S. Pat. No. 5,172,267, U.S. Pat. No. 5,559,825).

A specific class of components, which makes use of such periodic dielectric structures, are the optical fibres (or waveguides), in which the periodic variation appears in directions perpendicular to the waveguide axes, whereas the structures are invariant along the waveguide axes.

Within recent years, especially researchers from University of Bath, UK, (see e.g. Birks et al., Electronics Letters, Vol.31 (22), p.1941, October 1995) have presented such fibres realised by having a silica core surrounded by thin, parallel, and air-filled voids in a silica-background material, and organising the air-filled voids in a triangular structure in the cladding region of the fibres. These optical fibres have demonstrated interesting propagation properties compared to standard optical fibres utilising total internal reflection.

It may be a problem or disadvantage of this particular realisation of optical fibres with periodic dielectric cladding regions that careful stacking of either hexagonal glass tubes (with central holes) or direct stacking of thin circular tubes is required. These tubes have been arranged in a triangular structure in a perform, where after the perform is drawn into an optical fibre. Although these fibres according to the reports in the international literature show quite specific and new optical properties, one of the problems has been that the core of the fibre could only be formed by introduction of a glass rod without a central hole.

It is a further disadvantage that even these new fibres have core areas with higher refractive index than the average refractive index of the surrounding media, and their waveguiding effect may, consequently, also be described by conventional total internal reflection. This naturally has the consequence that for applications within areas such as optical sensors, where it may be of specific interest to be able to localise optical fields in and around areas with low refractive indices (e.g., around air-filled channels), the presently known fibres may not be used directly.

It is a still further disadvantage that, due to the triangular cladding structure, the PBG of the structures described by Birks et al. are not optimised for guiding electromagnetic radiation using the PBG effect.

U.S. Pat. No. 5,802,236 discloses micro-fabricated optical fibres having a core and a cladding region, wherein the cladding region comprises a multiplicity of spaced apart cladding features that are elongated in the direction of the fibre. The effective refractive index of the cladding region is less than the effective refractive index of the core region. Furthermore, the elongated features in the cladding are arranged in a non-periodic structure.

It is a disadvantage of the micro-fabricated optical fibre disclosed in U.S. Pat. No. 5,802,236 that due to the high-index core region the waveguiding characteristics are based on traditional total internal reflection of the electromagnetic radiation guided in the core region.

WO 99/00685 discloses a large core photonic crystal fibre (PCF) comprising a cladding having a triangular periodic structure. The core region may be either a high-index or low-index region having a diameter of at least 50 $\mu$m. In a preferred embodiment the core region may be as large as 50 $\mu$m in diameter. With such a diameter, the fibre is capable of transmitting high powers, whilst maintaining single-mode operation.

It is a disadvantage that the triangular cladding structure disclosed in WO 99/00685 will not, using realistic manufacturing parameters, provide a sufficient PBG so as to effectively confine visible or NIR electromagnetic radiation within the core region of the fibre.

It is a further disadvantage of the structure disclosed in WO 99/00685 that in order to obtain a sufficient PBG, the dimensions of the features forming the triangular periodic structure must be very large. Such large features, e.g. air-filled holes, make the structure difficult to manufacture and inconvenient for practical applications.

It is an object of the present invention to provide a new class of optical waveguides, in which waveguiding along one or more core regions is obtained through the application of the PBG effect.

It is a further object of the present invention to provide a two-dimensional lattice structure capable of providing complete PBG's for realistic manufacturing parameters.

It is a still further object of the present invention to provide low-index core PBG waveguiding structures.

It is a still further object of the present invention to provide a PBG structure, which is easy to manufacture.

SUMMARY OF THE INVENTION

The present inventors have realised that the photonic band gap of an optical fibre, which cladding structure is typically formed as two-dimensionally periodic low index areas within a given material, may be defined as a number of high index areas separated by the low index areas forming the periodic structure. The performance of the optical band gap may be increased, if these high index areas are "separated" from each other. These areas couple via areas ("bridges") between the low index areas, and this "separation" may be obtained in a number of areas.

In the following, naturally a periodic structure will be defined by a primitive unit cell, as is the most widely used manner of simplifying the analysis of such a structure. However, the actual shape and contents of this cell may vary in relation to a structure more intuitively correct in analysing the high index areas. To that effect, we will make use of a polygon, which will be defined by low index areas but will normally define the position of a high index area.

It should be noted that many sizes of unit calls will exist but only one of a primitive unit cell which is defined as a unit cell which has the smallest area possible and which, only by translation, can generate the structure. Naturally, a given periodic structure may have a plurality of primitive unit cells.

In the following, the structure is defined by a unit cell, which will be identical to a primitive unit cell.

In a first aspect, the invention relates to a separation where additional low index areas are provided in addition to those elements normally defining the periodic structure.

Thus, in this first aspect, the invention relates to an optical fibre with a waveguide structure having a longitudinal direction, said optical fibre having:
  a core region extending along the longitudinal direction,
  a cladding region extending along the longitudinal direction, said cladding legion comprising an at least substantially two-dimensionally periodic structure comprising primary, alongated elements each having a centre axis extending in the longitudinal direction of the waveguide, the primary elements having a refractive index being lower than a refractive index of any material adjacent to the primary elements,
the periodic structure being, in a cross-section perpendicular to the longitudinal direction, defined by at least one unit cell, wherein, for each unit cell:
  a first circle is defined as the largest circular area possible having a centre not positioned outside the unit cell and not enclosing any part of any primary elements, and
  one or more further elongated elements are provided each of which
    has an area not exceeding $\frac{1}{6}$ of the area of that primary element having its centre within the unit cell and having the largest area,
    has a refractive index being lower than that of any material adjacent thereto,
    has a centre not positioned outside the unit cell, and
    does not cover the centre of the first circle.

In the present context, "substantially two-dimensionally periodic" will mean that it is desired to have an optimal periodicity, but that the manners of production will often alter this. In the prior art it is seen that when circular air holes (low index areas) are introduced into a preform of glass and subsequently drawn, the holes will obtain a not-circular shape which is a sign of this substantial periodicity.

Also, in the present context, the refractive index of the primary elements has to be lower than that of any material adjacent thereto, meaning that this actual change of index is that providing the periodic structure. This step is not dependent on changes of refractive indices outside the immediate area around the circumference of the primary elements. Naturally, this step may be different for all primary elements, but normally the material adjacent to the primary elements is the same throughout the structure—and so is that of the primary elements, whereby the step will be the same at all circumferences around the primary elements.

In this situation, the first circle will define a so-called high index area, even when the actual refractive index is that of all of the fibre (except for the primary elements).

In this situation, further low index areas may be provided. When positioned correctly, these will separate the high index areas in that the coupling via the bridges is reduced due to the bridges being narrowed in effective area or width even when increased in number.

The effect of the further elements will, naturally, depend on the size thereof, it the size is increased beyond that of $\frac{1}{6}$ of that of the primary elements, they will have an effect of actually changing the periodicity and call shape of the overall structure. However, it may be preferred that the one or more further elements each has an area not exceeding $\frac{1}{8}$, such as an area not exceeding $\frac{1}{10}$, such as an area not exceeding $\frac{1}{12}$, such as an area not exceeding $\frac{1}{15}$, such as an area not exceeding $\frac{1}{30}$ of the area of that primary element having its centre not positioned outside the unit cell and having the largest area.

Instead of or in addition to the narrowing of the "bridges" in the structure, two high index areas may be separated by reducing the sizes thereof. The further elements may be used for that by positioning these in a specific manner: for the unit cell, a second circle is defined being the largest possible circle having its centre not positioned outside the unit cell, and wherein the second circle not comprising any parts of the primary or further elongated elements, and wherein the area of the second circle is smaller than that of the first circle. In that manner, the further elements act to reduce the size of the high index area and thereby to separate two adjacent high index areas.

Preferably, the area of the second circle is 90% or less, such as 80% or less, such as 70% or less, such than 60% or less, such as 60% or less, such as 40%, such as 30% or less or less than that of the first circle.

Even though the positioning of the further elements may easily be so that the centres of the first and second circles do not coincide, this would normally alter the symmetry of the structure and, thus, not be desired. Consequently, preferably the centre of first circle at least substantially coincides with the centre of the second circle.

The above-mentioned polygon, having three or more sides, is defined as having its vertices at the centres of those primary elements, parts of which are within a distance of 1.5 or less, such as 1.2 or less, such as 1.1 or less times the radius of the first circle from the centre of the first circle.

Preferably, due to the periodicity of the structure, the polygon is a regular polygon. This polygon may be a triangular, rectangular, quadratic, or hexagonal polygon.

Another manner of effecting the separation of the high index areas is to provide more low index areas than those used in the prior art.

Thus, in a second aspect, the invention relates to an optical fibre with a waveguide structure having a longitudinal direction, said optical fibre having:
  a core region extending along the longitudinal direction,
  a cladding region extending along the longitudinal direction, said cladding region comprising an at least substantiality two-dimensionally periodic structure comprising primary, elongated elements each having a centre axis extending in the longitudinal direction of the waveguide, the primary elements having a refractive index being lower than a refractive index of any material adjacent to the elongated elements, the periodic structure being defined, in a cross-section perpendicular to the longitudinal direction, by a unit cell, wherein the sum of all areas of elongated elements, which areas are comprised within the unit cell, is larger than 1.2 times the area of that primary element having its centre axis not positioned outside the unit cell and having the largest area.

As mentioned above, these areas may be used ether for reducing the sizes of the high index areas or for reducing the coupling there between via the bridges between the primary elements of the periodic structure. Preferably, the size of the high index areas is as large as possible, so the mostly preferred manner is to narrow the bridges by introducing additional low index areas between two high index areas.

Preferably, the sum of all areas of elongated elements comprised within the unit cell is larger than 1.3, such as larger than 1.4, such as larger than 1.5, such as larger than 1.75, such as larger than 2, such as larger than 2.5 times the area of that primary element having its centre axis not positioned outside the unit cell and having the largest area.

An additional manner of separating the high index areas is to increase the index thereof. Thus, preferably the periodic structure comprises secondary elongated elements having a refractive index being larger than that of any material adjacant thereto and to any material being adjacent to a primary element.

In that manner, for a unit cell, the sum of all areas of secondary elements within the unit cell is preferably larger than 1, such as larger than 1.1, such as larger than 1.2, such as larger than 1.3, such as larger than 1.4, such as larger than 1.5, such as larger than 1.75, such as larger than 2, such as larger than 2.5 tines the area of a secondary element having its centre axis not positioned outside the unit cell and having the largest area.

Also, for a unit cell, the sum of all areas of secondary elements within the unit cell is preferably larger than 0.05, such as larger than 0.1, such as larger than 0.5, such as larger than 1., such as larger than 2, such as larger than 5, such as larger than 8, such as larger than 10, such as larger than 15, such as larger than 20, such as larger than 25 times the area of the primary element having its centre axis not positioned outside the unit cell; and having the largest area.

In addition to the separation of the high index areas, another manner of increasing the performance of the band gap structure is to provide more circular cells or polygons. The inventors have realised that the optimum structure is ore which "looks the same for light coming from all angles" in the cross sectional plane perpendicular to the longitudinal axis of the fibre.

Therefore, in a third aspect, the invention relates to an optical fibre with a waveguide structure having a longitudinal direction, said optical fibre having:
a core region extending along the longitudinal direction,
a cladding region extending along the longitudinal direction, said cladding region comprising an at least substantially two-dimensionally periodic structure comprising primary, elongated elements each having a centre axis extending in the longitudinal direction of the waveguide, the primary elements having a refractive index being lower than a refractive index of any material adjacent to the primary elements,
the periodic structure being, in a cross-section perpendicular to the longitudinal direction, defined by a unit cell, and where a polygon is defined:
having centres of primary elements in its vertices,
not enclosing any centres of other primary elements than those having their centres at the vertices of the polygon, and
having an area less than or equal to that of the unit cell, wherein a first circle is defined as the smallest circle possible having its centre positioned within the polygon, and which comprises the vertices of the polygon,
and wherein the area of the circle divided by the area of the polygon is less than 2.4, such as less than 1.5, such as less than 1.2.

For the known triangular structures, is relationship between the are as is 2.42, and for the preferred hexagonal 1.21.

In this context, the circle comprises the vertices of the polygon will mean that these vertices are within the circle or on the periphery thereof. When the polygon is a regular polygon, the first circle is that circumscribing the polygon.

Typically, the polygon has four or more sides, and it nay be quadratic or a hexagonal polygon.

Yet another manner of quantifying the separation of the high index areas will relate to the interaction of the refractive indices and the distance between the high index areas and the sizes of the bridges.

Therefore, in a fourth aspect, the invention relates to an optical fibre with a waveguide structure having a longitudinal direction, said optical fibre having:
a core region extending along the longitudinal direction,
a cladding region extending along the longitudinal direction, said cladding region comprising an at least substantially two-dimensionally periodic structure comprising primary, elongated elements each having a centre axis extending in the longitudinal direction of the waveguide, the primary elements having a refractive index being lower than a refractive index of any material adjacent to the primary elements,
the periodic structure being, in a cross-section perpendicular to the longitudinal direction, defined by a unit cell, wherein, for each unit cell:

$$n_d \Lambda_2 > n_{ud} \Lambda_1 (\sqrt{3})$$

where
$n_d$ is the largest index of refraction within a first circle which is defined as a largest circle possible having a centre not positioned outside the unit cell and not enclosing any part of any primary element,
$n_{ud}$ is a largest index of refraction not positioned outside the unit cell but positioned outside any of the first circles of the unit cells,
$\Lambda_1$ is a smallest distance between centre axes of two primary elements within the periodic structure,
$\Lambda_2$ is a smallest distance between the centres of two adjacent first circles.

In this formula it is seen that the separation of high index areas may be effected by narrowing the bridges, which may be obtained by providing more low index areas or providing a novel structure having a smaller distance by nature. Alternatively or in addition, the separation may be effected by physically separating the high index areas, such as is seen when going from the prior art triangular structure to the honeycomb structure. Also, an effective "separation" is seen when the high index area is, in fact, provided with a refractive index higher than that of its surroundings.

It should be understood that, naturally, the periodic structure only needs be that structure sufficient to confine light by the PBG effect. This distance may be 2–20 periods of the periodic structure—depending on the actual structure thereof. Outside that part of the fibre, any structure or material may be provided.

In order to obtain an even better performance, it is preferred that, for each unit cell: $n_d \Lambda_2 > 2 n_{ud} \Lambda_1$, such as $n_d \Lambda_2 > 3 n_{ud} \Lambda_1$, such as $n_d \Lambda_2 > 4 n_{ud}\Lambda_1$, such as $n_d \Lambda_2 > 6 n_{nd}\Lambda_1$, such as $n_d \Lambda_2 > 10 n_{ud} \Lambda_1$.

Naturally, the more different materials in the fibre, the larger the complexity thereof. Thus, it may be desired that, in each unit cell, $n_d$ is at least substantially identical to $n_{ud}$. However, the maximum index difference obtainable using materials standard in fibre manufacture may not be sufficient. In that situation, it may be desired that, in each unit cell, $n_d > n_{ud}$.

The present fibre may be made of any suitable material, and $n_d$ and $n_{ud}$ may consequently be chosen as a material having a refractive index in the interval from that of silica over polymers to semiconductors, that is, 1–10. A material standard in fibre manufacture is silica, whereby $n_d$ and $n_{ud}$ would normally be chosen in the interval 1.40–1.60—naturally taking into account the relationship between $n_d$ and $n_{ud}$.

As described above, it has been found that the introduction of additional low index areas will further separate the high index areas and provide a fibre with an improved performance. Thus, preferably, the unit cell comprises further elongated elements each having a centre axis extending in the longitudinal direction of the waveguide, the cross-sectional area of each of the further elements being less than ⅙ of a cross-sectional area of that primary element, having its centre within the unit cell, having the largest cross-sectional area.

In that situation, it is advantageous that $$n_d \Lambda_2 > (\sqrt{3}) n_{ud} \Lambda_3$$

where $n_d$ is the largest index of refraction within a first circle which is defined as a largest circle possible having a centre not positioned outside the unit cell and not enclosing any part of any primary element, $n_{ud}$ is a largest index of refraction not positioned outside the unit cell but outside any of the first, circles of the unit cells, $\Lambda_3$ is a smallest distance between centre axes of two primary or further elements within the periodic structure, $\Lambda_2$ is a smallest distance between the centres of two adjacent first circles.

Again, the better a separation, the better a performance, which means that it is preferred that, for each unit cell: $n_d \Lambda_2 > 2 n_{ud} \Lambda_3$, such as $n_d \Lambda_2 > 3 n_{ud} \Lambda_1$, such as $n_d \Lambda_2 > 4 n_{ud}\Lambda_3$, such as $n_d \Lambda_2 > 8 n_{ud}\Lambda_3$, such as $n_d\Lambda_2 > 10 n_{ud} \Lambda_3$.

Yet another manner of characterising the invention is one relating to the number of vertices or sides of the largest-area-polygons in the structure. In preferred fibres, these polygons are regular, whereby this number of sides or vertices will relate to the area thereof—and typically of an area or spacing of the high index areas.

Thus, in a fifth aspect, the invention relates to an optical fibre with a waveguide structure having a longitudinal direction, said optical fibre having:

a core region extending along the longitudinal direction, a cladding region extending along the longitudinal direction, said cladding region comprising an at least substantially two-dimensionally periodic structure comprising primary, elongated elements each having a centre axis extending in the longitudinal direction of the waveguide, the primary elements having a refractive index being lower than a refractive index of any material adjacent to the primary elements, the periodic structure being, in a cross-section perpendicular to the longitudinal direction, defined by at least one unit cell, wherein, for each unit cell, a first circle is defined as the largest circular area possible having a centre not positioned outside the unit cell and not enclosing any part of any primary elements, wherein more than 3 first primary elements exist, parts of which exist within a distance of 1.2 or less times the radius of the first circle from the centre of the first circle.

If the polygon is regular, the primary elements defining the polygon will be positioned just outside the perimeter of the circle. However, production methods will introduce uncertainties and displacements, whereby the distance between the circle and the elements may be larger or smaller.

As mentioned above, both the circularity and the separation may be increased, if the polygon is provided with more vertices than 3. Consequently, preferably more than 4, such as more than 5, such as more than 6, such as more than 8, such as more than 10 first primary elements exist, parts of which exist within a distance of 1.2 or less times the radius of the first circle from the centre of the first circle.

Also, if the production methods provide a reasonable control over displacements etc. in the manufacturing process, preferably the parts of the first primary elements exist within a distance of 1.1 or less times the radius of the first circle from the centre of the first circle.

Also, depending on the structure and manufacturing method, the centres of the primary elements may exist within the distance of 1.2 or less or 1.1 or less than the radius.

One manner of providing a certain number of first primary elements around a high index area will be to provide a polygon having the same number of vertices.

Another manner is one wherein certain first primary elements defining the vertices and others positioned along the sides thereof. In that situation, the first primary elements typically define a polygon having 3–6 sides and having centres of first primary elements in its vertices, each of the first primary elements not having centres in the vertices being positioned with its centre axis no further from a side of the polygon than ⅕, such as ⅒, such as ⅕ of a length of that side.

Another manner of separating two high index areas will be to, instead of or in addition to providing tow index areas in addition to those defining the basic periodic structure, provide the primary elements defining the basic periodic structure with a cross sectional shape increasing the separation between the high index areas.

Consequently, in a sixth aspect, the invention relates to an optical fibre with a waveguide structure having a longitudinal direction, said optical fibre having:

a core region extending along the longitudinal direction, a cladding region extending along the longitudinal direction, said cladding region comprising an at least substantially two-dimensionally periodic structure comprising primary, elongated elements each having a centre axis extending in the longitudinal direction of the waveguide, each primary element having a refractive index being lower than a refractive index of any material adjacent to the primary element, the periodic structure being, in a cross-section perpendicular to the longitudinal direction, defined by a unit cell, and where, for each unit cell, one or more polygons are defined as:

a first polygon is defined as having its vertices at centres of first primary elements selected by:
defining a first circle as the largest circular area possible, having a centre not positioned outside the unit cell and not enclosing any part of any primary elements,
selecting the first primary elements as those having pats not positioned further away from the centre of the first circle than 1.2 times the radius of the first circle,
for each area, if any of the unit cell, which area is not comprised within a first polygon, an additional polygon is defined as having its vertices at centres of additional primary elements selected by:
defining an additional circle as the largest circular area possible having a centre not positioned outside the area and not enclosing any part of any primary elements,
selecting the additional primary elements as those having their centres not positioned further away from the centre of the additional circle than 1.2 times the radius of the additional circle,
the periodic structure comprising deviating primary elements having a shape deviating from a circular shape and having extending parts defined as those parts of the shape of the deviating primary element extending outside a circle having the same area as that of the deviating primary element and having its centre at a centre of the deviating primary element, each extending part extending toward one of those primary elements which together with which the deviating primary element defines a side of a polygon in the periodic structure,
each extending part extending toward a primary element and having an area being larger than 3%, such as larger than 5%, such as larger than 10%, such as larger than 15%, such as larger than 20%, such as larger than 25% of the area of the circle.

In the present context, the centre of the deviating primary element will be a symmetrical centre of a centre of weight of the cross section thereof.

In the prior art, primary elements having a cross sectional shape deviating from that of a circle are known. However, those shapes have been inadvertent due to the methods of manufacture and often have a shape and direction detrimental to the periodicity of the structure and to the size of the band gap. The inventors have found that providing such shapes in the correct manner may increase the separation of the high index areas while maintaining the periodicity of the structure—in much the same manner as when providing additional low index areas along the circumference of the polygon.

Preferably, at least one extending part has an axis of symmetry at least substantially coinciding with a line intersecting the centre of the circle and the centre of a primary element with which the deviating primary element defines a side. In this manner, the extending part will point along the direction of a side of a polygon. The symmetry of the periodic structure may then especially be maintained, if all extending parts point in such directions.

Normally, such an axis of symmetry would be desirable, as the lack of a such will mean that the symmetry of the structure has been reduced. However, manufacturing methods may render is slightly difficult to find this axis due to deformation of the extending part from the initially desired shape.

Intuitively, one would understand that the larger the portion of a polygon surrounding a high index area which is covered by low index areas, the better a separation of the high index areas. Thus, it is preferred that at least one extending part extends a distance of at least 5%, such as at least 10%, such as at least 15%, such as at least 20%, such as at least 30%, such as at least 50%, such as at least 75%, such as at least 100% of the radius of the circle and in a direction away from the centre of the circle.

Again, a first circle may be defined as the smallest possible circle having its contra positioned within the first polygon, and which comprises the vertices of the first polygon, that is, the vertices are positioned within or on the boundary of the first circle.

Preferably, the first polygon has four or more sides, and roost preferably, the first polygon is a hexagonal, regular polygon.

According to the invention, an especially preferred structure should be one that provides a good separation between the high index areas and is relatively circular. One such shape is a rectangular shape which also has the advantage that it may itself fully define a periodic structure—or it may take part thereof.

Thus, in a seventh aspect, the invention relates to an optical fibre with a waveguide structure having a longitudinal direction, said optical fibre having:
a core region extending along the longitudinal direction,
a cladding region extending along the longitudinal direction, said cladding region comprising an at least substantially two-dimensionally periodic structure comprising primary, elongated elements each having a centre axis extending in the longitudinal direction of the waveguide, the primary elements each having a refractive index being lower than a refractive index of any material adjacent to the primary element,
the periodic structure being, in a cross-section perpendicular to the longitudinal direction, defined by a unit cell, and wherein a polygon is defined:
having centres of primary elements in its vertices,
not enclosing any centres of other primary elements than those having their centres at the vertices of the polygon, and
having an area less than or equal to that of the unit cell, the polygon being a regular, hexagonal polygon.

In order to separate the high index areas even better, one or more further elongated elements are preferably provided each of which
has an area not exceeding ⅙ of the area of that primary element having its centre within the unit cell and having the largest area,
has a refractive index being lower than that of any material adjacent thereto,
wherein symmetry may be preserved, if:
further elements of two polygons sharing a common side are positioned symmetrically around a centre of the common side, and
further elements of two polygons sharing a single primary element are positioned symmetrically around a centre of the single primary element.

As mentioned above, if the further elements are provided with an area larger than ⅙ of the area of that primary element having its centre within the unit cell (or at least not outside) and having the largest area, these further elements would reach a size where they would take part in the overall defining of the structure of the periodic structure—and thus be primary elements.

Preferably, the one or more further elongated elements each has an area not exceeding ⅛, such as an area not exceeding 1/10, such as an area not exceeding 1/12, such as an area not exceeding ⅕ of the area of that primary element having its centre not positioned outside the unit cell and having the largest area.

One specifically preferred embodiment is wherein, in the periodic structure, regular hexagonal polygons exist, all sides of which are shared with another regular hexagonal polygon. This corresponds to a honeycomb structure defined solely by regular hexagonals.

Another preferred embodiment is one wherein the structure is defined by the regular hexagonal polygon and a regular triangle having a side length corresponding to that of the regular hexagonal polygon, and wherein hexagonal polygons exist, each side of which is shared with a triangle. This is the so-called Kagomé structure.

In this second embodiment, the advantages of the hexagonal structure are maintained, and a further spacing of the high index areas defined in the hexagonals is provided via the triangles.

As mentioned above, another manner of obtaining an effective separation of the high index areas would be to increase the refractive index of such areas. Thus, in a number of the above aspects, it is preferred that the periodic structure further comprises one or more secondary elongated elements having a refractive index higher than fiat of any material adjacent thereto or adjacent to any primary elements, the secondary elements each has a centre axis extending in the longitudinal direction of the fibre.

Again, normally the material adjacent to the secondary elements would be the same as that adjacent to the primary elements.

In order to maintain the periodicity, it is desired that, for each unit cell, a secondary element is provided having its centre axis within the first circle, and more preferably that the secondary element is positioned so as to cover the centre of the first circle. Most preferably, the secondary element is positioned so as to have its centre axis at least substantially coincide with the centre of the first circle.

In an eighth aspect, the invention relates to an optical fibre with a waveguide structure having a longitudinal direction, said optical fibre having:
   a core region extending along the longitudinal direction,
   a cladding region extending along the longitudinal direction, said cladding region comprising an at least substantially two-dimensionally periodic structure comprising primary, elongated elements each having a centre axis extending in the longitudinal direction of the waveguide, the primary elements each having a refractive index being lower than a refractive index of any material adjacent to the primary element,
the periodic structure further comprising secondary, elongated elements each having a refractive index being larger than that of any material adjacent thereto and any material adjacent to a primary elements each secondary element having a centre axis extending in the longitudinal direction of the fibre.

Normally, the periodic structure is, in a cross-section perpendicular to the longitudinal direction, defined by at least one unit cell, where, for each unit cell, a first circle is defined as the largest circular area possible having a centre not positioned outside the unit cell and not enclosing any part of any primary elements, where a secondary element is preferably provided having its centre axis within the first circle.

As mentioned above, desirably the secondary element is provided so as to cover the centre of the first circle, and preferably, the secondary element is provided so as to have its centre axis at least substantially coincide with the centre of the first circle.

Also, the polygon may be defined as follows: a plurality of first primary elements exist, parts of which exist within a distance of 1.2 or less times the radius of the first circle from the centre of the first circle, a polygon being defined as having its vertices at the centres of the plurality of first primary elements. Preferably, the polygon is a regular, hexagonal polygon.

This hexagonal polygon may be used in either the honeycomb structure or the Kagomé structure.

All the above aspects of the invention relate to specific cladding structures and comprise no limitations what so ever on the core region.

In fact, the invention should be taken as one relating to these specific cladding regions for use in any type of optical fibre in combination with one or more cores or core regions of any type.

Normally, in relation to band gap structures, the core is taken as an area of the structure, where the periodicity of the band gap structure is broken. The band gap structure is designed so as to make light transmission impossible, and an altering of the periodicity will, consequently, make light transmission possible—but only in the core region.

A number of different manners exist for defining the core. One manner is to replace one or more elements of the periodic structure with other elements with different refractive indices, cross sectional areas or shapes. Another manner is to have the core also have a periodic structure where only one or more elements are not present.

Preferably, the core region would comprise a first additional elongated element extending in the longitudinal direction of the fibre.

An especially preferred first additional element is constituted by air or gas and being defined as a void in the material of the fibre, such as a void having a cross sectional area in the cross section being at least one, such as a, least 2, such as at least 3, such as at least 4, such as at least 6, such as at least 6, such as at least 7, such as at least 8, such as at least 9, such as at least 10 times the cross sectional area of the unit cell.

In that situation, the light may propagate in and/or around air, which provides a number of advantages both as to transmission loss, dispersion, and when used e.g. as a sensor where gas or liquid may be provided within the void to obtain optimum overlap between the light and the gas or liquid.

In a number of different applications, the additional element or any material adjacent thereto may desirably comprise a dopant or a material showing higher order optical effects.

For communication purposes, higher order effects may be used for e.g. silicon communication.

For applications for fibre lasers or fibre amplifiers, the dopant may be e.g. a rare earth dopant adapted to receive pump radiation and amplify radiation travelling in the core region.

Alternatively, the dopant may be a light sensitive dopant, such as Germanium or Deuterium. In that situation, the dopant may be use for e.g. optically writing a grating in the fibre or core region.

For sensor applications, the dopant may be a material response to a characteristic of a gas or liquid, which response may be detected optically by light traveling in the core region.

In a number of applications, it is preferred that the core region comprises a second additional elongated element, the first and second additional elements being positioned at a distance where light travelling in one additional element is able to couple to the other additional element.

In one application one elongated element may be a void holding a liquid or gas which may be too turbid for light to travel through. In that situation, the light may travel in the other element while still coupling with the liquid or gas due to the distance between the elements.

In this situation, one may choose to have the liquid or gas travel only in one or both additional elements—or even in all elongated voids, such as voids of the cladding structure.

Also, by providing two elements between which the light may couple, a number of optical devices may be provided, such as optical fibre couplers. The optical coupling between core elements or core regions may be designed so as to have a predetermined coupling at one or more defined wavelengths, which further makes a number of optical elements possible.

As indicated above, specific advantages will be obtained also when the second additional element is a void.

In fact, due to the periodic structure of the present fibre, the fibre may easily be made to comprise a plurality of core regions.

These core regions may be provided sufficiently close for light travelling in one core region being able to couple to one or more core regions.

Alternatively, the core regions may be positioned spaced apart in order to provide a number of separate waveguides in a single fibre. In fact, the waveguides may be spaced sufficiently apart to the band gap structures surrounding each thereof to be different and e.g. be optimised for different wavelengths or wavelength regimes.

Preferably, the core regions are positioned symmetrically within the periodic structure, a period of the core regions being larger than a period of the periodic structure.

Naturally, a fibre of the present type may be used for a number of applications where fibres are already used today.

Thus, in a ninth aspect, the invention relates to a sensor for sensing or detecting at least one characteristic of a liquid or gas, the sensor comprising:

a length of the optical fibre according to the invention, wherein the core region comprises at least a first additional element, the first element being a void extending along the longitudinal direction of the fibre, means for providing the liquid or gas into the void of the core region, means for introducing light into the core region, the light being adapted to interact with the gas or liquid in a manner so that the characteristic of the liquid or gas may be determined, means for detecting light emitted from the fibre and for determining the characteristic of the liquid or gas.

At present, the characteristic may be absorption, absorbance, the presence of a specific agent or material in the gas or liquid, such as for use as a smoke detector, or any other characteristic sensed by an optical sensing method.

If the gas or liquid has a sufficiently low absorption at the wavelength of the light, the introducing means may be adapted to introduce the light into the first additional element. In that situation, an optimum overlap exists between the light and the liquid or gas.

Alternatively, the core region may comprise a second, elongated element extending in the longitudinal direction of the fibre, where the first and second additional elements are positioned at a distance where light travelling in one additional element is able to couple to the other additional element, and wherein the introducing means is adapted to introduce the light into the second additional element. In that situation, the sensing takes place via the light extending from the second to the first element.

In another type of sensor, the characteristic may not be sensed directly by light. In that situation, it may be desired to expose a suitable material to the characteristic, where the response of that material may be sensed optically. Thus, in this situation, at least part of an inner surface of the first additional element may comprise a layer of a material being adapted to alter in response to the characteristic of the gas or liquid, and wherein the introducing means is adapted to introduce light of a wavelength responsive to the altering of the material.

Naturally, the sensor may additionally comprise means for providing the gas or liquid in the fibre, such as for repeatedly providing gas or liquid therein, such as a gas pump of the sensor is used as a smoke detector.

In a tenth aspect, the inventor relates to a fibre amplifier for amplifying an optical signal, said fibre amplifier comprising:

a length of optical fibre according to the invention, wherein the core region comprises a dopant material along at least part of the length, and means for providing pump radiation to the dopant material for pumping the dopant material so as to amplify the optical signal.

Normally, fibre amplifiers will, further comprise means for; spectrally separating the amplified optical signal from the pump signal, in order not to have pump radiation travelling in the fibre outside the amplifying region.

Especially for communication purposes, the dopant would comprise rare earth ions, such as erbium.

For other purposes, such as if it is desired to optically write gratings or other structures in the fibre or core region, or simply for increasing the refractive index of the core region, the dopant may comprise a photosensitive material, such as germanium and/or deuterium.

In an eleventh aspect, the invention relates to a fibre laser for outputting laser radiation, said fibre laser comprising a length of optical fibre according to any of the preceding claims, wherein the core region comprises a dopant material; along at least part of the length, means for providing pump radiation to the dopant material for pumping the dopant material so as to amplify the optical signal, and feedback means for selectively feeding back at least part of the amplified optical signal so as to repeatedly pass the amplified optical signal through the length of the optical fibre so as to further amplify the optical signal.

Especially for communication purposes, the dopant comprises rare earth ions, such as erbium.

Also, the dopant may comprise a photosensitive material, such as germanium or deuterium, in order to facilitate e.g. the wilting of gratings in the fibre or core region or for increasing the refractive index of the core region.

BRIEF DESCRIPTION OF THE DRAWINGS

FIG. 6 shows a fibre design based on a Honeycomb structure. A single hole creates a defect in the periodicity (which thereby forms the core region of the fibre).

FIG. 7 further illustrates the field distribution of the core mode. For a fibre with $\Lambda$=2.0 $\mu$m the core mode falls within the primary band gap in a wavelength range which corresponds approximately to 1.0 to 3.0 $\mu$m. Leakage-free, single mode wave guidance is thus obtained over this wavelength range. The dotted line relates to the effective index of the cladding structure.

FIG. 37 shows an asymmetric position of a defect void surrounded by periodic Kagomé cells.

FIG. 47 shows two voids in the core cell, one void with dimensions as the voids defining the vertices of the Kagomé cladding cell and the other void having larger dimensions.

In FIG. 50, the defect voids have the same dimensions as the voids used to form the Honeycomb cladding structure.

FIG. 57 shows defect voids/holes having smaller cross-section areas than the voids defining the vertices of the Kagomé cladding structure.

FIG. 67 shows a cell without a defect placed between two cells containing defect voids. The defect forming voids have larger cross-sectional areas than the voids defining the vertices of the simple Honeycomb cladding structure.

FIG. 70 shows a cell without a defect placed between two cells containing defect voids. One of the defect forming voids has a cross-sectional area as the voids defining the vertices of the simple Kagomé cladding structure, the other defect forming void has a cross-sectional area smaller than the cladding structure.

Theory

Figure 1:
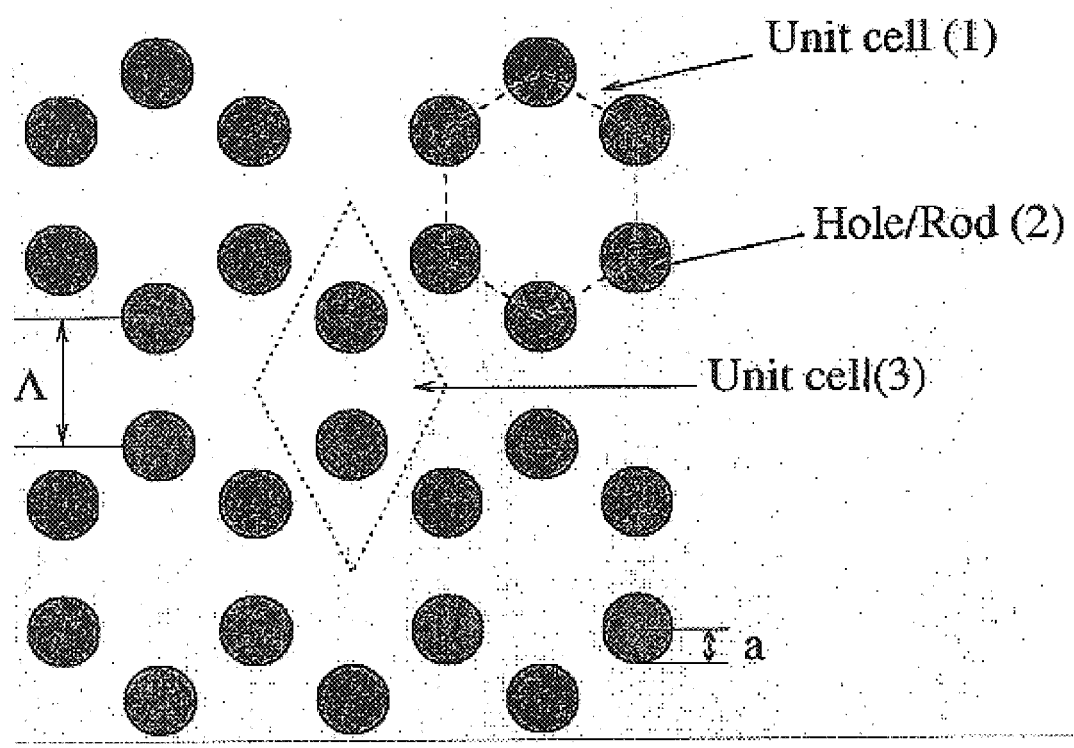
FIG. 1 shows a Honeycomb cladding structure with a two-dimensional periodicity.

In 1990 the first efficient method for calculating PBG's of photonic crystals was described. This method basically assumes the crystal to extend indefinitely in space. Then any solution is extended, and can be described as a sum of plane waves, due to the crystal periodicity.

A two dimensional photonic crystal is a dielectric structure which is periodic in two dimensions, and invariant in the third dimension.

The lattice defining the periodicity of the structure is defined by its lattice vectors $\overline{R}=n_1\overline{R}_1+n_2\overline{R}_2$ where $n_1$ and $n_2$ are integers. Then extended field solutions inside the crystal may be described as a plane wave multiplied by a Bloch function with the same discrete translational symmetry as the lattice structure. Therefore, any extended field solution (exemplified by the magnetic field) can be written as the infinite sum:

$$\overline{H}(\overline{k},\overline{r}) = e^{i\overline{k}\cdot\overline{r}}\sum_{\overline{G}}\sum_{j=1} h_j(\overline{k},\overline{G})\overline{e}_j(\overline{k}+\overline{G})e^{i\overline{G}\cdot\overline{r}} \quad (1)$$

Here $\overline{G}$ defines the reciprocal lattice, $\overline{G}\cdot\overline{R}=2\pi N$, where N is an integer. The vector $(\overline{k}+\overline{G})$ and the unit vectors $\overline{e}_1(\overline{k}+\overline{G})$ und $\overline{e}_2(\overline{k}+\overline{G})$ define a triad. $\overline{k}$ is the wave vector of the plane wave.

The actual field (and eigen frequencies), is found by expressing Maxwell's equations in the form of a Hermitian operator equation:

$$\nabla\times\left[\frac{1}{\varepsilon(\overline{r})}\nabla\times\overline{H}(\overline{r})\right]-\left(\frac{\omega}{c}\right)^2\overline{H}(\overline{r}) \quad (2)$$

To solve this equation, it is needed to Fourier-transform the inverse dielectric function as well:

$$\frac{1}{\varepsilon(\bar{r})} = \sum_{G} \varepsilon_{\bar{G}}^{-1} e^{i\bar{G}\cdot\bar{r}} \quad (3)$$

$$\varepsilon_{\bar{G}}^{-1} = \frac{1}{a_c} \int d^2 \bar{r} e^{-i\bar{G}\cdot\bar{r}} \frac{1}{\varepsilon(\bar{r})}$$

Here the integral is taken over a primitive unit cell having an area $\sigma_c$, and the sum is in principle over all possible $\bar{G}$-vectors. One finds the dielectric constants, by either using an FFT, or by finding analytical expressions for the Fourier coefficients. Here the latter technique has been used.

For a given choice of the reciprocal lattice vector $\bar{G}$ the following dependency from (1) and (2) is found:

$$\sum_{G} \begin{pmatrix} \bar{e}_2 \cdot \bar{e}_2' & \bar{e}_2 \cdot \bar{e}_1' \\ \bar{e}_1 \cdot \bar{e}_2' & \bar{e}_1 \cdot \bar{e}_1' \end{pmatrix} \cdot \begin{pmatrix} h_1' \\ h_2' \end{pmatrix} \varepsilon_{\bar{G}-\bar{G}}^{-1} \cdot L = \left(\frac{\omega}{c}\right)^2 \begin{pmatrix} h_1 \\ h_2 \end{pmatrix} \quad (4)$$

where $L=|\bar{k}=\bar{G}\|\bar{k}+\bar{G}|$. Inside the matrices, the operand is the vector $(\bar{k}+\bar{G}')$ if a prime is given, and the vector $(\bar{k}+\bar{G})$ if no prime is given. N such equations are rewritten (one for each of the N shortest $\bar{G}$-vectors), truncating the sum to the same N $\bar{G}'$-vectors, $(\bar{G}_i=\bar{G}_i')$, to a simple Hermitian eigen value matrix equation using a basis of N plane waves.

The first Brillouin zone is the set of points in the reciprocal lattice plane, which are closer to the lattice grid point $\bar{G}=\bar{0}$, than to any other reciprocal lattice grid points. The first Brillouin zone can be constructed from the irreducible Brillouin zone through the use of mirroring and rotational symmetry. For finding the possible PBG's of a photonic crystal, one solves the eigen value-problem for all the different values $\bar{k}_n(\bar{k}_n$ is $\bar{k}$ projected on the plane defined by the reciprocal lattice vectors) along the boundary of the irreducible Brillouin zone. Any frequency intervals, where no solutions are found define the PBG's of the photonic crystal.

For propagation restricted to the plane defined by the lattice sectors $\bar{R}$ (that is $\bar{k}=\bar{k}_2$) the two different plane wave directions in (4) de-couple into TM solutions (j=1 corresponding to the $\bar{e}_2\cdot\bar{e}_2'$) and TE solutions (j=2 corresponding to the term $\bar{e}_2\cdot\bar{e}_1'$). The TM solutions are defined as solutions having the electric field along the invariant direction, while TE solutions have the electric field in the plane defined by the lattice vectors. For $\bar{k}\neq\bar{k}_3$ the equations no longer de-couple, and the complete set of equations in (4) must be solved.

In order to calculate the electromagnetic properties of a specific defect within an otherwise periodic structure—such as the properties of the core region of the PCF's the outlined plane wave method may still be applied, where the smallest region describing the periodic structure is enlarged to include the defect (a so-called super-cell approximation). In this way a super-periodicity is introduced where also the defect is repeated periodic ally. Using a super-cell approximation the properties of the defect region may be accurately determined if the size of the super-cell is large enough to ensure that neighbouring defects are uncoupled. The numerical results presented in this potent hove been calculated using the principles outlined in this section.

The most basic requirement for waveguides to operate by PBG effects is that a periodic cladding structure exists and that this cladding structure is able to exhibit PBG effect. Within the invention is an example of a cladding structure with a two-dimensional periodicity—namely the Honeycomb structure illustrated in FIG. 1.

Figure 2:
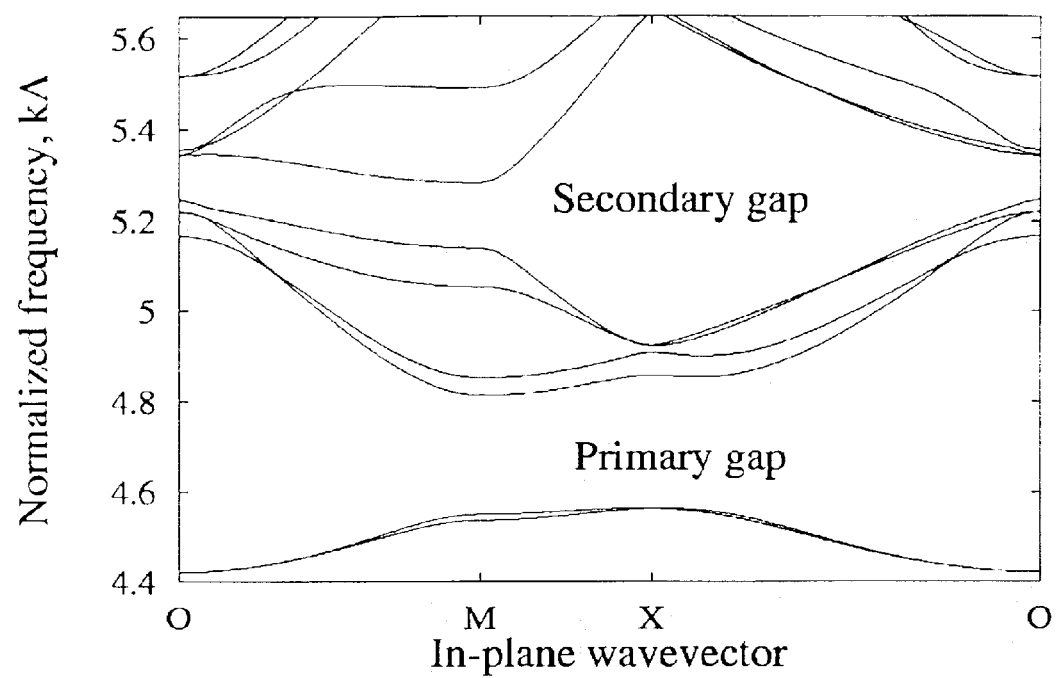
FIG. 2 shows a bond diagram for a basic Honeycomb photonic crystal with a hole filling fraction of 30%. $k\Lambda$ is the normalised frequency, where k is the free-space wave number ($=2\pi/\lambda$). $\Lambda$ is the distance between two neighbouring primary elements. The three high symmetry points of the Honeycomb crystal are indicated by O, M, and X.

Focusing first on the cladding structure alone, FIG. 2 illustrates the complete, out-of-plane two-dimensional PBG's which are exhibited for a basic Honeycomb structure with an air filing fraction of 30%, where the propagation constant, β, (which is defined as that component of the wave vector which is parallel to the centre axis of the holes) is fixed at 6/Λ (where Λ is the centre distance between to holes). The refractive index of the background material is set to be equal to 1.45. From FIG. 1 it is seen the appearance of two PBG's.

a) a primary gap between bands 2 and 3, and
b) a secondary gap between bands 6 and 7.

Figure 3:
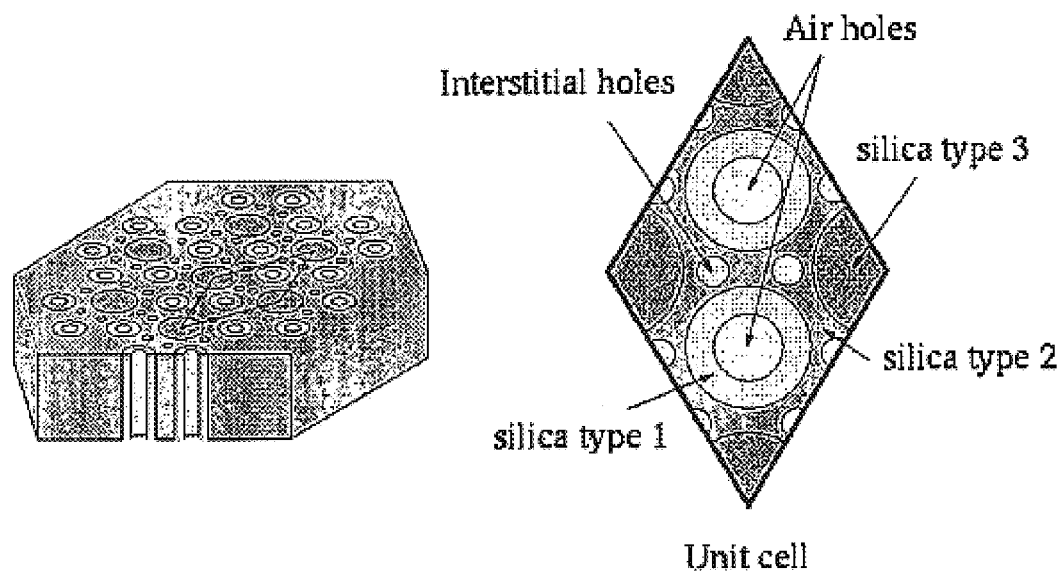
FIG. 3 shows a two-dimensional modified Honeycomb-based photonic crystal. Two differently doped silica glasses are used as well as undoped fused silica. The silica type 1 represents a capillary tube, and type 2 a solid cane from which the Honeycomb silica-air photonic crystal may partly be fabricated. The unit cell of the structure is marked by the solid-line rhomb.

The formation of these PBG's is the most fundamental requirement for PBG based components. In order to increase the two bond gaps, the impact on the size of the bond gaps from modification implied to the Honeycomb-based structure is illustrated. The important case of introducing several differently doped silica glasses in the structure is studied. For silica glasses a representative index range which may be achieved with today's doping technologies goes from to 3% and down to 1% of the nominal undoped value of silica which is approximately 1.45 at 1.55 μm. A schematic of the modified structure is shown in FIG. 3, where the rhomboidal solid line represents one choice of unit cell (a unit cell is defined as the smallest possible area which only through translation may be used to fully represent the periodic structure). The structure has a background material which comprises further small hole elements—which relates to those interstitial holes which have been observed in experimentally realised triangular photonic crystal cladding structures—and up to three different dopant levels of silica. The interstitial holes are easily introduced in a photonic crystal realised by the stock- and pull fabrication techniques currently used for PCF's.

Figure 4:
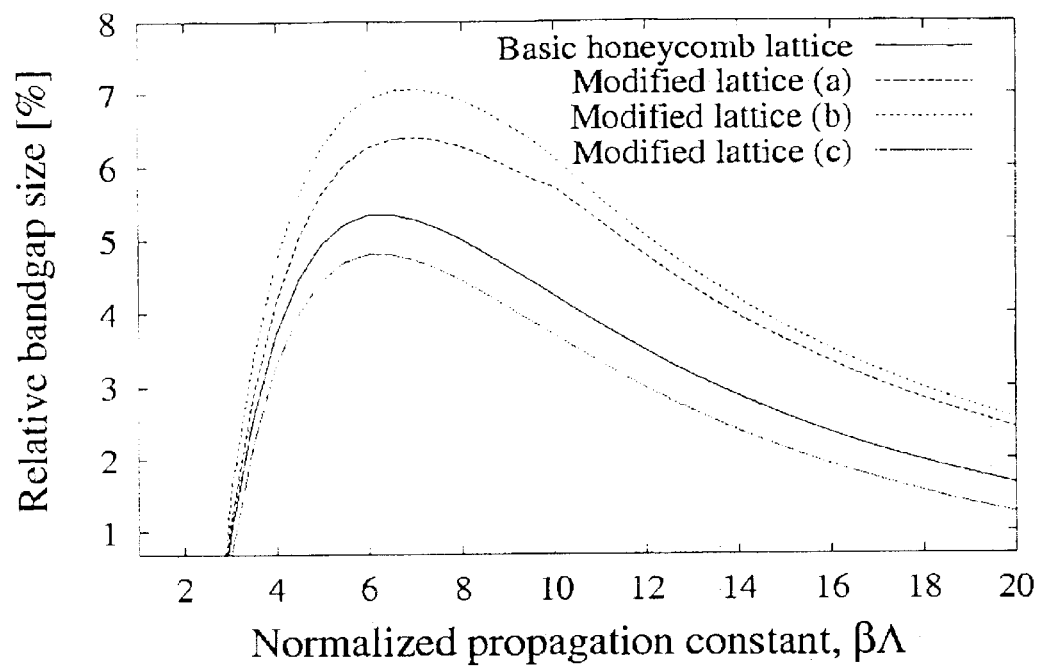
FIG. 4 shows the relative band gap size as a function of the normalised wave constant to the basic Honeycomb lattice (hole filling fraction=30), and three modified versions of the Honeycomb lattice.

In FIG. 4 the relative size of the primary gap is illustrated for the basic Honeycomb structure with an air filling fraction of 30%. The relative bond gap size is defined as the difference between the upper and lower frequencies of the bond gap divided by its centre frequency. Although no PBG's exists for the in-plane case of silica-air structures (β=0), complete PBGs are found to open up when moving out of the plane. In the figure is also included three cases of modified Honeycomb structures:

a) interstitial holes introduced ($f_{int}$=8%)
b) interstitial holes and three differently doped silica glasses ($n_1$=1.44, $n_2$=1.45, $n_3$=1.47)
c) three differently-doped silica glasses ($n_1$1.47, $n_2$=1.45, $n_3$=1.44).

The indices refer to the three silica types indicated in FIG. 3, and for the structures comprising three silica dopants the outer diameter of the tube and cane (silica type 1 and 3, respectively) have been set equal to Λ. For the basic structure (undoped silica and air) a maximum PBG size of 5.3% at beta=6.6/Λ is observed. This size may be increased to 6.4% by adding interstitial holes to the structure, and further increased to 7.1% by lowering the refractive index of the silica surrounding the air holes (silica type 1) while increasing the index of the silica forming the cones (silica type 3).

The Honeycomb photonic crystal is a structure with high-index regions—denoted nodes (i.e. the region with silica type 3 in FIG. 3) which are isolated by voids/holes.

Figure 5:
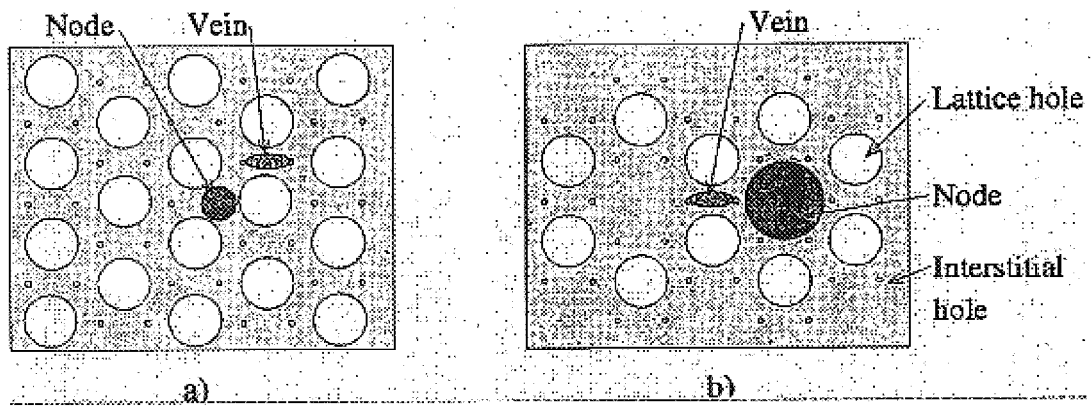
FIG. 5 shows a schematic illustration of the concept of nodes (high-index areas) and veins (holes/voids), and an illustration of the superior properties of the Honeycomb structure over the triangular structure as well as the influence of interstitial holes in triangular structures a), and Honeycomb structures b).

The region bridging two nodes is denoted a vein in FIG. 5.

It has been found that the largest bond gaps are achieved for structures having most isolated nodes (high-index regions), and having nodes with the highest possible refractive index. Veins (bridges) may be narrowed further in the Honeycomb-based structures through the interstitial holes, whereas the interstitial holes fall right in the centre of the node in the triangular structure. Thus, it is evident that interstitial holes may be either advantageous or disadvantageous, depending or their location.

To further support that the nodes should have the highest possible index, it is observed how the size of the primary band gap is, indeed, decreased for the structure (c) modified by lowering the index of the nodes, while increasing the index of the silica surrounding the air holes.

Although not illustrated the same conclusions is found to be valid for the size of the secondary band gap. This result demonstrates the advantages of introducing differently doped silica glosses in the Honeycomb-based photonic crystal, and isolating the high-index regions by surrounding them with materials with lower refractive index.

According to the inversion, cladding structures having holes/rods placed in a so-called Kagomé structure are also advantageous. Both Kagomé and Honeycomb structures have intrinsically larger nodes and relatively narrower veins than the triangular structure. Further more, for the triangular structure, it should be noted how the interstitial holes which have been observed in photonic crystal fibres with a triangular hole arrangement in the cladding fall right in the centre of the nodes (thereby severely damaging their, ability to act as high index centres, and the cladding structure to exhibit PBG effect). Thus, it is an advantage of the Kagomé and Honeycomb structure that the interstitial holes leave the nodes undisturbed, and at the some time narrow the veins even further.

By locally breaking the periodicity of a photonic crystal, a spatial region with optical properties different from the surrounding bulk photonic crystal can be created. If such a defect region supports modes with frequencies falling inside the forbidden gap of the surrounding full-periodic crystal, these modes will be strongly confined to the defect. This is the principle on which the operation of the PBG guiding fibres relies, namely a complete out-of-plane 2D band gap exhibited by the photonic crystal cladding, and a correctly designed defect, forming a spatial region to which very strong transverse confinement car be achieved. For this defect region to exhibit optical properties different from the surrounding periodic structure (i.e., be able to support a localised mode) it is important to notice that it is not a requirement that the defect region has a higher index than its surroundings.

For a non-periodic dielectric surrounding media this would be the only case under which localisation can occur (which is of course the case of total internal reflection utilised in all conventional optical waveguides). Leakage-free guidance 0' light confined to a region with a lower index than its surroundings would, therefore, not be expected to be possible from index guidance waveguide theory but it the surrounding material exhibits PBG effects even a low-index defect region may be able to localise the light, and thereby act as a (new) highly unusual waveguide.

Figure 7O:
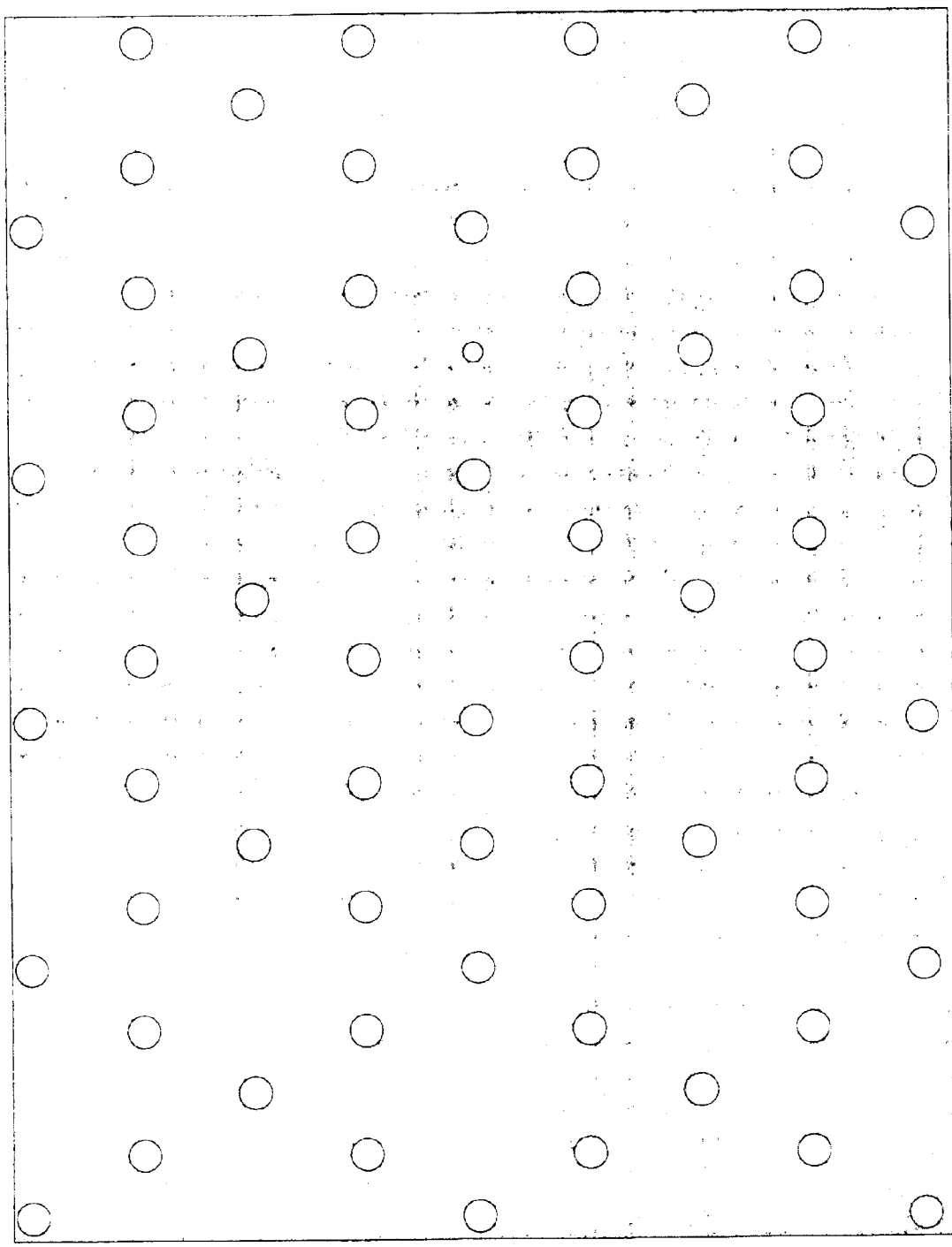
FIG. 7 shows an illustration of the two first band gaps (primary and secondary gaps) of a Honeycomb PCF with a cladding hoe filling fraction of 10% and a defect hole with same size as the cladding holes. Within the primary band gap the extra air; hole in the core of the fibre causes a single degenerate mode to appear. This 'defect' mode is localised around the core of the fibre, and does not couple to the cladding structure (as it is here forbidden due to the PEG effect)
Figure 71:
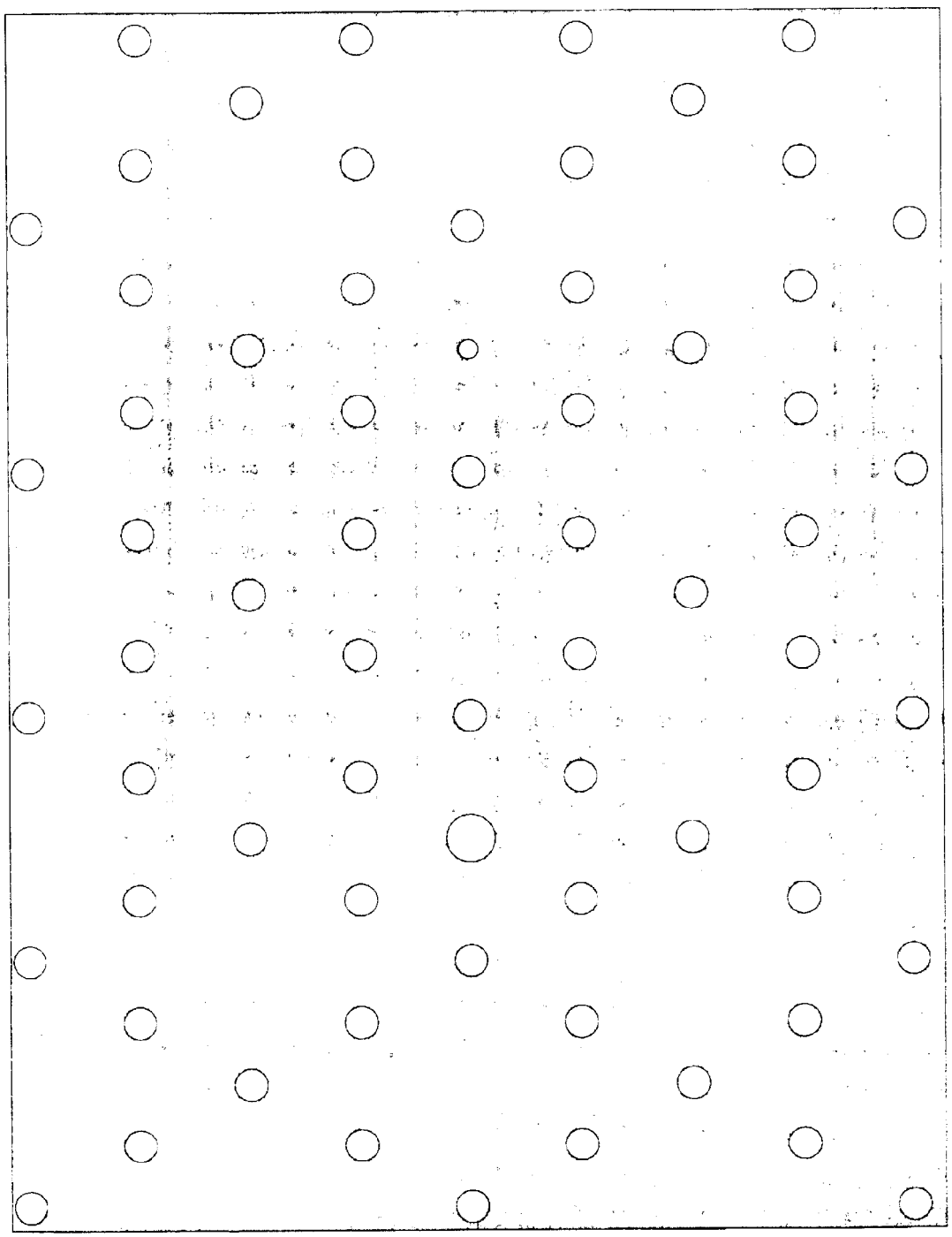
FIG. 71 shows a cell without a defect placed between two cells containing defect voids. One of the defect forming voids has a cross-sectional area smaller than the voids defining the vertices of the simple Kagomé cladding structure, the other defect forming void has a cross-sectional area larger than the cladding structure.
Figure 72:
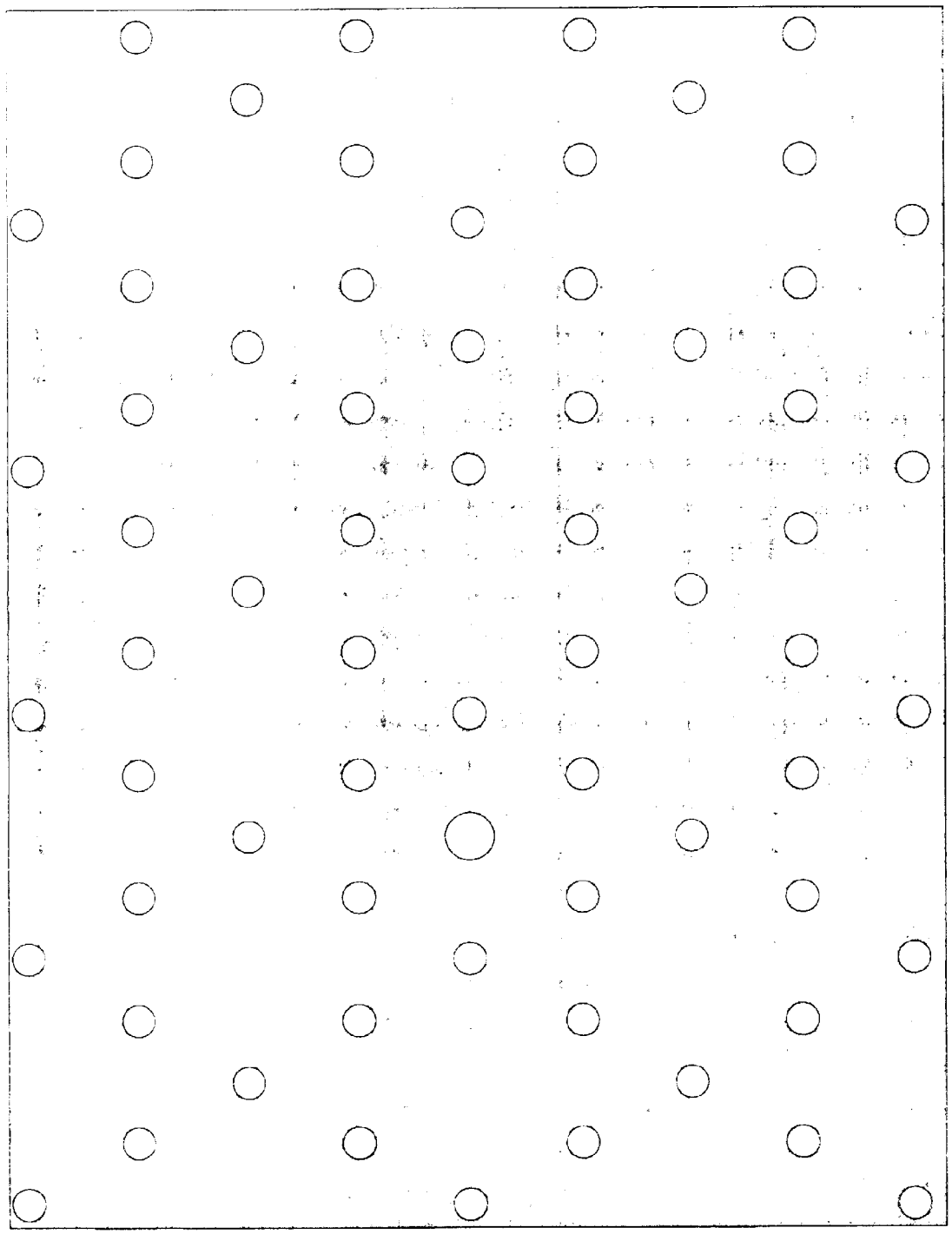
FIG. 72 shows a cell without a defect placed between two cells containing defect voids. One of the defect forming voids has a cross-sectional area as the voids defining the vertices of the simple Kagomé cladding structure, the other defect forming void has a cross-sectional area larger than the cladding structure.
Figure 73:
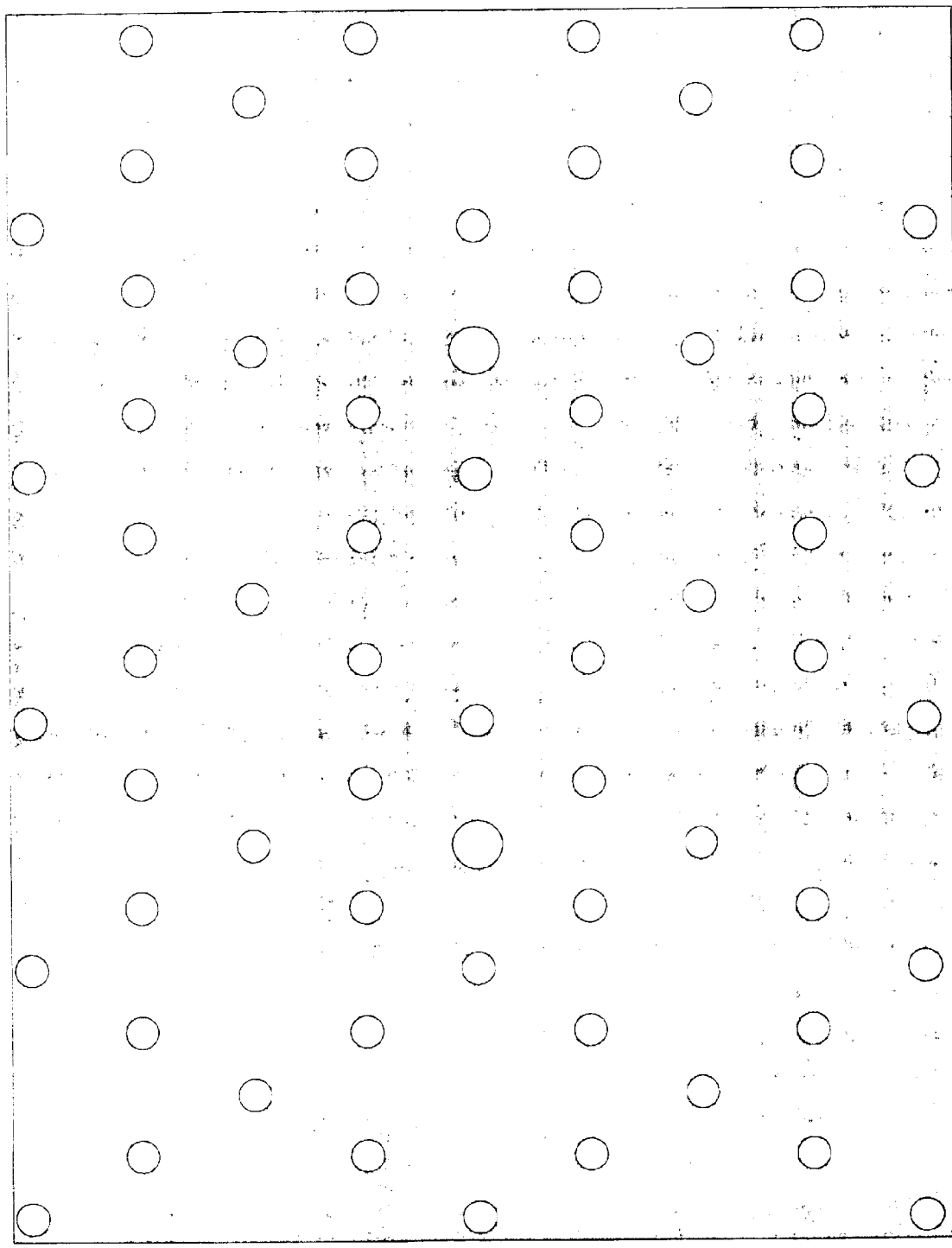
FIG. 73 shows a cell without a defect placed between two cells containing defect voids. The defect forming voids have larger cross-sectional areas than the voids defining the vertices of the simple Kagomé cladding structure.

For a fibre design (see FIG. 6) based on a Honeycomb structure and a single hole creating a defect in the periodicity (which thereby forms the core region of the fibre) the primary and secondary band gaps of the cladding are depicted in FIG. 7. The fibre has a cladding air filling fraction of 10% and the defect 'core' hole has the some size as the cladding holes. Inside the primary gap, a single defect-mode traversing the gap from approximately $\beta/\Lambda=5$ to 17 is observed. This mode is caused solely by the introduction of the defect air hole in the Honeycomb structure.

Figure 8:
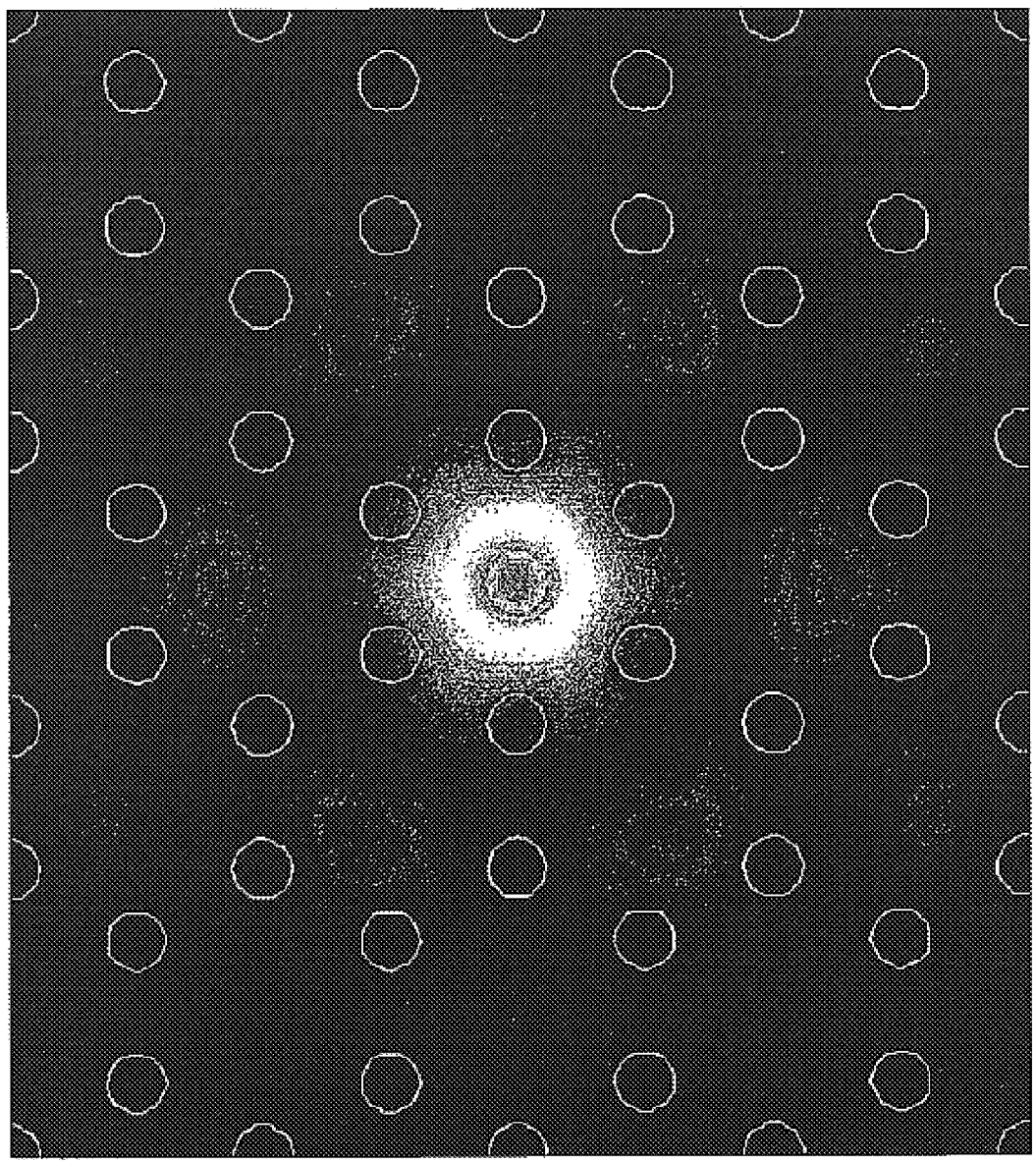
FIG. 8 shows a PBG guided mode for a Honeycomb PCF with hole filling fraction=10%. The figure shows the electric field squared for the 'defect' mode illustrated in FIG. 7. Light areas indicate high field intensity. The real space structure has been superimposed to illustrate the localisation of the 'defect' mode to the extra air hole in the core of the fibre.

For the full periodic structure, exactly the some PBG's (with no modes inside) with identical boundaries to those of the crystal; including the defect is found. This defect-mode is strongly localised to the region comprising the extra air hole (albeit this is a low-index region). FIG. 8 illustrates the calculated squared amplitude or the E-field. The mode was calculated or a $\beta/\Lambda$-value of 8.0. For this value, the defect-mode is approximately in the middle of the band gap, and the expected strong localisation of the mode is apparent. This mode does not couple to cladding modes in the PCF, (since the mode is falling inside the bond gap of the photonic crystal cladding) and loss-less guidance may therefore, in principle, be achieved over long lengths.

Although almost the entire field of the defect mode for this particular PCF is distributed in the silica, full confinement of light in air is—in principle—possible for PBG guiding fibres. Such fibres would, naturally, have a tremendous potential in both telecommunications and sensor areas. Also included in the FIG. 7 is the radiation line (dotted line), defined as the lowest-frequency allowed mode in the full periodic structure—and relates to the effective index, $n_{c-en}$, of the cladding structure as $1/n_{c-en}$. Below this line is a semi-infinite 'band gap', where no modes exist. This is the region in which all TIR based fibres (Including triangular high-index core PCF's) operate, since a high-index defect causes at least one mode to appear below this line. Such index-guided modes are seen not to be a feature of the low-index core Honeycomb-based PCF's.

Improved cladding structures, as e.g. modified Honeycomb of Kagomé structures, means that larger band gaps may be achieved. Larger bond gaps results in stronger confinement of the defect mode, and will, therefore, not only be of importance for wider 'tuning'-ranges of the fibres, but also for very robust operation of these with respect to low propagation and bending losses.

A further advantageous is the high flexibility of the PBG guiding fibres. By the PBG effect it is, as demonstrated, possible to open up forbidden frequencies regions by designing the micro-structured cladding correctly, and by introducing a defect site (having one or more holes/rods) to localise light within this region. By independently optimising the cladding and the defect structures, it is thus possible to tailor the properties of the fibres.

Figure 9:
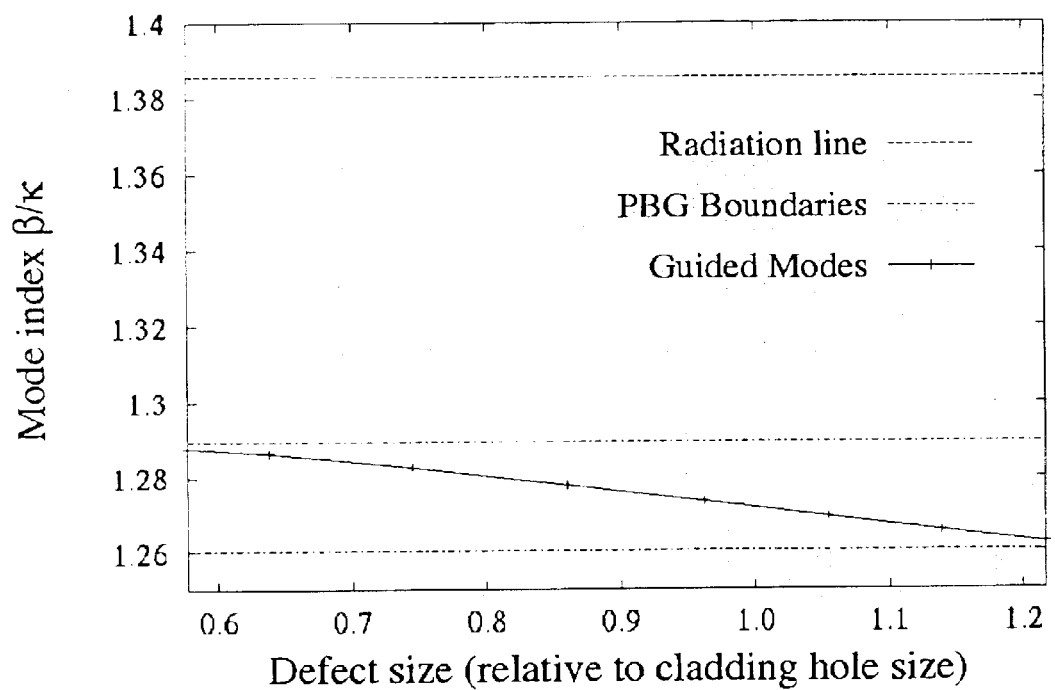
FIG. 9 shows the effect of tuning the frequency of the core-mode precisely within the PSG by varying the size of the central hole. The plot is for a fixed value of $\beta\Lambda$=5. The hole filling factor of the cladding is 18%. The size of the single, central defect hole is varied.
Figure 10:
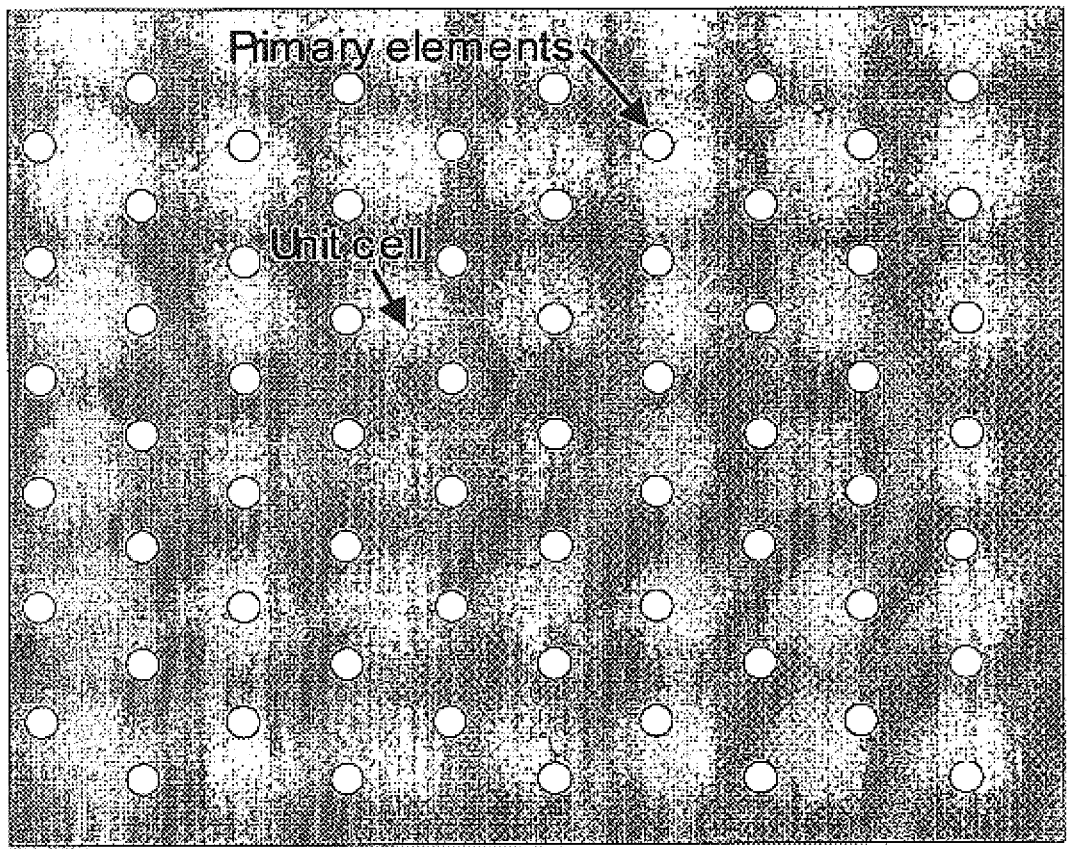
FIG. 10 shows a basic triangular lattice formed by primary elements. The unit cell of the triangular lattice is also depicted.
Figure 11:
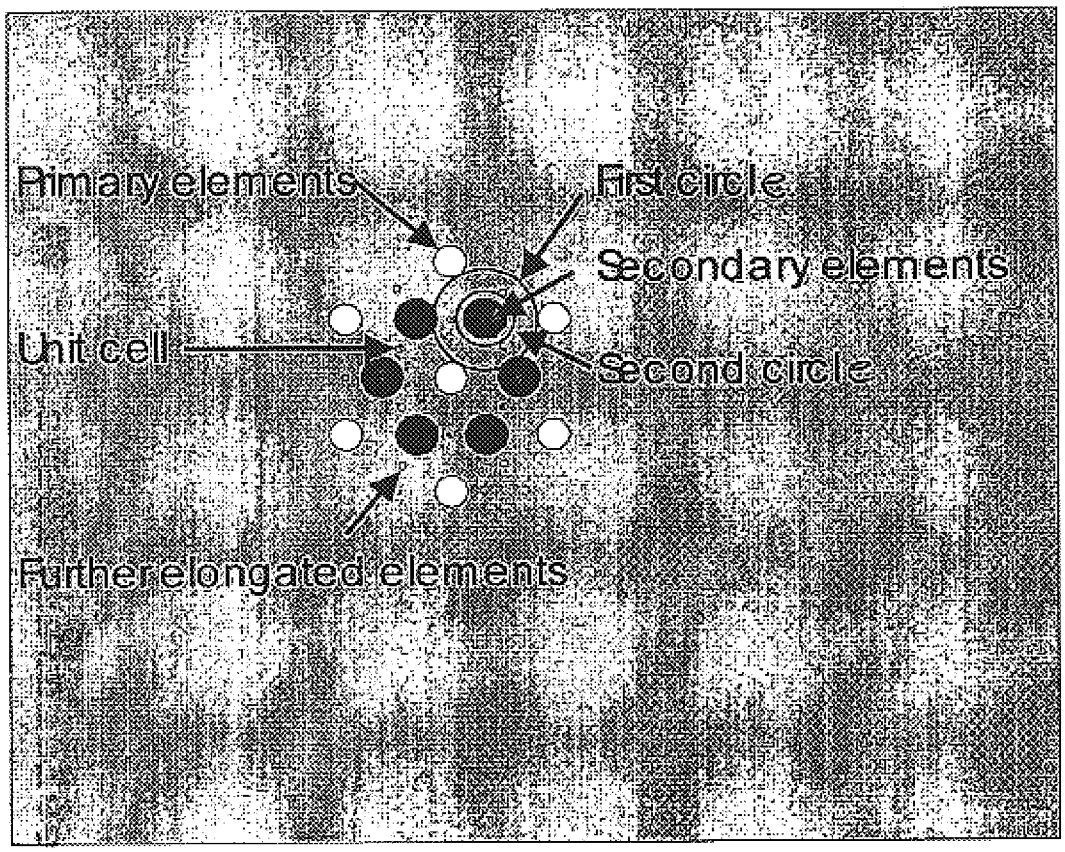
FIG. 11 shows a basic triangular lattice and a corresponding unit cell. The triangular structure is defined by primary elements. Furthermore, further elongated elements and secondary elements are shown. A first circle is defined as being the largest possible circle having a centre positioned not outside the unit cell and not comprising any part of any primary elements. A second circle is defined as being the largest possible circle having a centre not positioned outside the unit cell and not comprising any part of any primary elements and any part of any further elongated elements.
Figure 12:
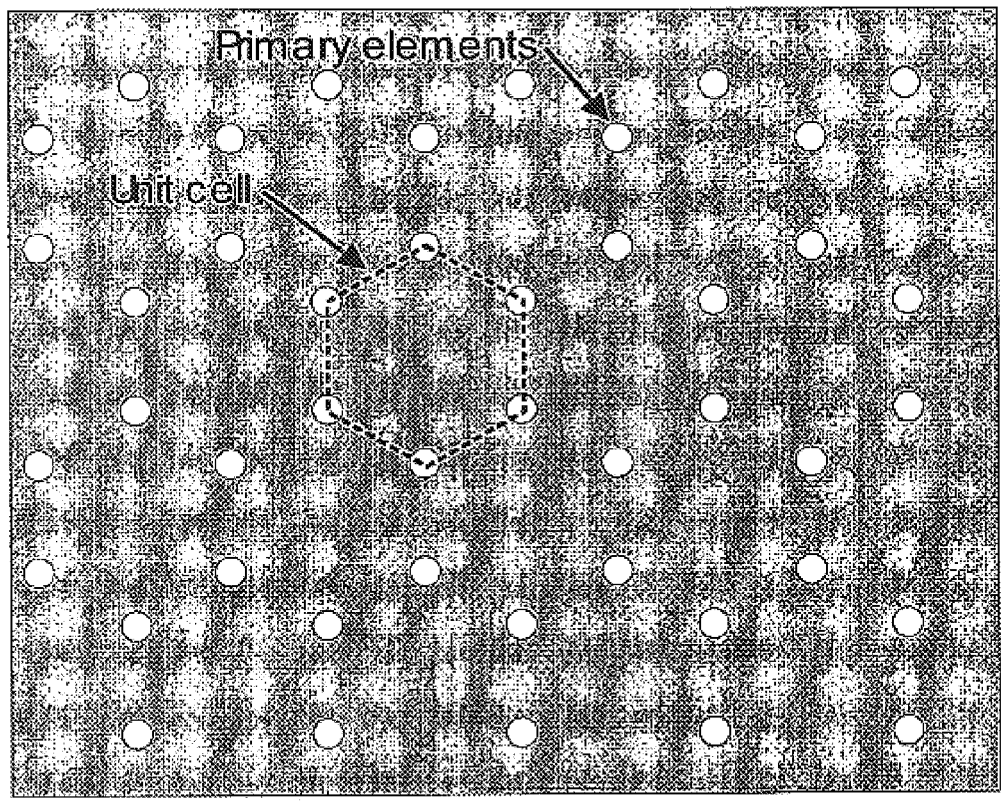
FIG. 12 shows a Honeycomb lattice formed by primary elements. The unit cell of the Honeycomb lattice is also depicted.
Figure 13:
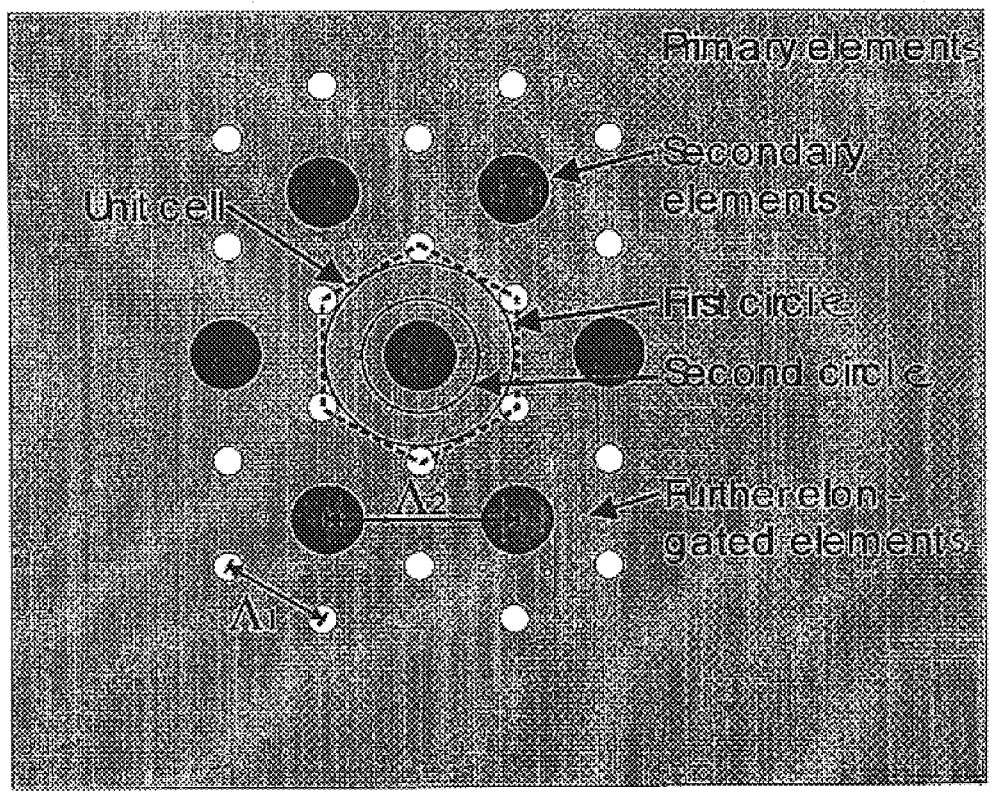
FIG. 13 shows a basic Honeycomb lattice and a corresponding unit cell. The Honeycomb structure is defined by primary elements. Furthermore, further elongated elements and secondary elements are shown. A first circle is defined as being the largest possible circle having a centre positioned not outside the unit cell and not comprising any part of any primary elements. A second circle is defined as being the largest possible circle having a centre not positioned outside the unit cell and not comprising any part of any primary elements and any part of any further elongated elements. The distance between two neighbouring primary elements is denoted A. The distance between the centres of two first circles is denoted $\Lambda_2$.
Figure 14:
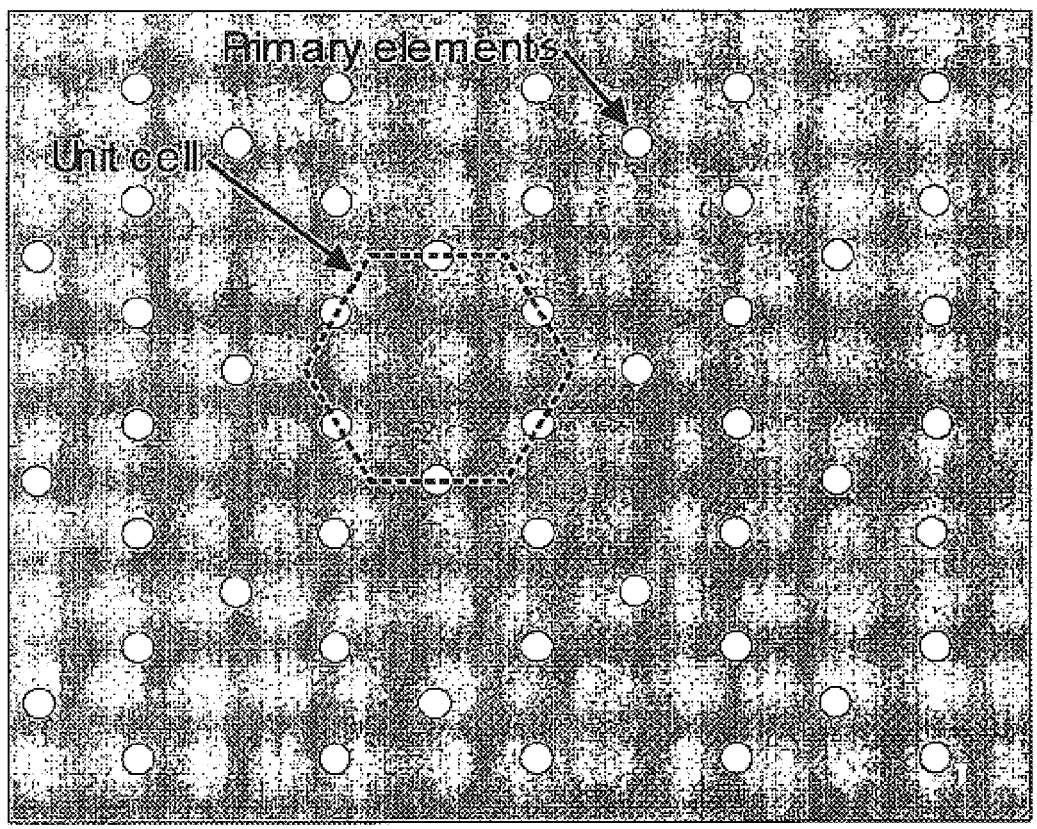
FIG. 14 shows a Kagomé lattice formed by primary elements. The unit call of the Kagomé lattice is also depicted.
Figure 15:
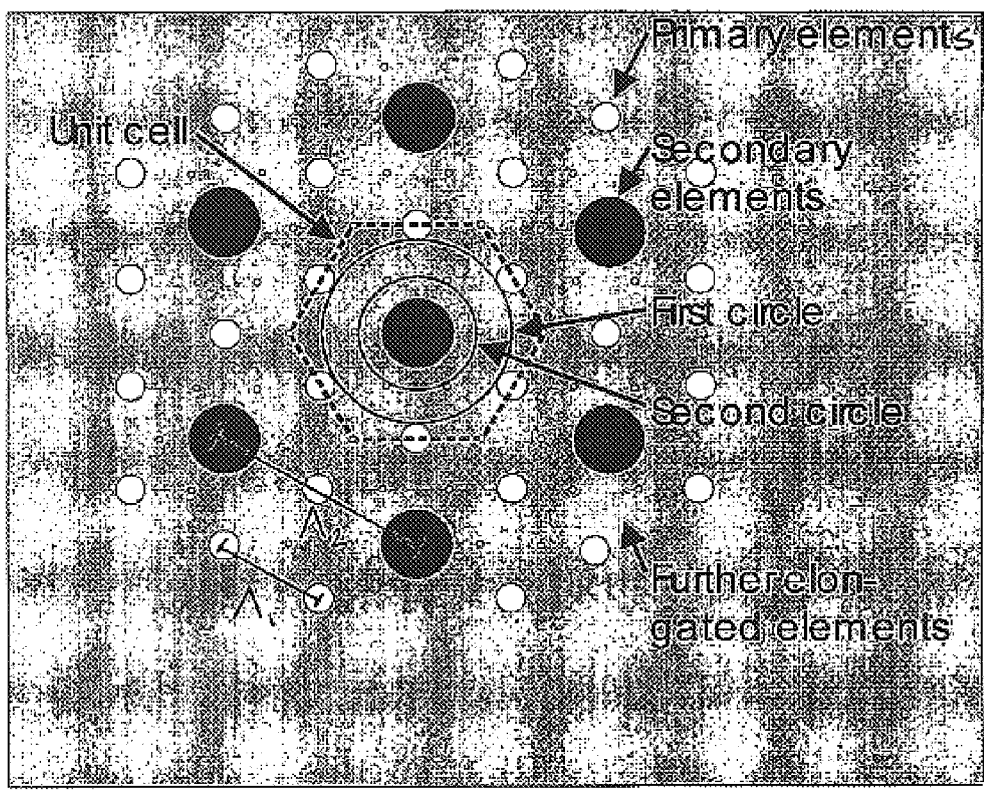
FIG. 15 shows a basic Kagomé lattice and a corresponding unit cell. The Kagomé structure is defined by primary elements. Furthermore, further elongated elements and secondary elements are shown. A first circle is defined as being the largest possible circle having a centre positioned not outside the unit cell and not comprising any part of any primary elements. A second circle is defined as being the largest possible circle having a centre not positioned outside the unit cell and not comprising any part of any primary elements and any part of any further elongated elements. The distance between two neighbouring primary elements is denoted $\Lambda_2$. The distance between the centres of two first circles is denoted $\Lambda_2$.

In FIG. 9 is illustrated how it is possible—or a fibre with a design as in FIG. 6—that by varying the size of the central defect hole, but keeping the cladding structure fixed, to precisely tune the frequency of the defect mode within the PBG region of the cladding. Although this is only been illustrated for a defect site introduced by a single additional hoe, many other ways of creating such defects may be thought of, E.g. for polarisation managing purposes the introduction of asymmetric defects (possibly with a very large defect region) seem as a correct deign route.

DETAILED DESCRIPTION OF THE INVENTION

Many different realisations of periodic cladding structures exist for low-index-core PBG waveguides, because they ran consist of a void, hole, or any suitable (additional or missing) material(s) disposed periodically in a (first material) matrix. By low-index-core PBG waveguide is meant any structure capable of the guiding electromagnetic fields according to the present invention, such as optical fibres, optical fibre amplifiers, fibre lasers and optical fibre based sensors. Another group of PBG waveguides comprises planar waveguide structures, such as sensors, splitters, couplers, multiplexers, amplifiers and lasers.

Figure 16:
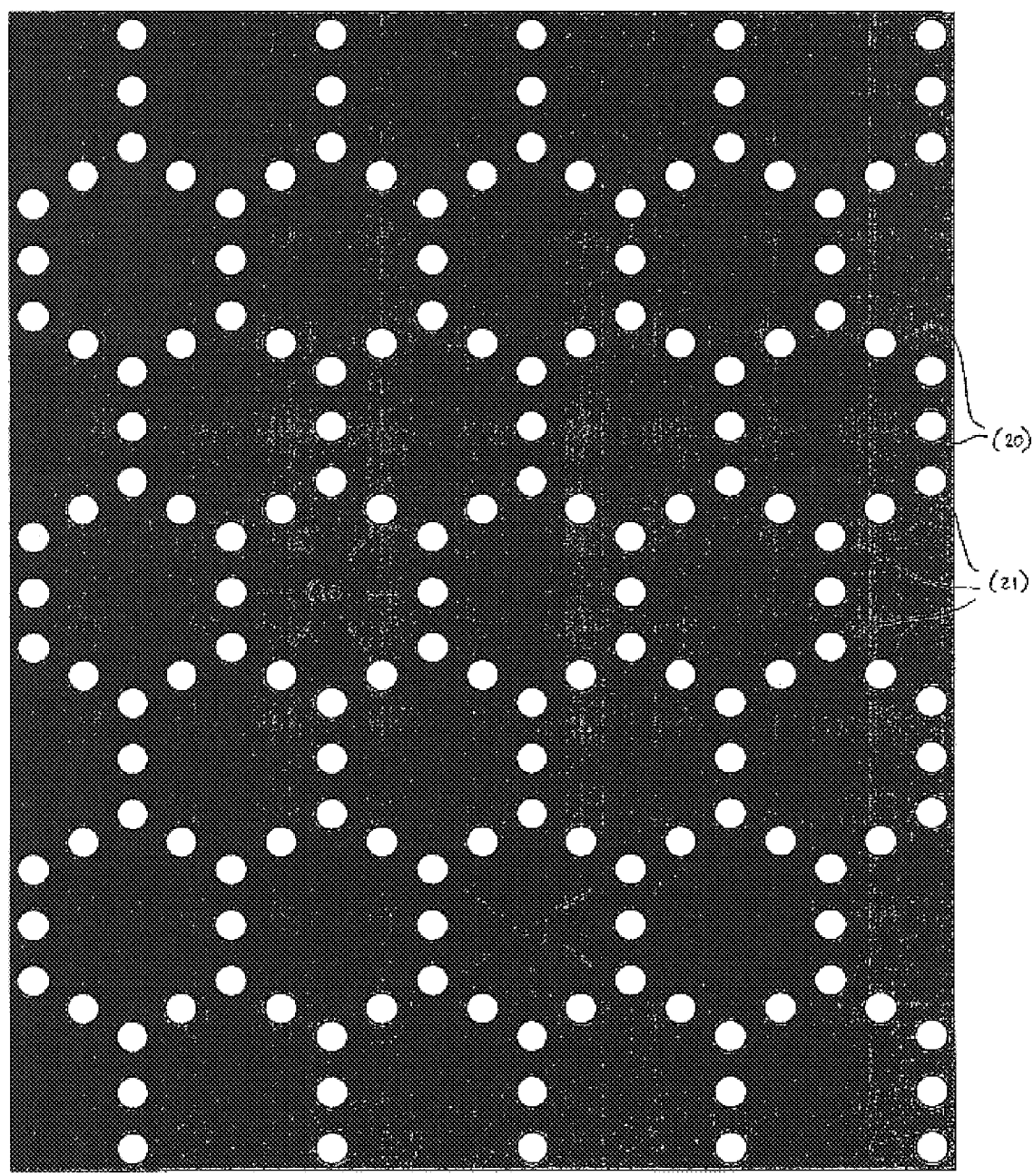
FIG. 16 schematically shows a further embodiment of a cladding cross section in which a Honeycomb structure is formed by adding additional (equal sized) holes between the original ones defining the vertices of the fundamental hexagonal structure.

An example of such a periodic micro structured cladding shown in FIG. 16, where additional voids (20) have been centred on a straight line between the original voids (21) forming the 2-dimensional hexagonal (Honeycomb) structure. The function of the additional voids is to modify the penetration of the electromagnetic field between the different unit cells (low-refractive index cladding areas can locally limit the cladding field intensity) and hereby add additional means of adjusting the waveguiding properties of the fibre/waveguide. It is also noteworthy that the structure illustrated in FIG. 16 may be seen as a superposition of the Honeycomb structure (formed by the voids (21)) and the Kagomé structure (formed by the voids (20)).

Figure 17:
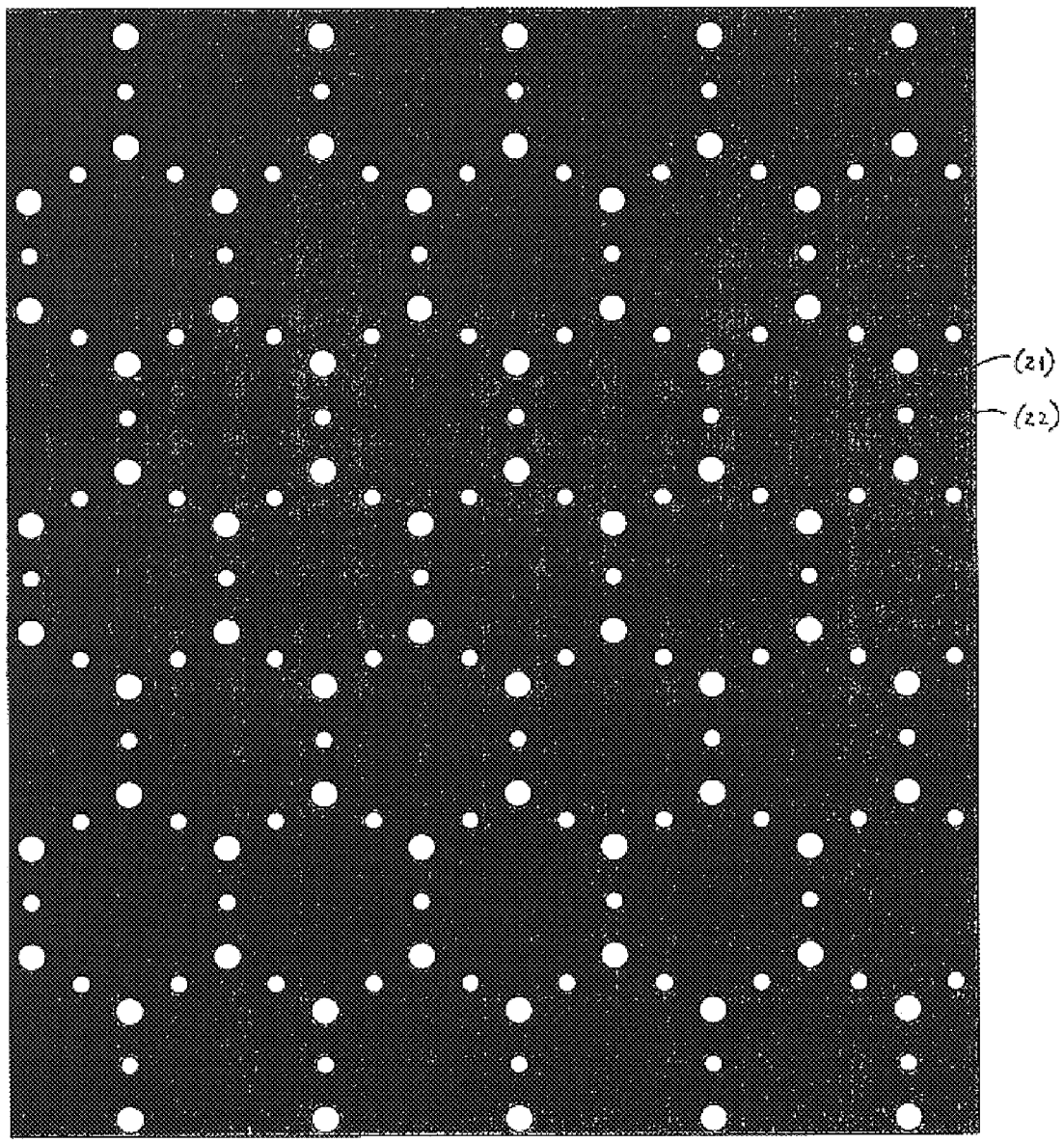
FIG. 17 illustrates a further embodiment of a cladding cross section in which a Honeycomb structure is formed by adding additional (smaller sized) holes between the original ones defining the vertices of the fundamental hexagonal structure.
Figure 18:
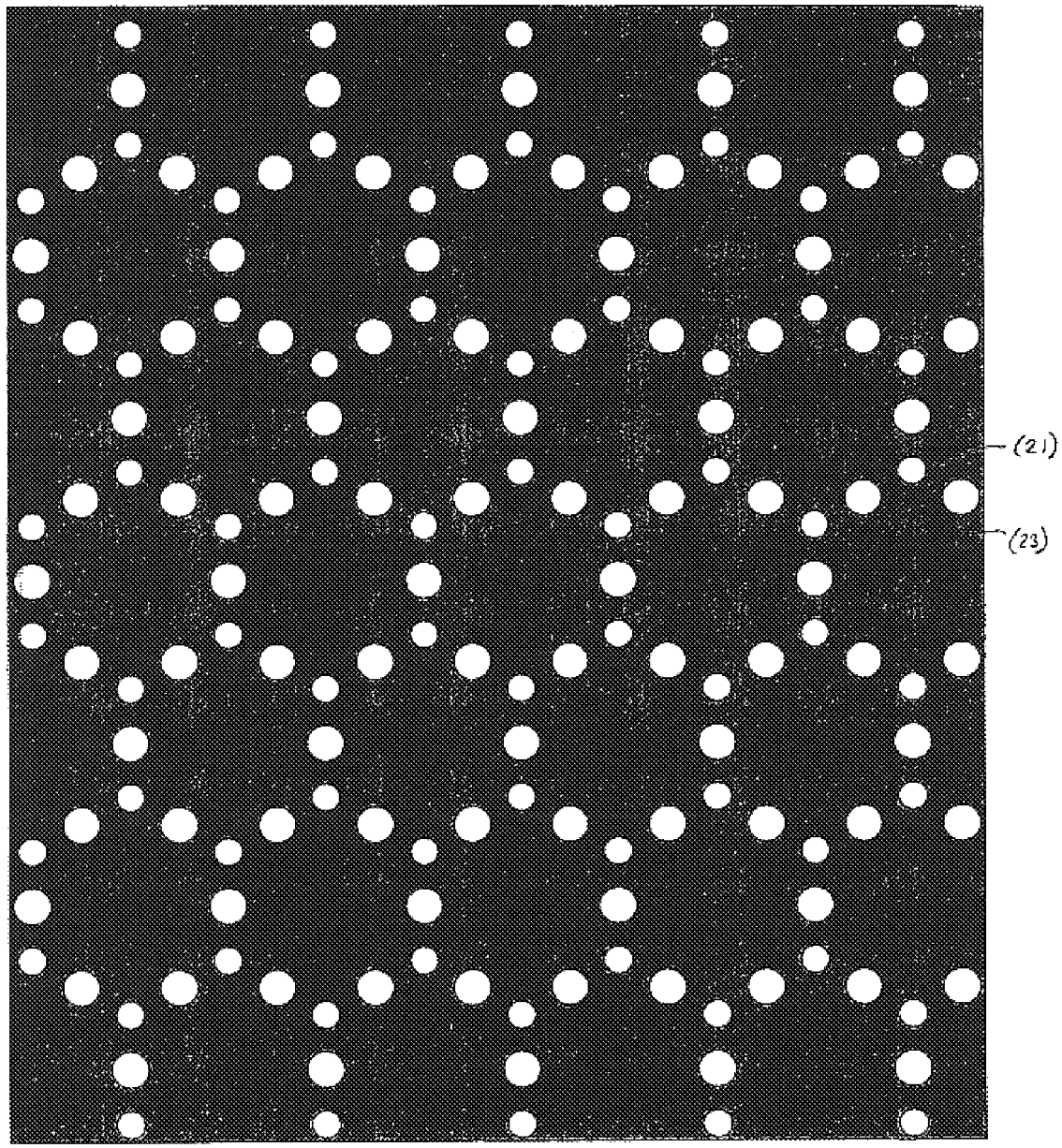
FIG. 18 illustrates a further embodiment of a cladding cross section in which a Kagomé structure is formed from a Honeycomb structure by adding additional (larger sized) holes between the original ones defining the vertices of the fundamental hexagonal structure.

Further possibilities of adjusting the photonic-band gap-forming properties of the periodic hexagonal cladding structures are exemplified by the illustrations in FIG. 17 and FIG. 18, in which the mutual cross-section areas of the cladding forming void are modified. In the example of FIG. 17, the additional holes/voids (22) are formed by a smaller cross-section area than the ones (21) that are not placed on a straight line between neighbouring voids.

In FIG. 18, the additional holes (23) on the contrary have a larger cross section area, whereby the field penetration properties between unit cells are controlled in a new way. It should also be noted, that the examples of hexagonal cladding structures presented here not necessarily have to be formed by circular voids, but any periodically repeated cross sectional shape may be used to for the PBG's of the cladding (e.g., holes/voids of triangular, square, elliptical or any other shape may be applied).

In addition, its should be pointed out that minor variations from the ideal structures described here may introduced during fabrication, but as long as the fundamental physical limits of the fibres are preserved, the structures are covered by the present invention.

Figure 19:
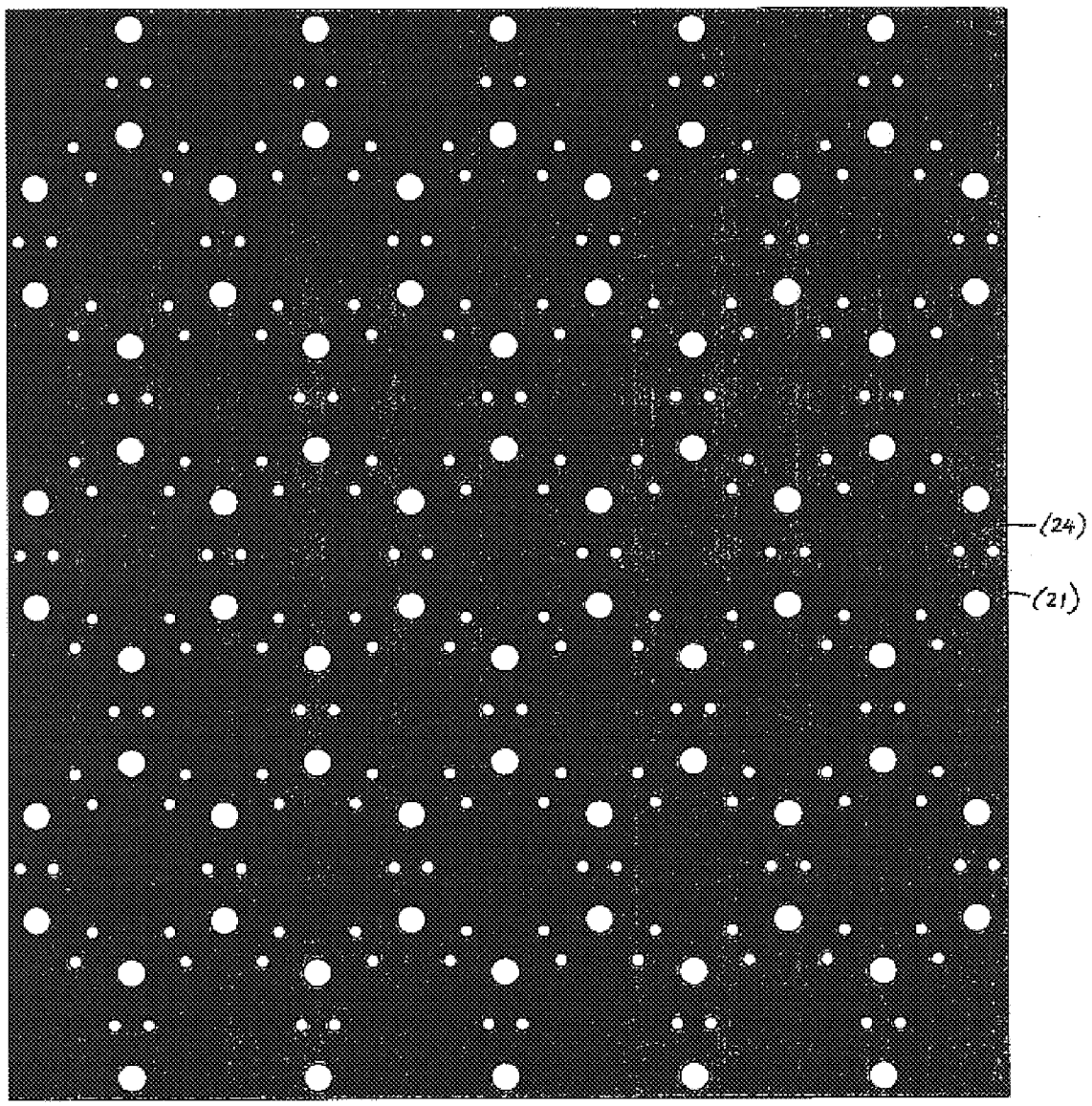
FIG. 19 schematically shows a further embodiment of a cladding cross section in which a Honeycomb structure is formed by adding a group of two additional (smaller) holes between the original ones defining the vertices of the fundamental hexagonal structure.

Another possibility of engineering the PBG properties of the cladding structures, and thereby create new waveguiding properties of the optical waveguides/fibres, is to replace single voids by groups of voids. An example of such a design is illustrated in FIG. 19, which may be seen as a further development of the structure of FIG. 16, in which the additional hole/void (20) placed on a straight line between two neighbouring holes has been replaced by a group (24) of two voids with smaller cross-section area.

Figure 20:
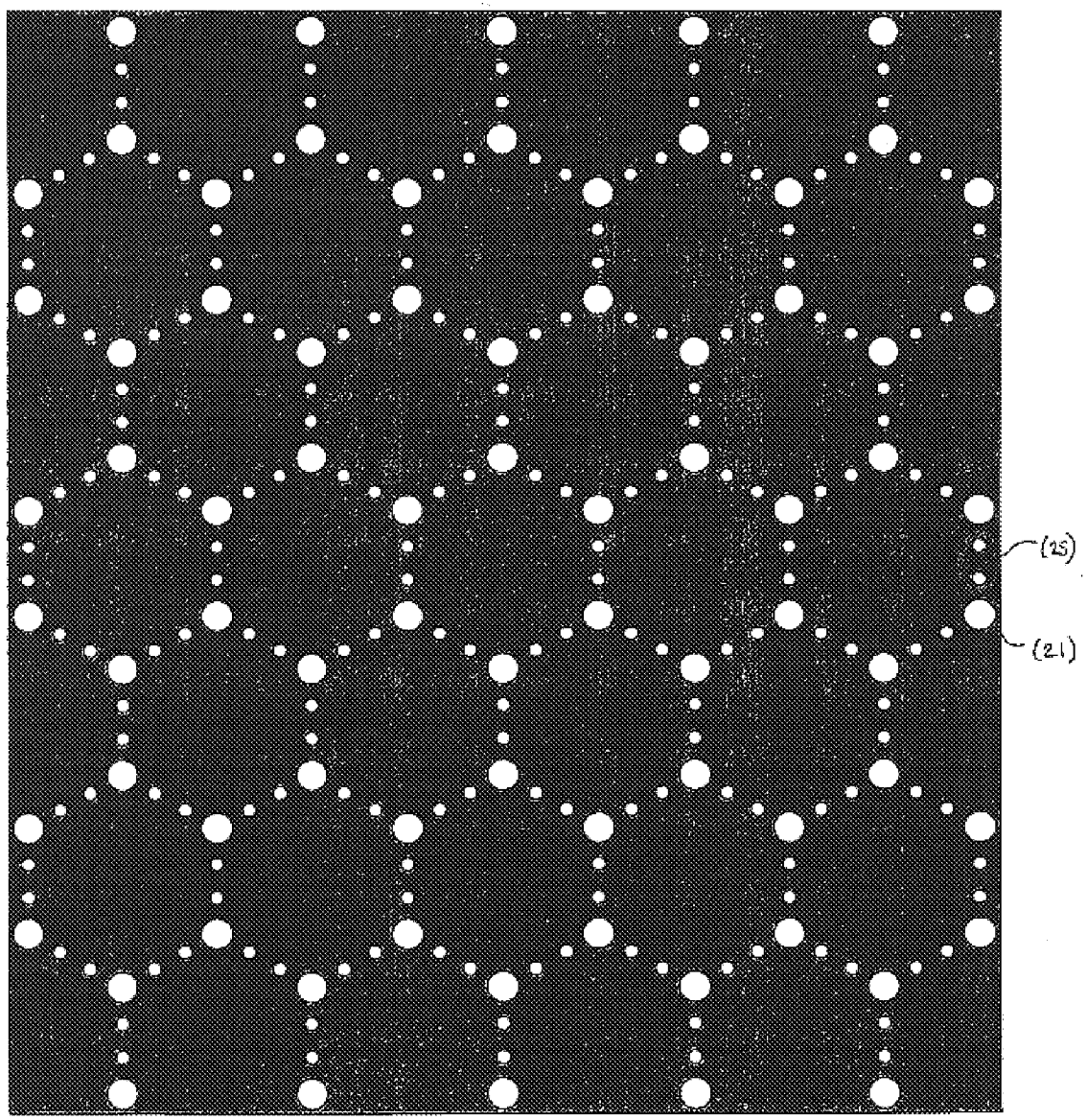
FIG. 20 schematically shows a further embodiment of a cladding cross section in which a Honeycomb structure is formed by adding a group of two additional (smaller) holes between the original ones defining the vertices of the fundamental hexagonal structure, but in contrast to FIG. 19 the group of two smaller voids is turned 90 degrees.

A different orientation of the group of additional voids (25) is illustrated in the example of FIG. 20, resulting in a configuration, where four voids are placed on a straight line. Naturally more complex groups of voids may be placed in the overall structure, and direct extensions of the outlined approach are the use of groups with more than two additional voids, and the shaping of these with cross-sections different from the circular one.

Figure 21:
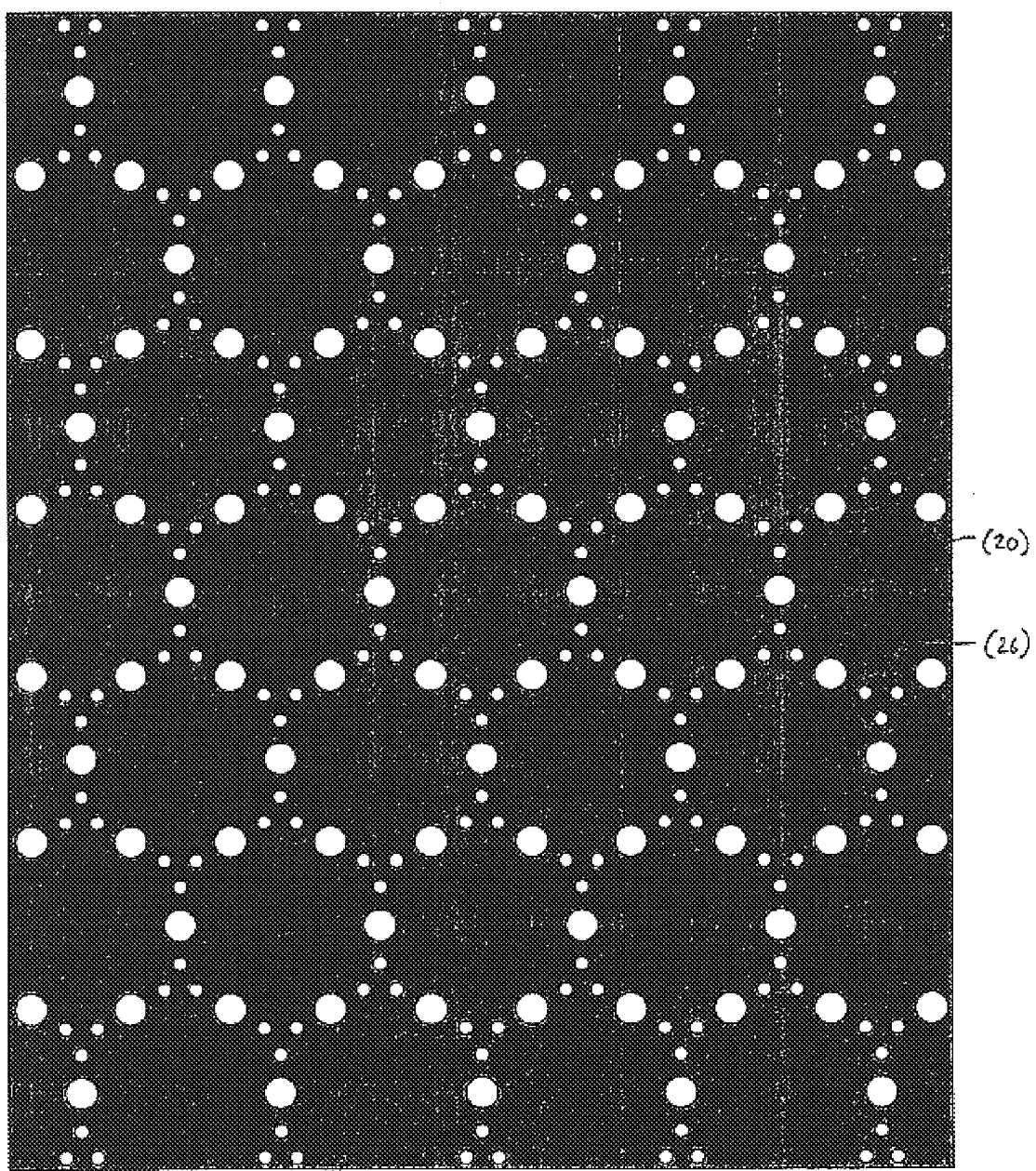
FIG. 21 illustrates a combination of the Honeycomb and Kagomé structure in which the Honeycomb defining elements have been replaced by a group of three elements in a equal sided triangular structure.

A different example of the combined Kagomé and Honeycomb structures is shown in FIG. 21 in which the voids (20) placed in the Kagomé structure is maintained compared to FIG. 16, wherein each the of voids in the superimposed Honeycomb structure is replaced by a group of three smaller voids (26) forming an equal sided triangular shaped figure. The specific orientation of the three-element group shown in FIG. 21 is not the only possibility, and numerous other orientations, relative magnitudes of the cross-sectional areas of the voids/rods and the numbers of elements in each sub-group is covered by this invention.

Figure 22:
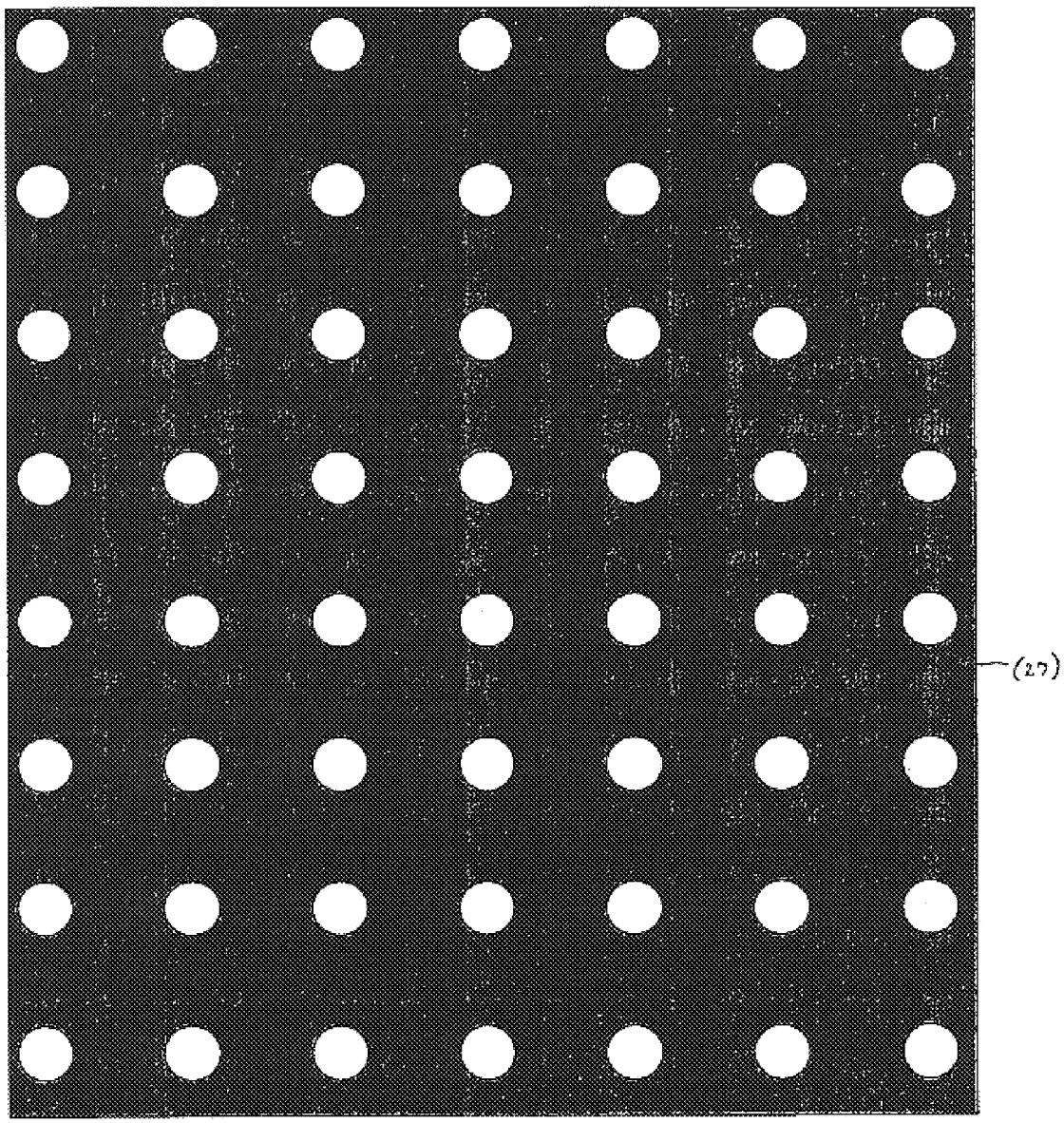
FIG. 22 illustrates an embodiment of a periodic cladding in which the voids/rods are placed in a square lattice structure.

The cladding structures, which have been drawn forward in the previous paragraph, have all been based on a fundamental hexagonal shape. However, also other possibilities exist for forming the periodic cladding structured low-index-core fibres, and one such example is the square structure as illustrated in FIG. 22. In this realisation, the voids/rods (27) are centred at the corners of a square lattice structure.

Figure 23:
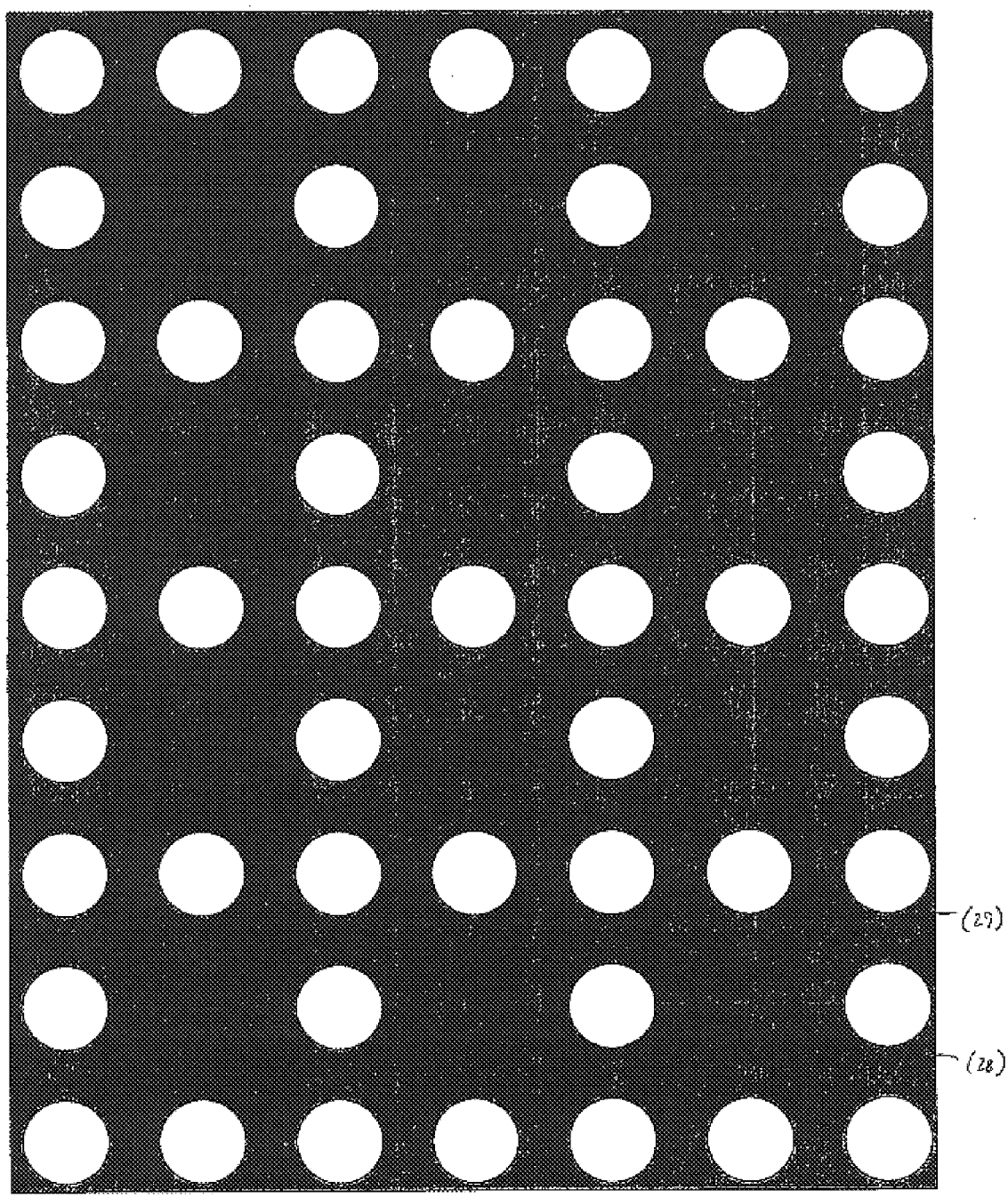
FIG. 23 illustrates a square lattice cladding structure, which has been extended by adding additional voids/rods centred on straight lines between the square corner points.

In FIG. 23, the square structure has been extended by adding additional voids/rods (28) centred on straight lines between the square corner points. Note also that this structure may be seen as a superposition of two square lattice structures, which has been angled 45 degrees relative to each other.

Figure 24:
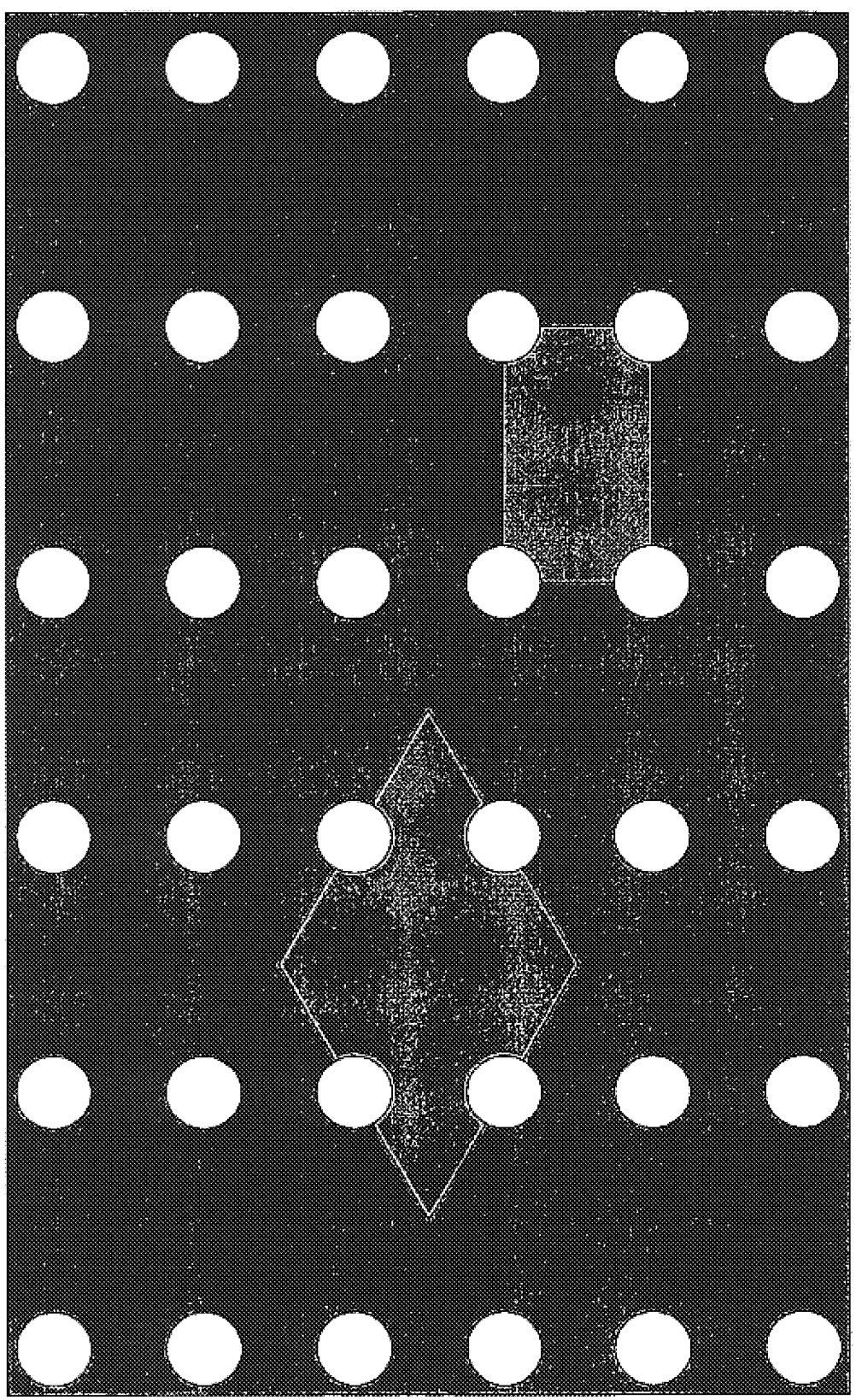
FIG. 24 illustrates an embodiment of a periodic cladding in which the voids/rods are placed in a rectangular lattice structure having two unit cells.

Yet another cladding structure realisation is the rectangular lattice shown in FIG. 24, which may be applied for applications, where two principal main axes (e.g., for polarisation controlling components) are necessary. In agreement with the previous considerations on hexagonal structures, in which different combinations of sub-groups of voids/rods are replacing the original elements in the lattice structure new and improved structures may be obtained by this technique.

Figure 25:
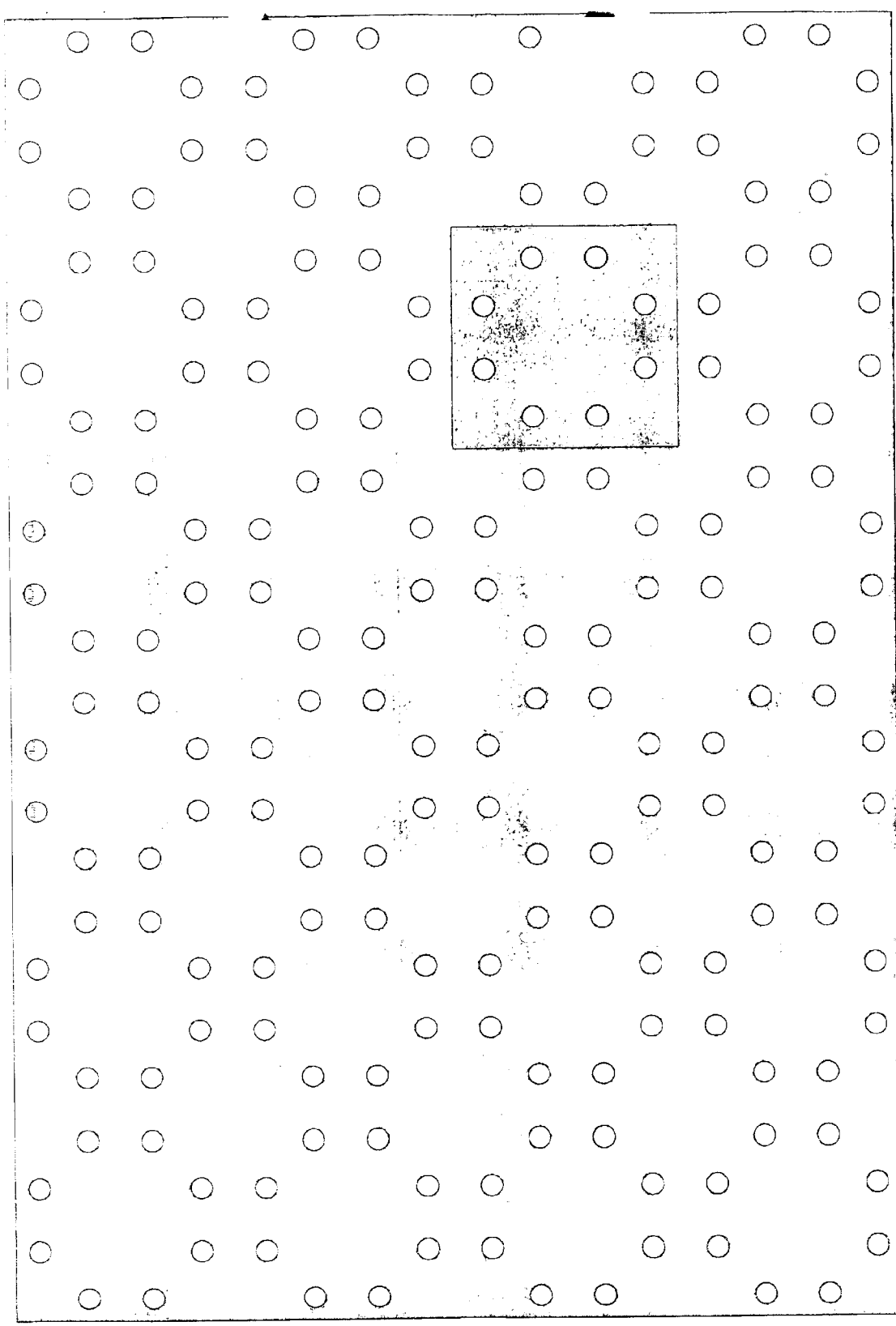
FIG. 25 shows an embodiment of a periodic cladding in which the voids/rods are placed in an octagonal structure. A unit cell is also depicted.

An interesting example is shown in FIG. 25, where an octagonal structure is depicted. The structure may also be viewed as sub-groups of four equal sized voids/rods in a square structure placed in an overall square structure angled by 45 degrees relative to the sub-groups. As it has been mentioned previously, the orientations of the sub-groups may be varied in an infinite number of combinations, forming the basis of designing new waveguiding structured with unique electromagnetic/optic properties that may be tailored to numerous advanced applications.

Figure 26:
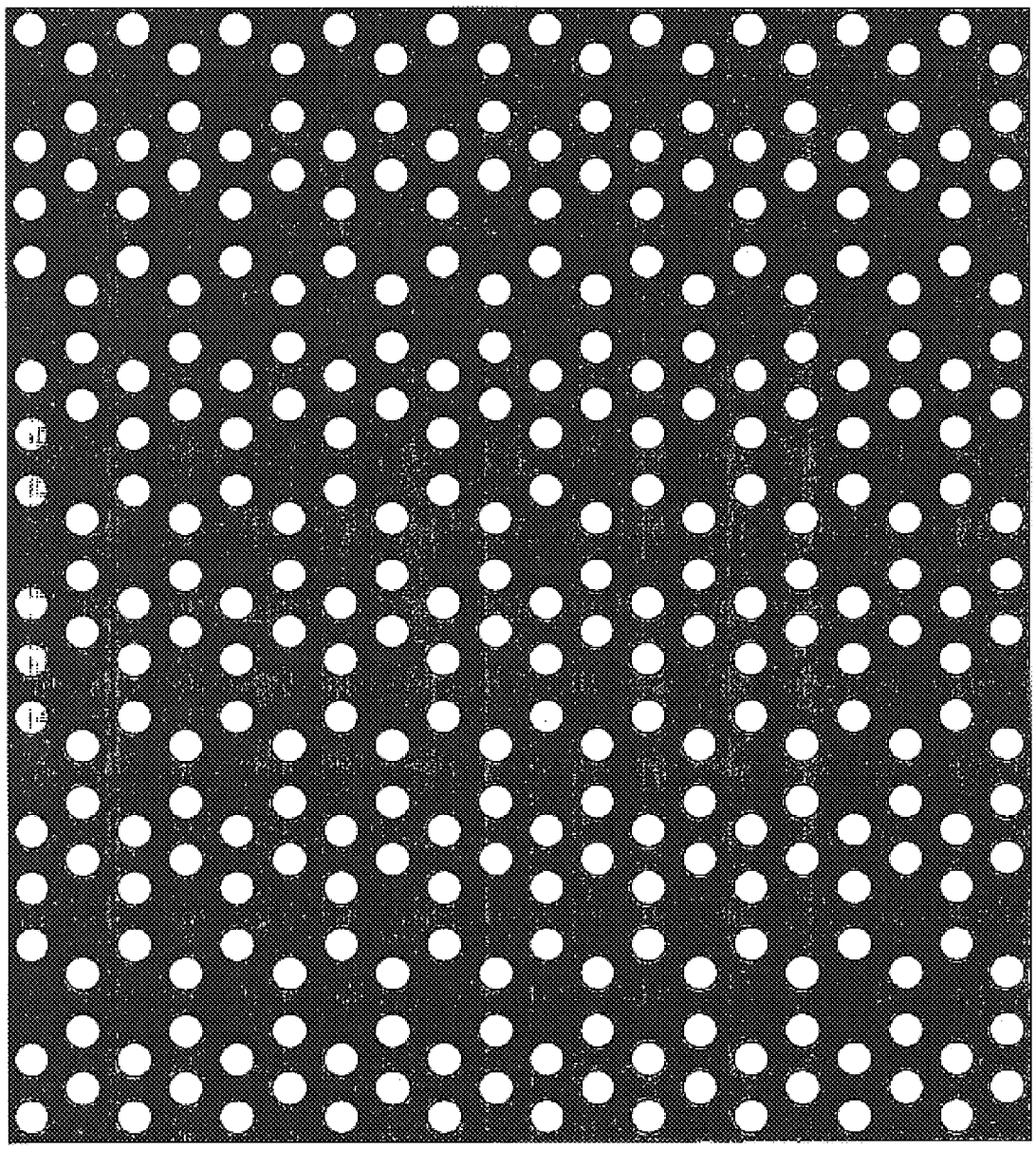
FIG. 26 illustrates an embodiment of a periodic cladding in which triangular and hexagonal elements (sub-groups) have been combined.
Figure 27:
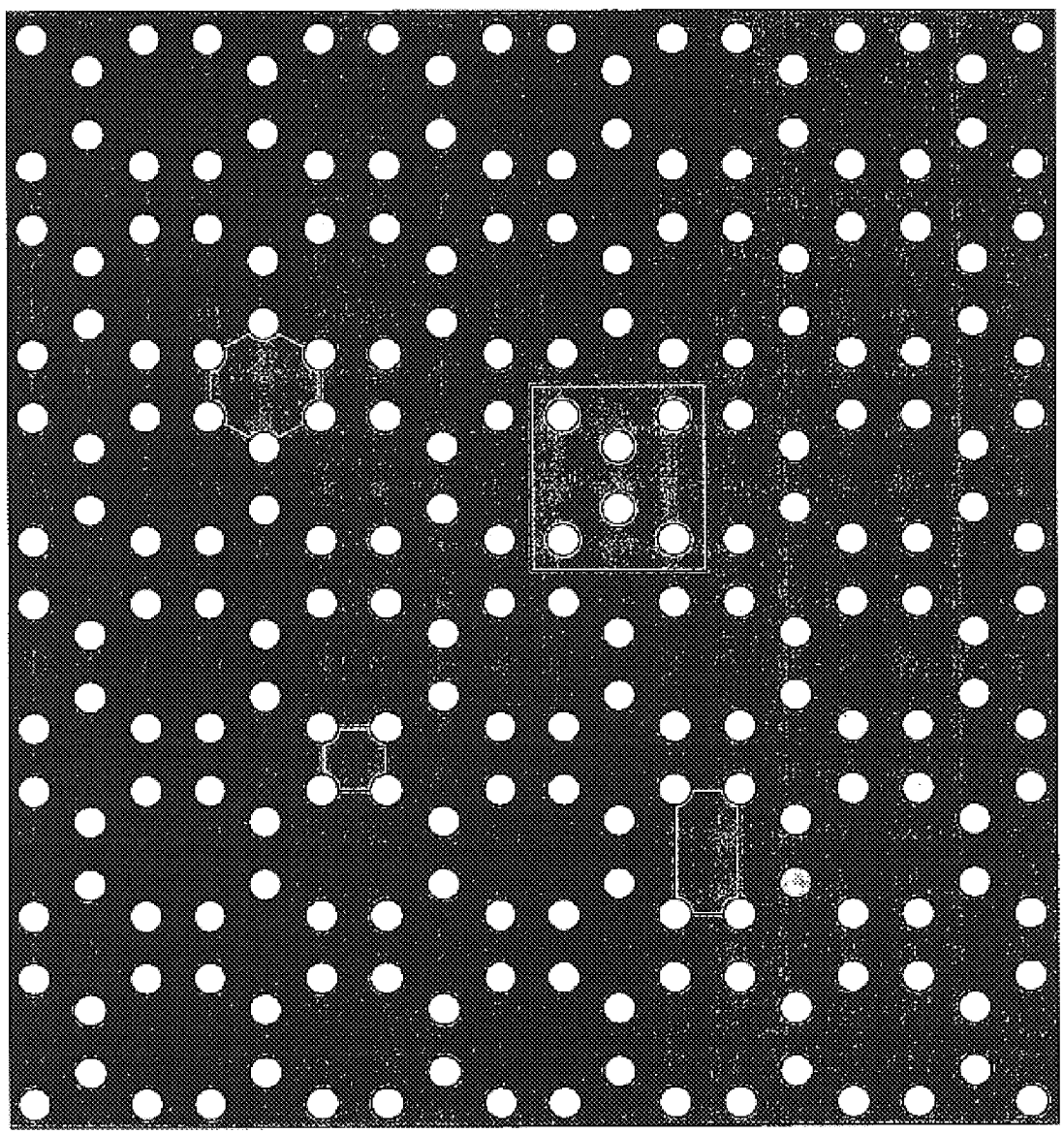
FIG. 27 illustrates an embodiment of a periodic cladding in which a square lattice structure and hexagonal elements (sub-groups) have been combined.

Examples of periodic cladding structures that combines hexagonal and triangular shaped lattice structures are shown in FIG. 26, and in FIG. 27 a combination of square and hexagonal subgroups is illustrated. Other possibilities of applying different parallelograms in the cladding structures are also realistic for optical mode shaping.

All cladding structures previously disclosed, may be combined with various realisations of the core area. The core may be formed by a low refractive index area, which deliberately breaks the symmetry of the cladding, and allows light to be guided along the core by the PSG effect. Thus, the waveguiding effect is fundamentally different from conventional high refractive index waveguiding.

One example of the PCF with low-index core area covered by the present invention has already been illustrated in FIG. 6, in which a low-index defect has been introduced as an additional void/hole centrally placed in one of the Honeycomb structure cells.

Figure 28:
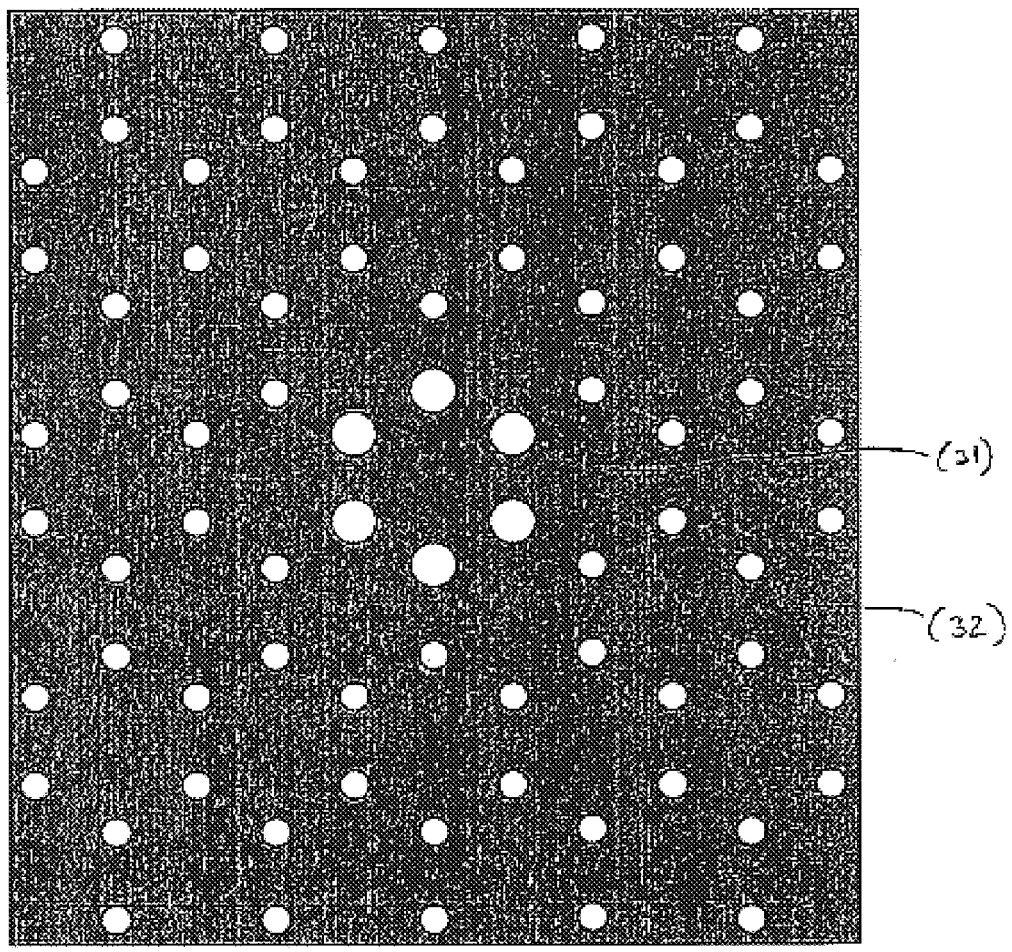
FIG. 28 schematic illustration of a fibre/waveguide core area and the closest Honeycomb cladding surroundings. The core region is formed by a single Honeycomb cell with larger hole sizes.

Another example of a defect (or core) area that may serve as a low-index core area is illustrated in FIG. 28. In this structure, the larger diameter of the voids forming the core area (31) ensures that the optical mode field is confined around the core and only to a limited extent penetrates into the cladding cells (32). The advantage of this realisation of the core area is that the mode field in this case will be concentrated in the centre of the core defect area, where glass or even materials with high non-linear coefficients may be placed for applications were strong non-linearities are relevant.

Figure 29:
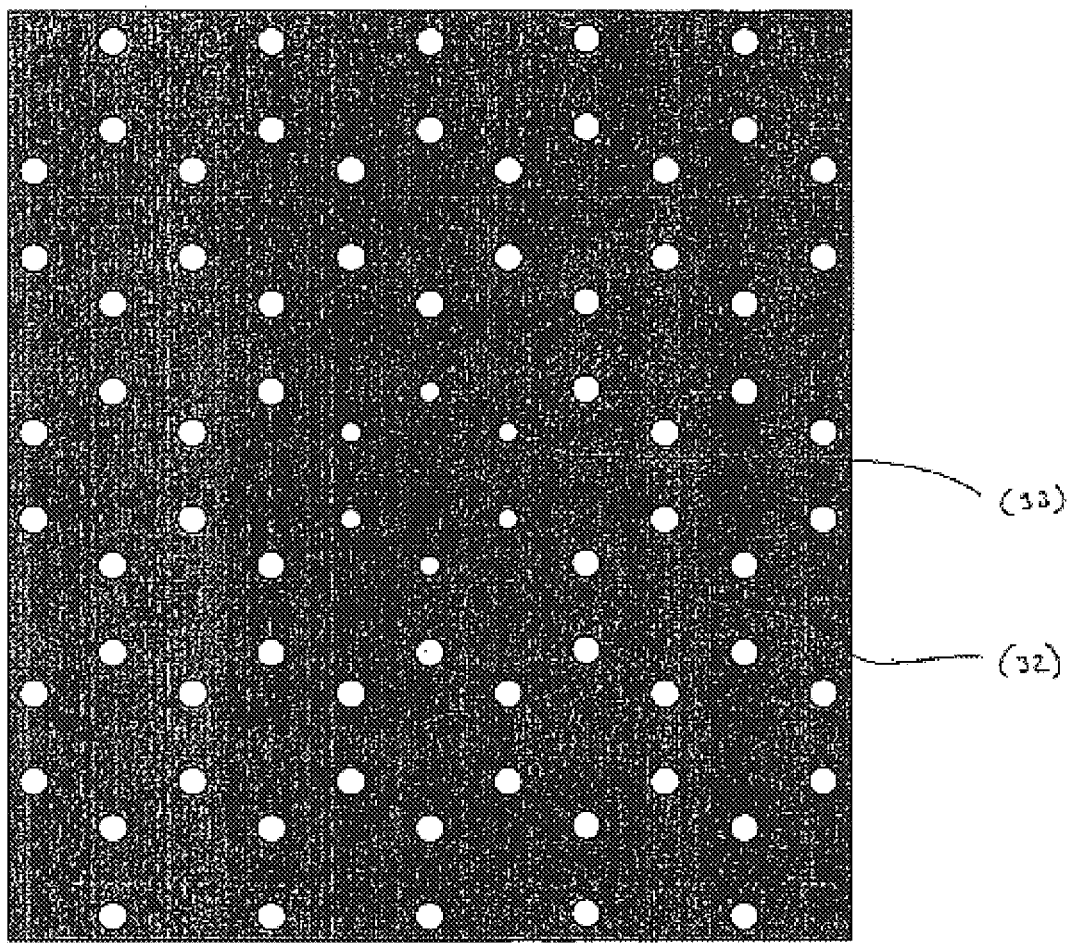
FIG. 29 schematic illustration of a fibre/waveguide core area and the closest Honeycomb cladding surroundings. The core region is formed by a single Honeycomb cell with smaller hole size.

Yet another realisation of the formation of the core defect without adding a central void in one of the Honeycomb cells, is illustrated in FIG. 29, where the core forming voids (33) are of smaller diameter than the cladding cell voids (32). It should also be noted that other defects (or core areas) could be formed by interchanging the voids in the core region with voids of other dimensions, in such a way that the core cell is formed by voids of different diameters.

Figure 30:
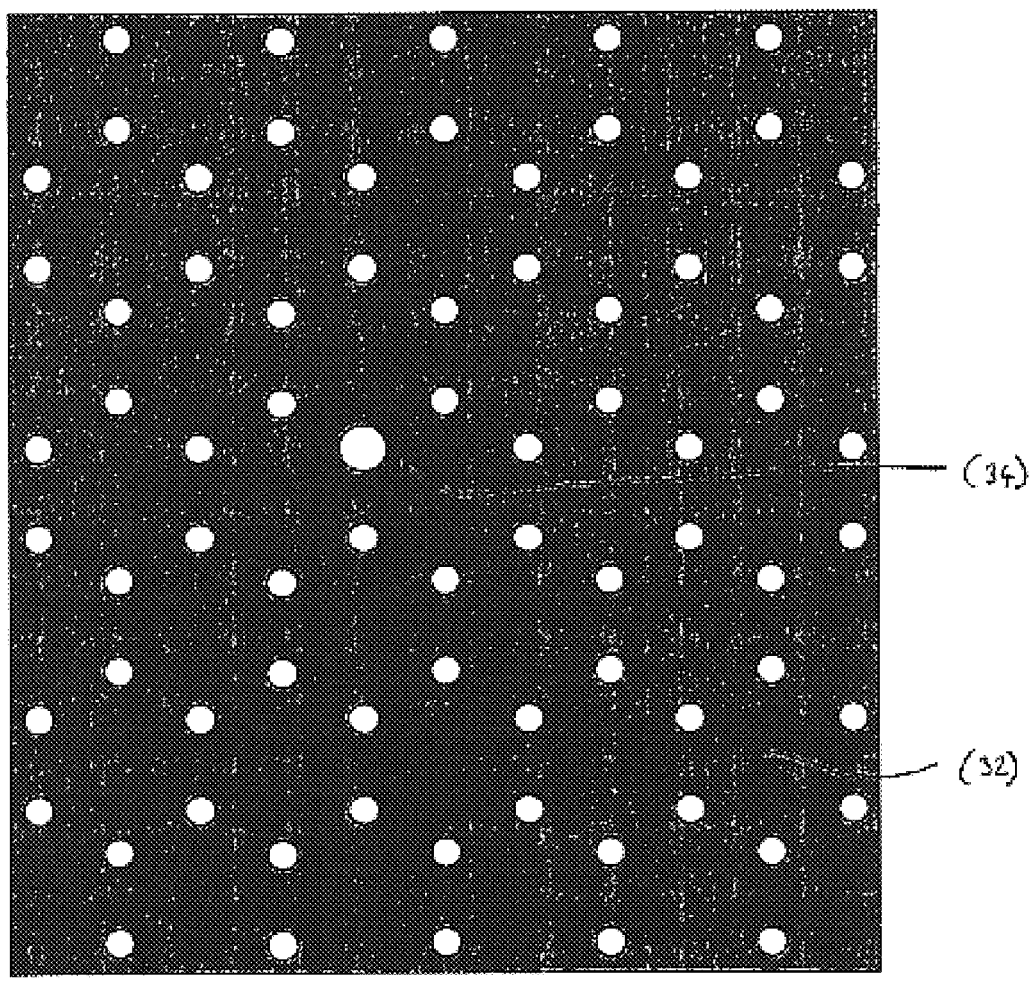
FIG. 30 schematic illustration of a fibre/waveguide core area and the closest Honeycomb cladding surroundings. The core region is formed by a single void with larger hole size.

Such realisations are exemplified in FIG. 30, where an asymmetric core cell (34) is shown. Such an approach may exhibit specifically interesting properties with respect to the implementation of polarisation maintaining fibres. In FIG. 30, the core is formed by placing one void with a larger cross-sectional area in an otherwise periodic Honeycomb structure.

Figure 31:
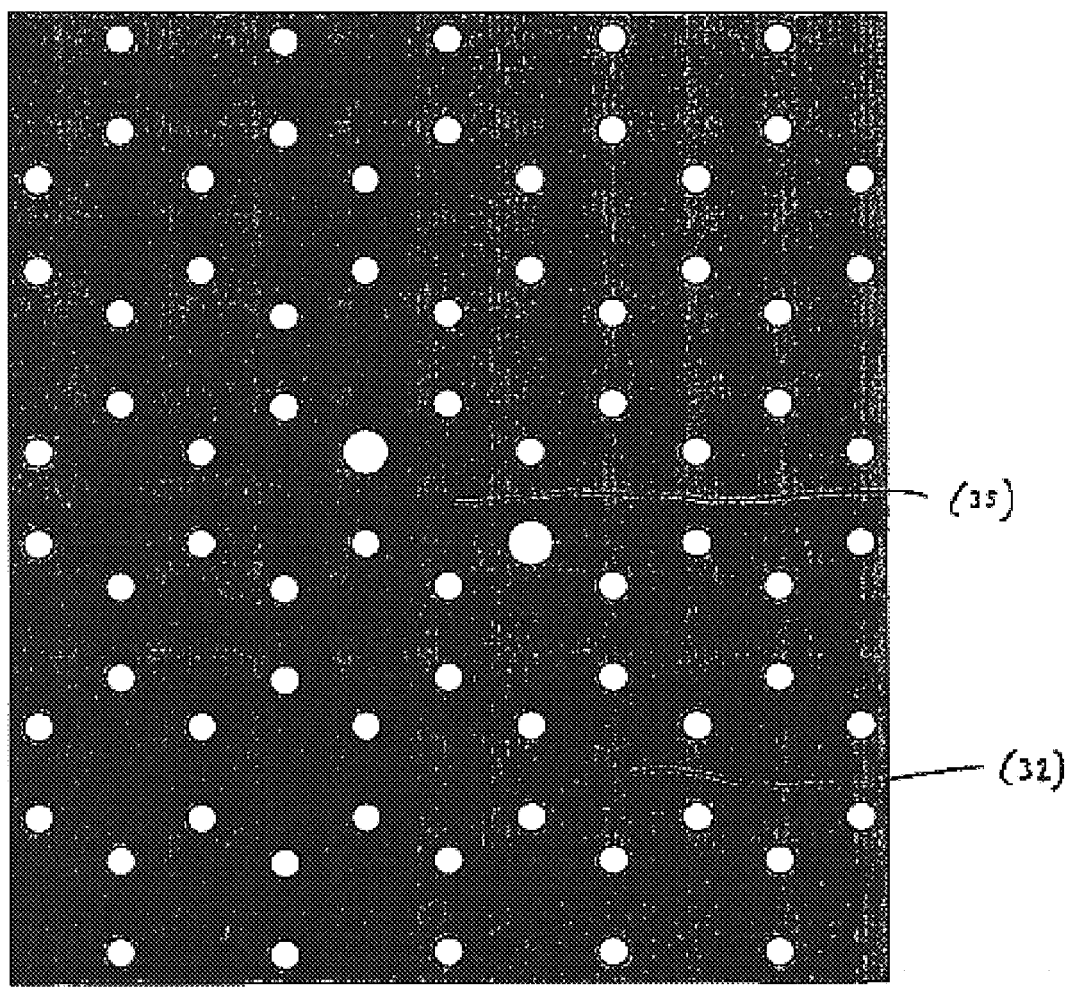
FIG. 31 schematic illustration of a fibre/waveguide core area and the closest Honeycomb cladding surroundings. The core region is formed by two voids with larger hole sizes.

A further step is to add more than one void of different dimensions in what is going to be the defect (or core) area, and such an example is shown in FIG. 31, where two larger holes is placed in opposite corners of a Honeycomb cell (35).

Figure 32:
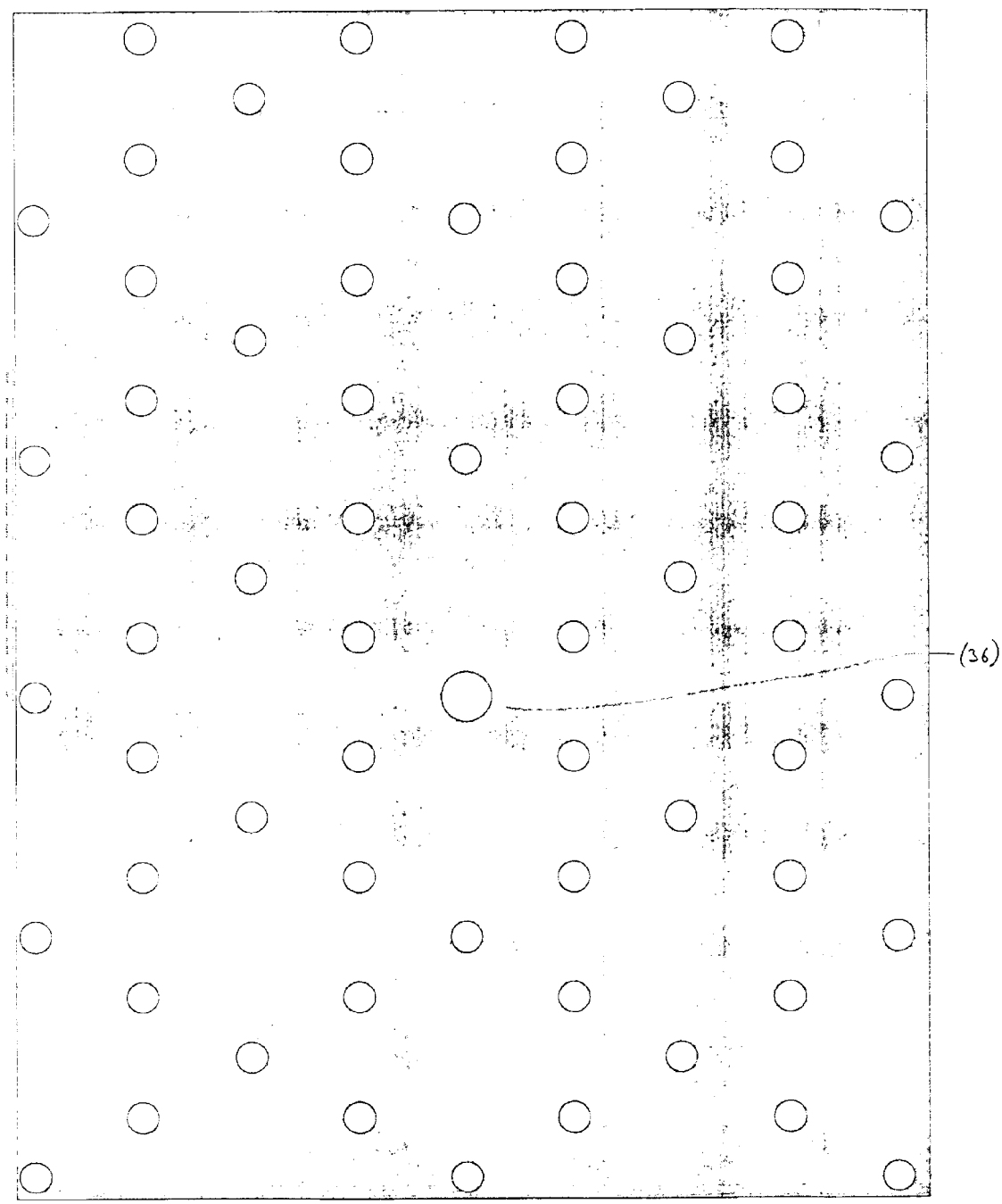
FIG. 32 schematic illustration of a fibre/waveguide core area and the closest Kagomé cladding surroundings. The core region is formed by a single void with larger hole size.

Another example of a defect created by a single void (36) of different (here larger) cross-sectional area than the cladding forming voids, is shown in FIG. 32, where a single low-index void has been introduced in a Kagomé cladding structure.

Figure 33:
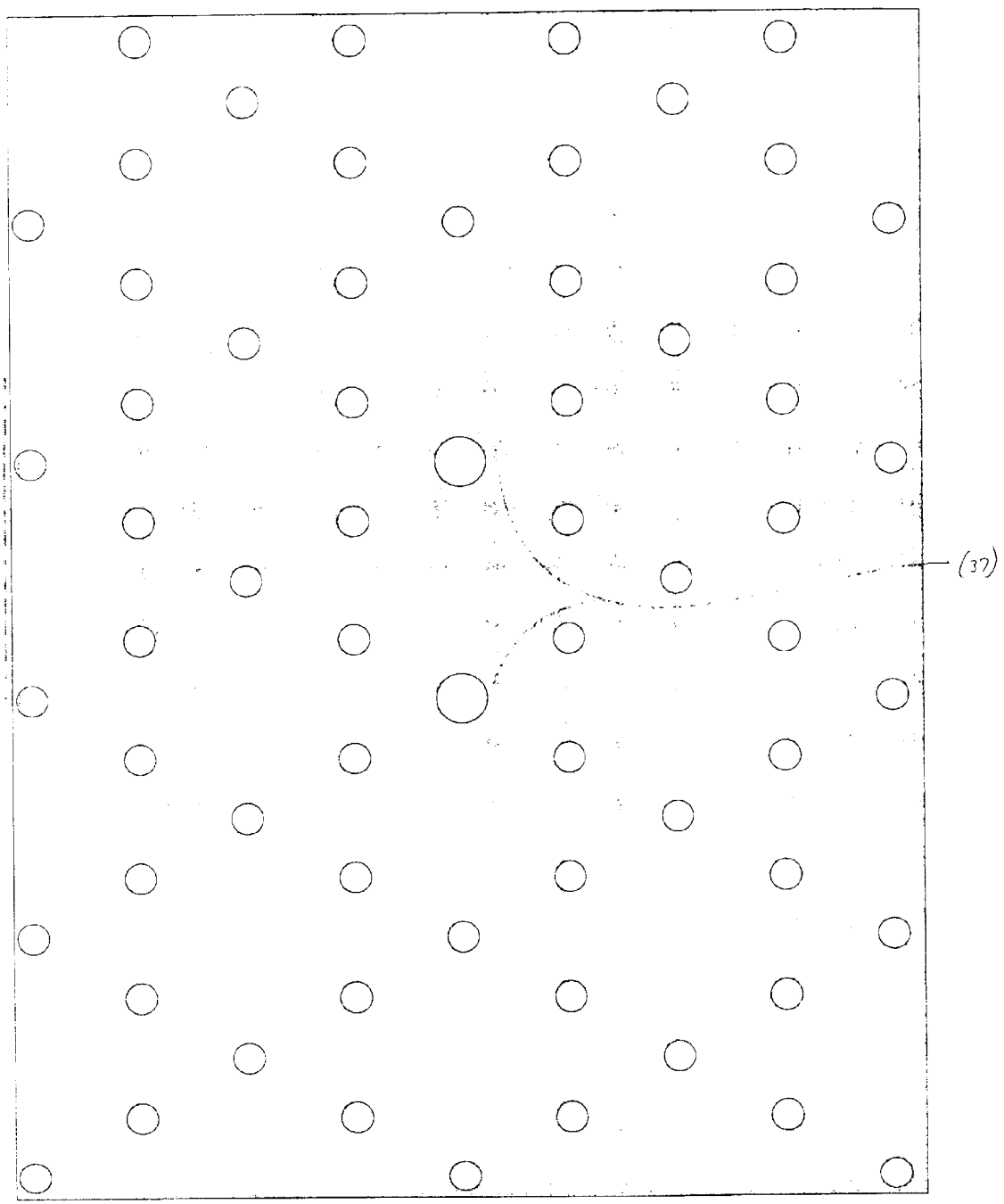
FIG. 33 schematic illustration of a fibre/waveguide core area and the closest Kagomé cladding surroundings. The core region is formed by two voids with larger hole sizes.

Similar to the Honeycomb lattice structures, one or more voids having a larger cross sectional area may be introduced into the Kagomé structures. Such an example is shown in FIG. 33 using two enlarged voids (37).

Figure 34:
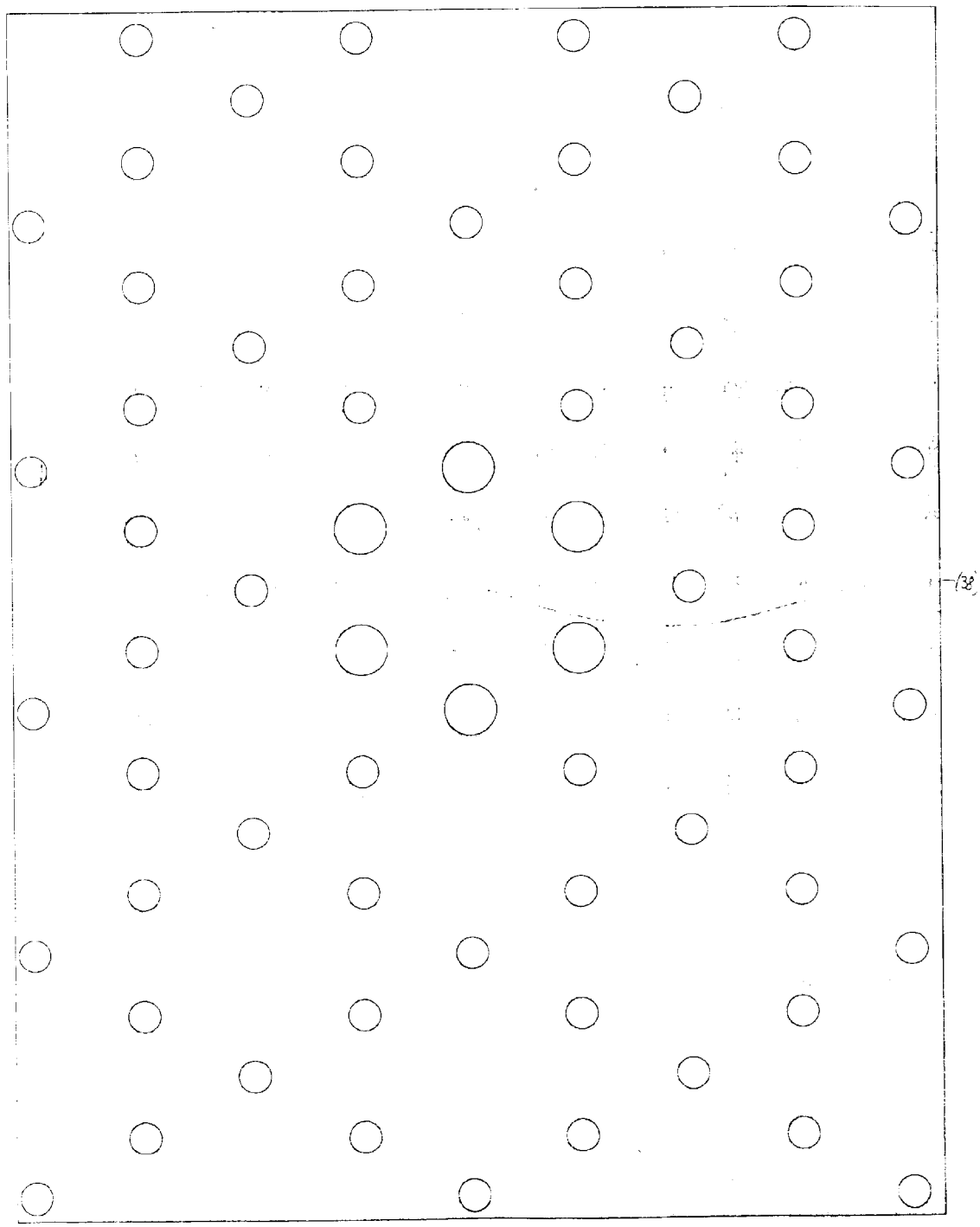
FIG. 34 schematic illustration of a fibre/waveguide core area and the closest Kagomé cladding surroundings. The core region is formed by a single hexagonal cell with larger hole size.
Figure 35:
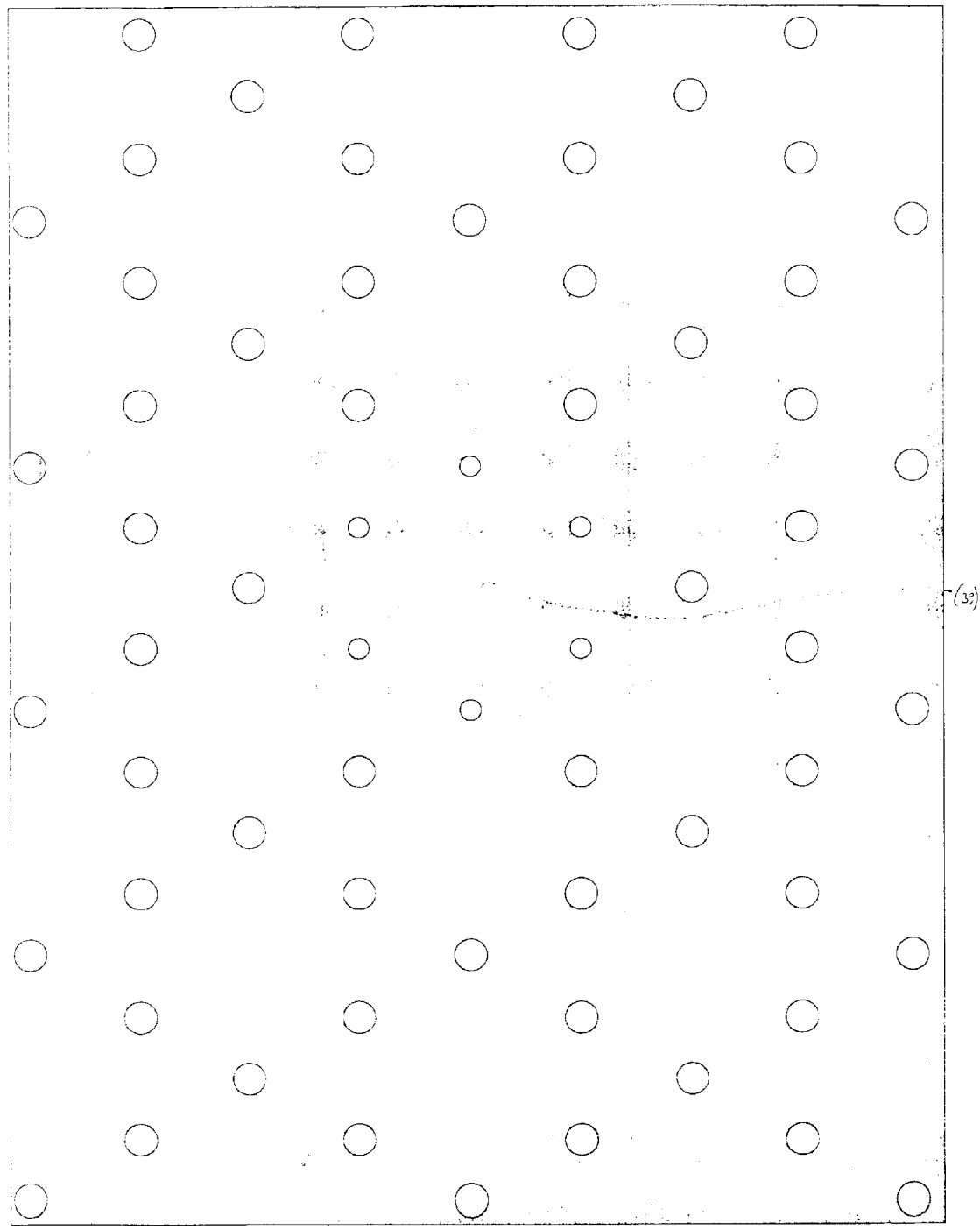
FIG. 35 schematic illustration of a fibre/waveguide core area and the closest Kagomé cladding surroundings. The core region is formed by a single hexagonal cell with smaller hole size.

The Kagomé cladding structure naturally also opens the possibility of forming defects by replacing a group of voids in a hexagonal core cell. In FIG. 34 all six voids (38) forming the core cell have been enlarged, whereas the same six voids (39) have been reduced in size as exemplified in FIG. 35.

Depending on the desired performance, it is naturally possible to further increase the number of voids with larger dimensions than the cladding structure forming voids. Fundamentally, the core defect area may be made up by holes of variable size only ensuring that a located core (or defect) mode may be located around the core cells. It will also be possible to create a defect by introducing a single (or a few) void(s) with a cross section that deviates significantly from the other voids forming the cladding structure, even though the different voids have the same cross-sectional areas. Note also that this way of creating defects by locally modifying the lattice-forming voids can be applied on all the different described cladding structures. Note also, that although the presented examples have been made for voids/rods with circular cross sections, the present invention is not limited to these. Triangular, squared and higher order polygons or distorted polygons are also included as well as other shapes such as elliptic and asymmetric polygons.

Figure 36:
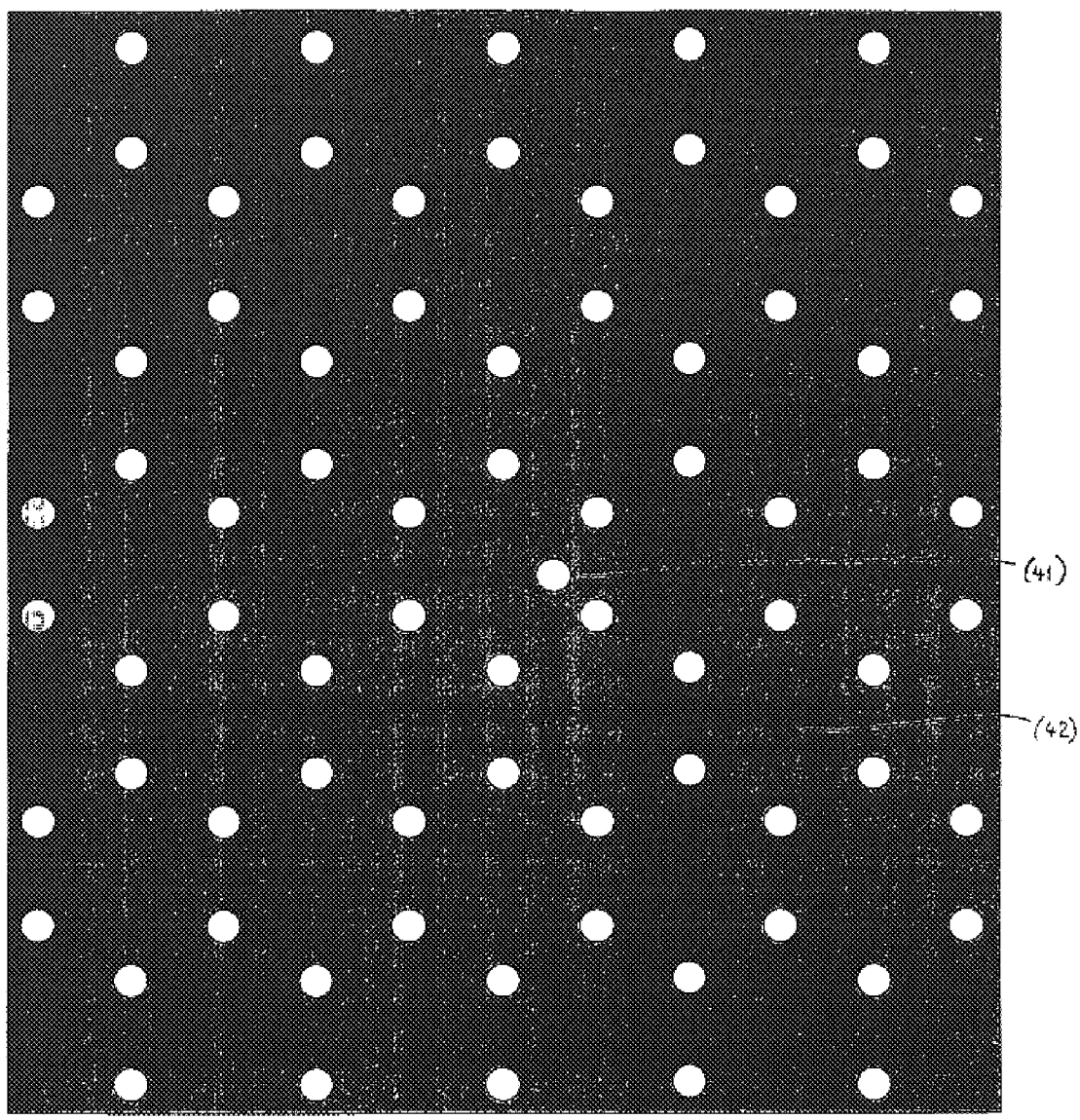
FIG. 36 shows an asymmetric position of a defect void surrounded by periodic Honeycomb cells.
Figure 32:
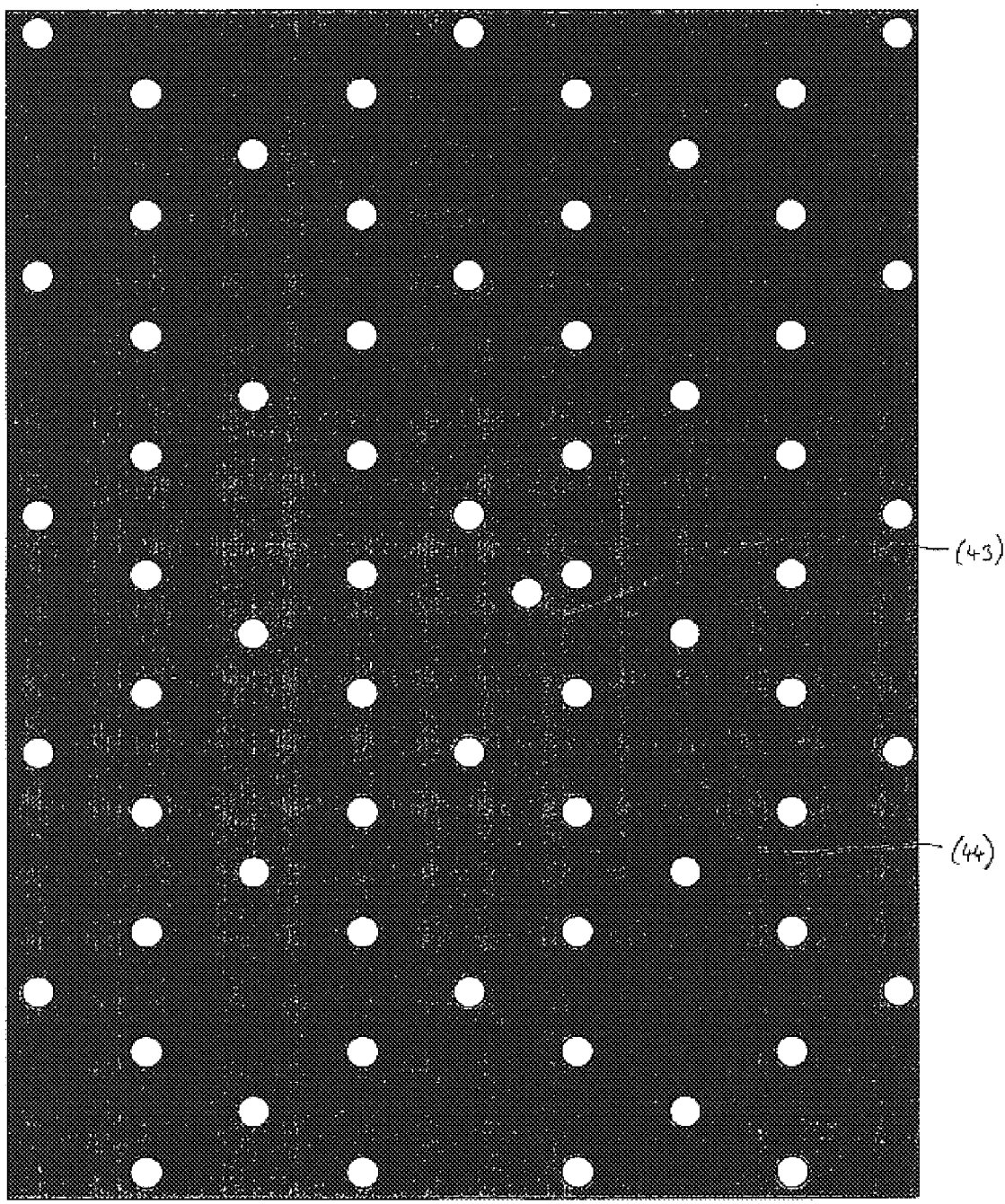

As previously described, core regions may be formed by the introduction of a low-index void placed in one of the cells of the cladding, whereby this specific defect cell becomes able to guide light prohibited by the periodicity of the periodic cladding. However, the additional void does not necessarily have to be placed centrally in the core cell, but it may also be placed in an asymmetrical position as illustrated in FIG. 36, where a defect void (41) is placed away from the centre of the core cell, which in this example is surrounded by periodic Honeycomb cells (42).

In FIG. 37 a similar example using an asymmetrically placed additional hole (43) is presented for a Kagomé cladding cell structure (44). Such placement of the void in the core cell may be used for special mode field shaping for example in cases, where specific in- and out-coupling properties have to be fulfilled.

Figure 38:
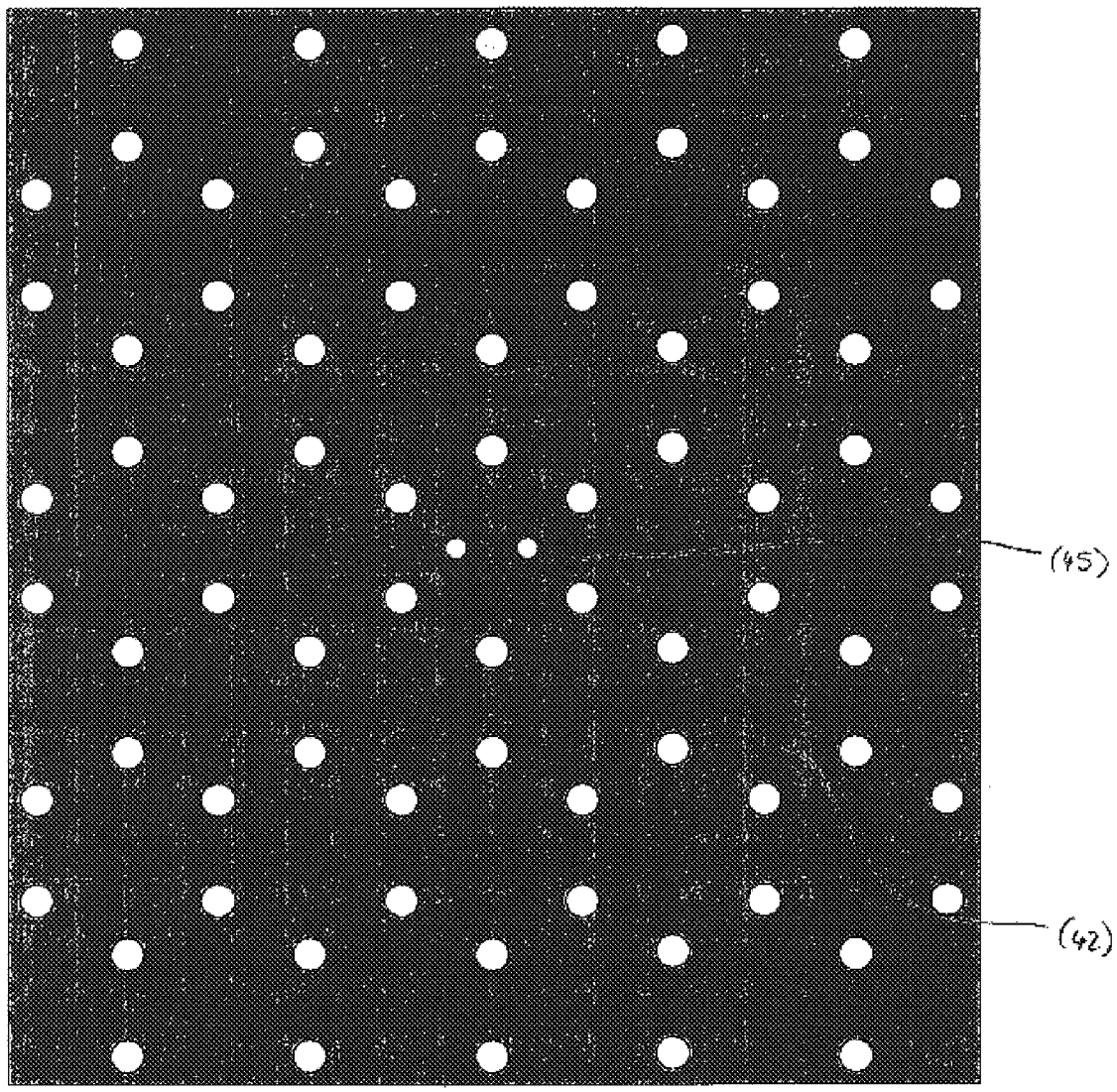
FIG. 38 shows an example, where the defect is formed by two voids with smaller diameters than the voids defining the vertices of the Honeycomb cladding cells.

Another example of a more complex design of the core region, is shown in FIG. 38, where the defect is formed by two voids (45) with smaller diameters than the voids forming the Honeycomb cladding cells (42).

Figure 39:
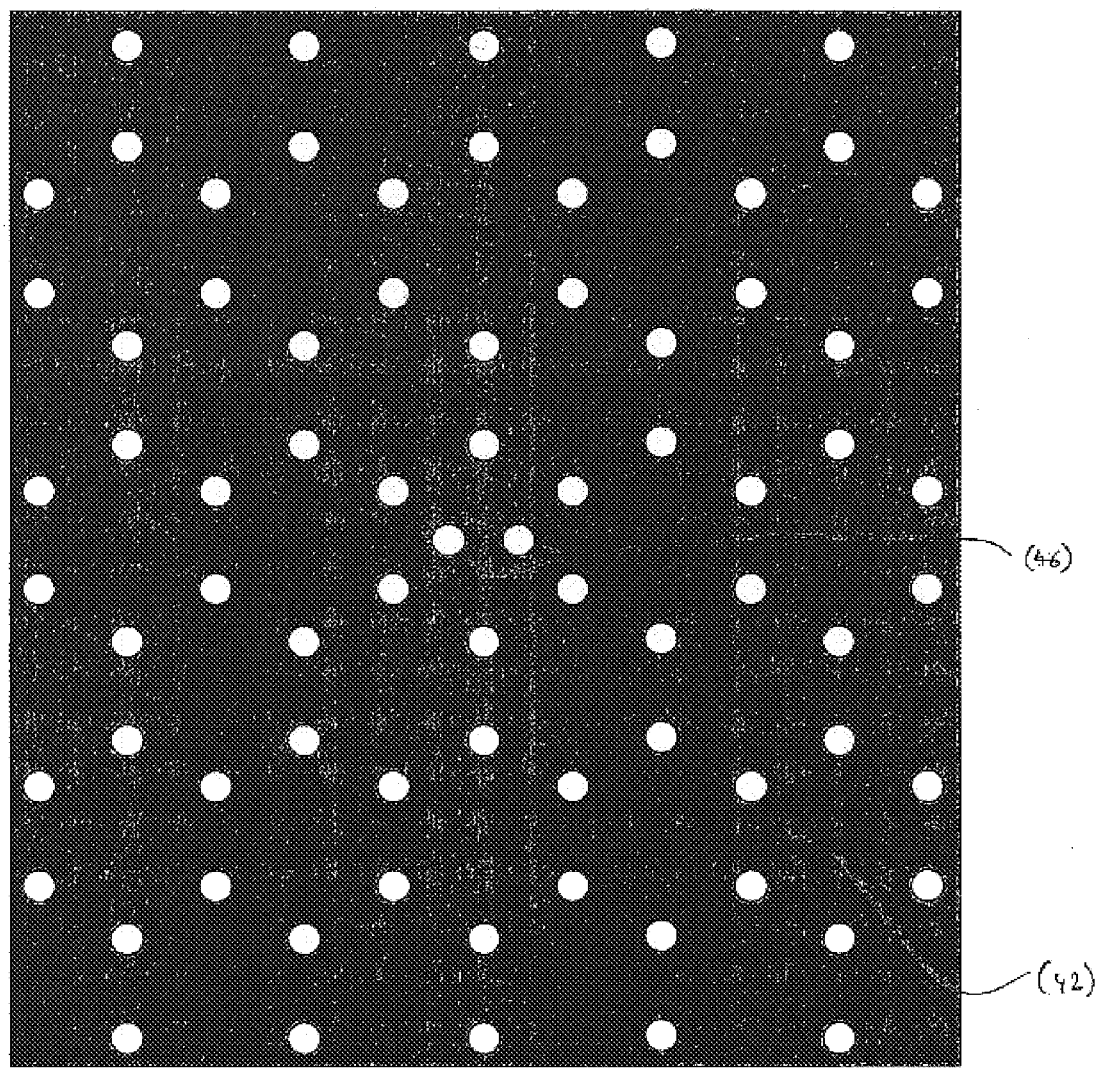
FIG. 39 shows an example, where the defect is formed by two voids having the same diameter as the voids defining the vertices of the Honeycomb cladding cells.
Figure 40:
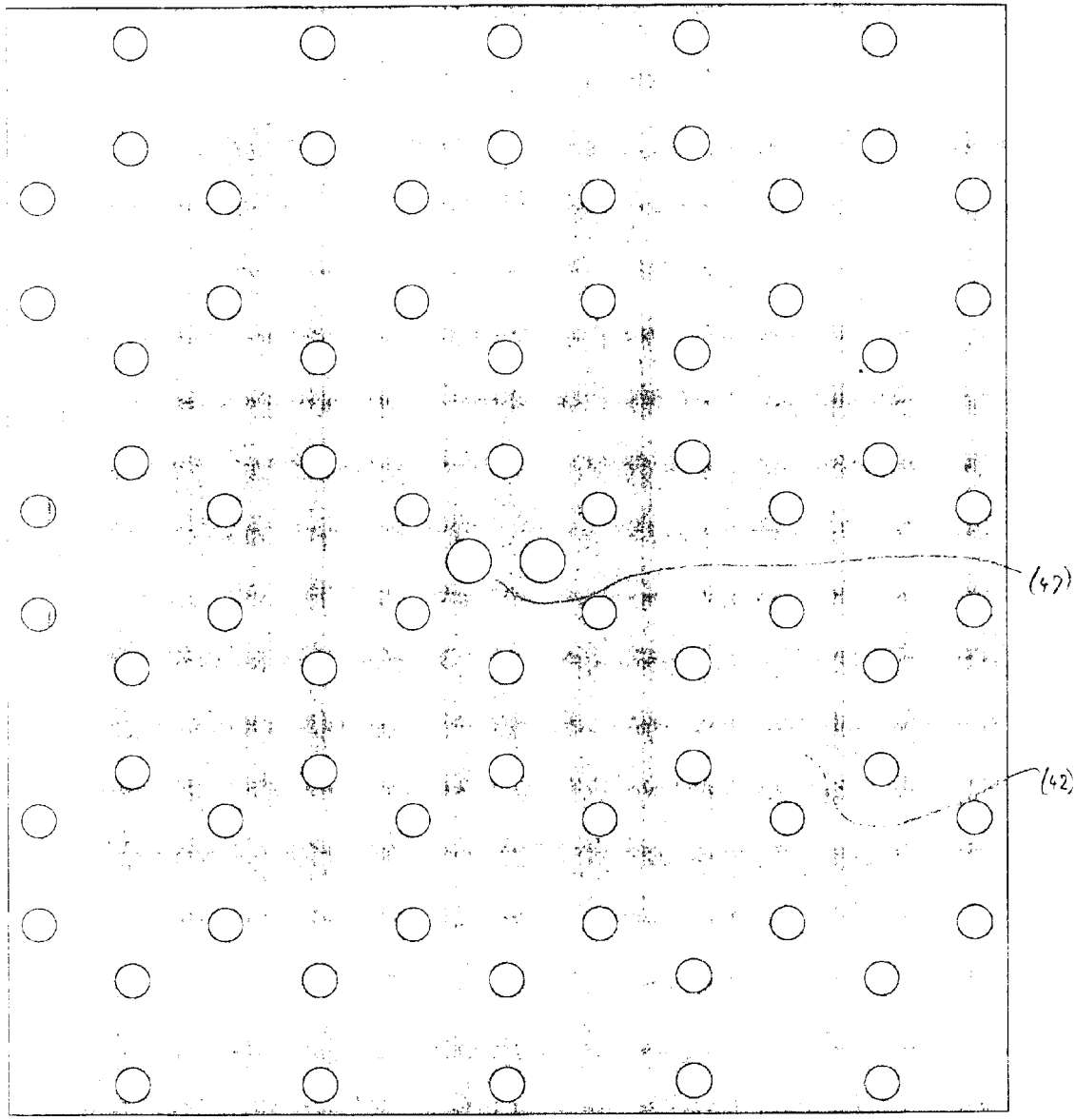
FIG. 40 shows an example, where the defect is formed by two voids with larger diameters than the voids defining the vertices of the Honeycomb cladding cells.
Figure 41:
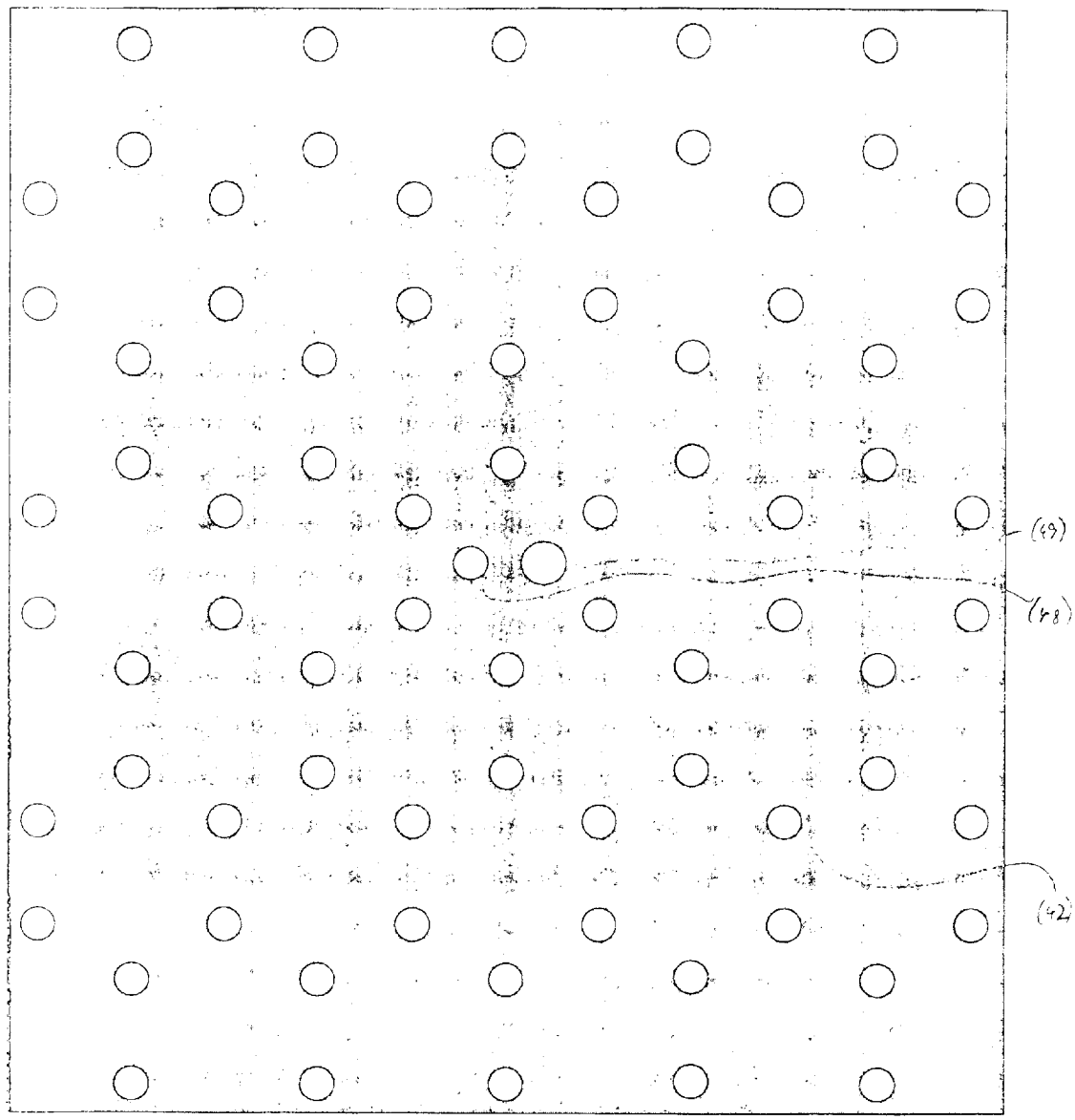
FIG. 41 shows two voids in the core cell, one void with dimensions as the voids defining the vertices of the Honeycomb cladding call and the other void having larger dimensions.

The voids in the core region (46) of the fibre may also, as illustrated in FIG. 39, be of the same dimensions as the cladding cell forming voids, or they may be of larger dimensions as the voids (47) illustrated in FIG. 40. Again, it must be noted that the defect forming voids in the core region does not have to be of equal size, and in the example of two voids in the core cell, one void (48) may be of dimensions as the voids forming the cladding cell (42) and the other (49) may be of larger dimensions as shown in FIG. 41.

Figure 42:
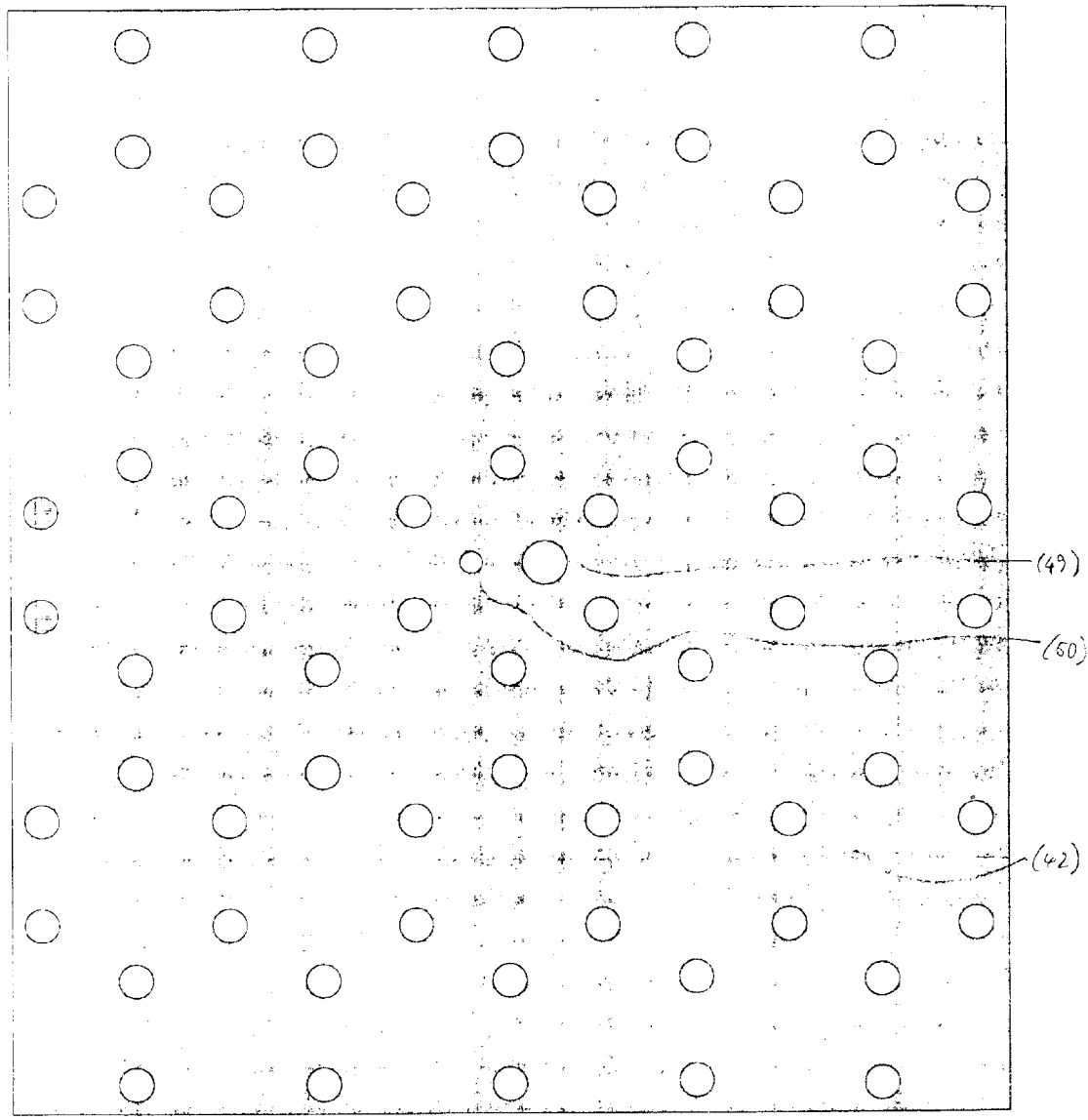
FIG. 42 shows two voids in the core cell, one void with diameters smaller than the voids defining the vertices of the Honeycomb cladding cell and the other void having larger dimensions.
Figure 43:
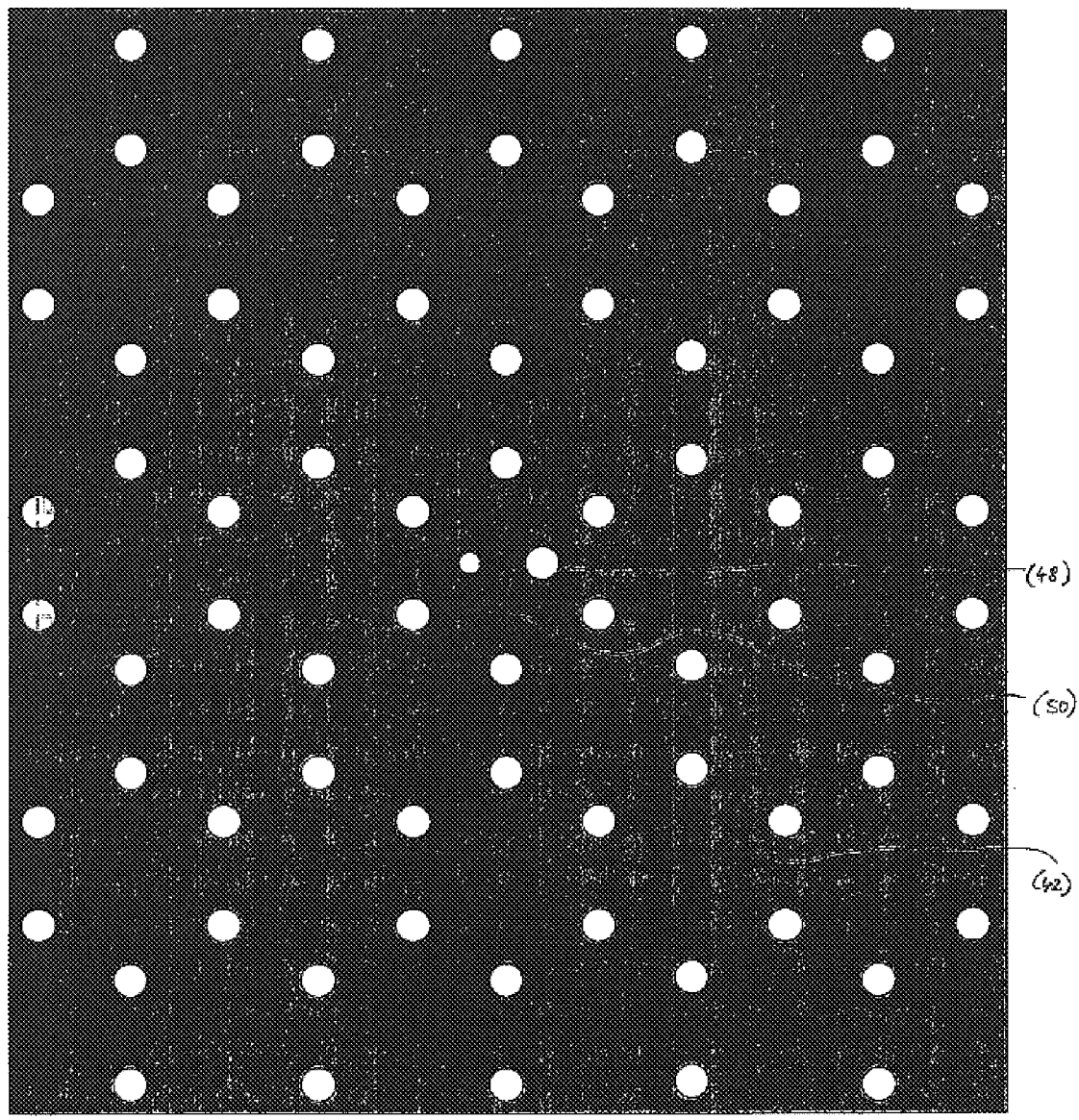
FIG. 43 shows two voids in the core cell, one void with dimensions as the voids defining the vertices of the Honeycomb cladding cell and the other void having smaller dimensions.
Figure 44:
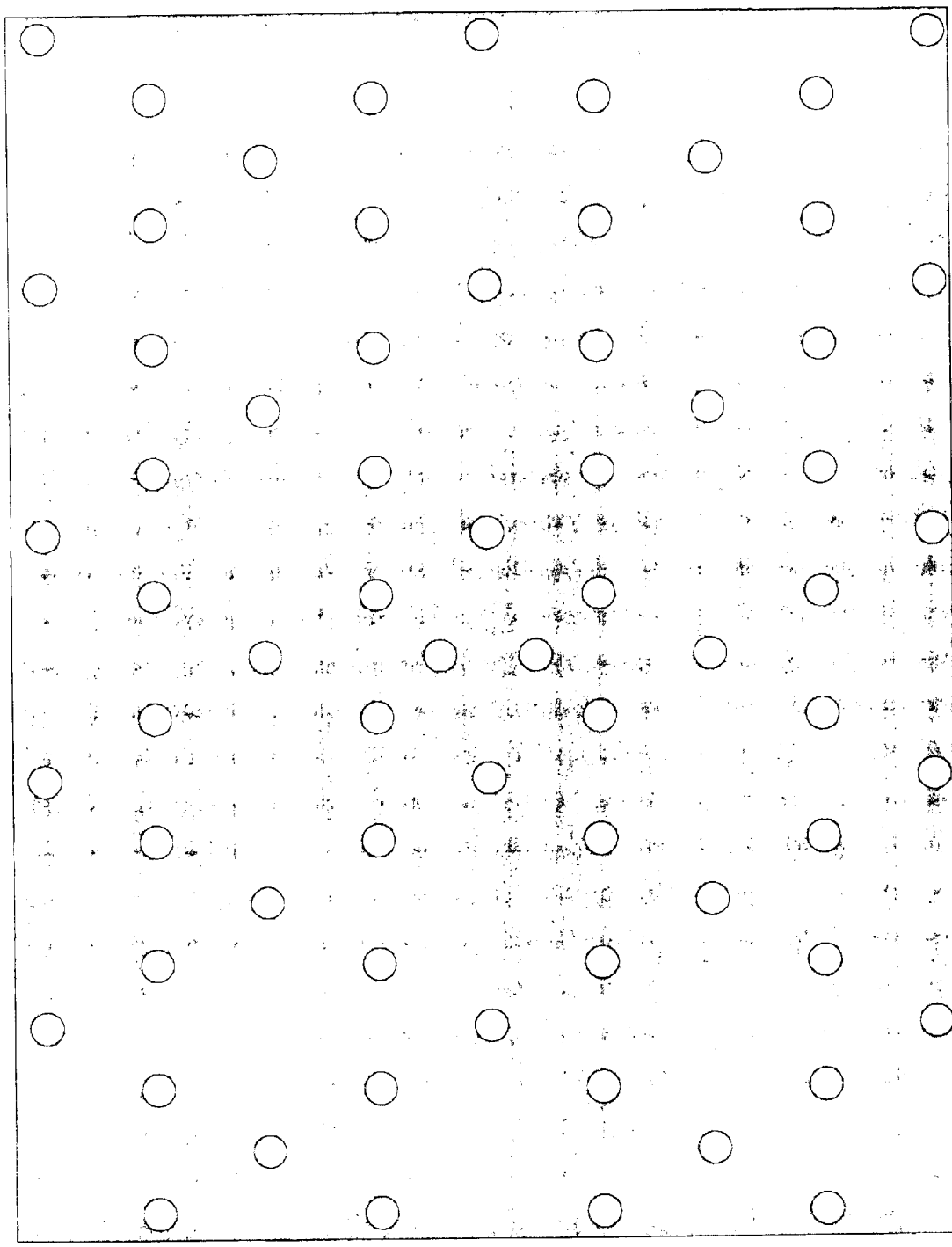
FIG. 44 shows two voids in the core cell, both voids having dimensions as the voids defining the vertices of the Kagomé cladding call.
Figure 45:
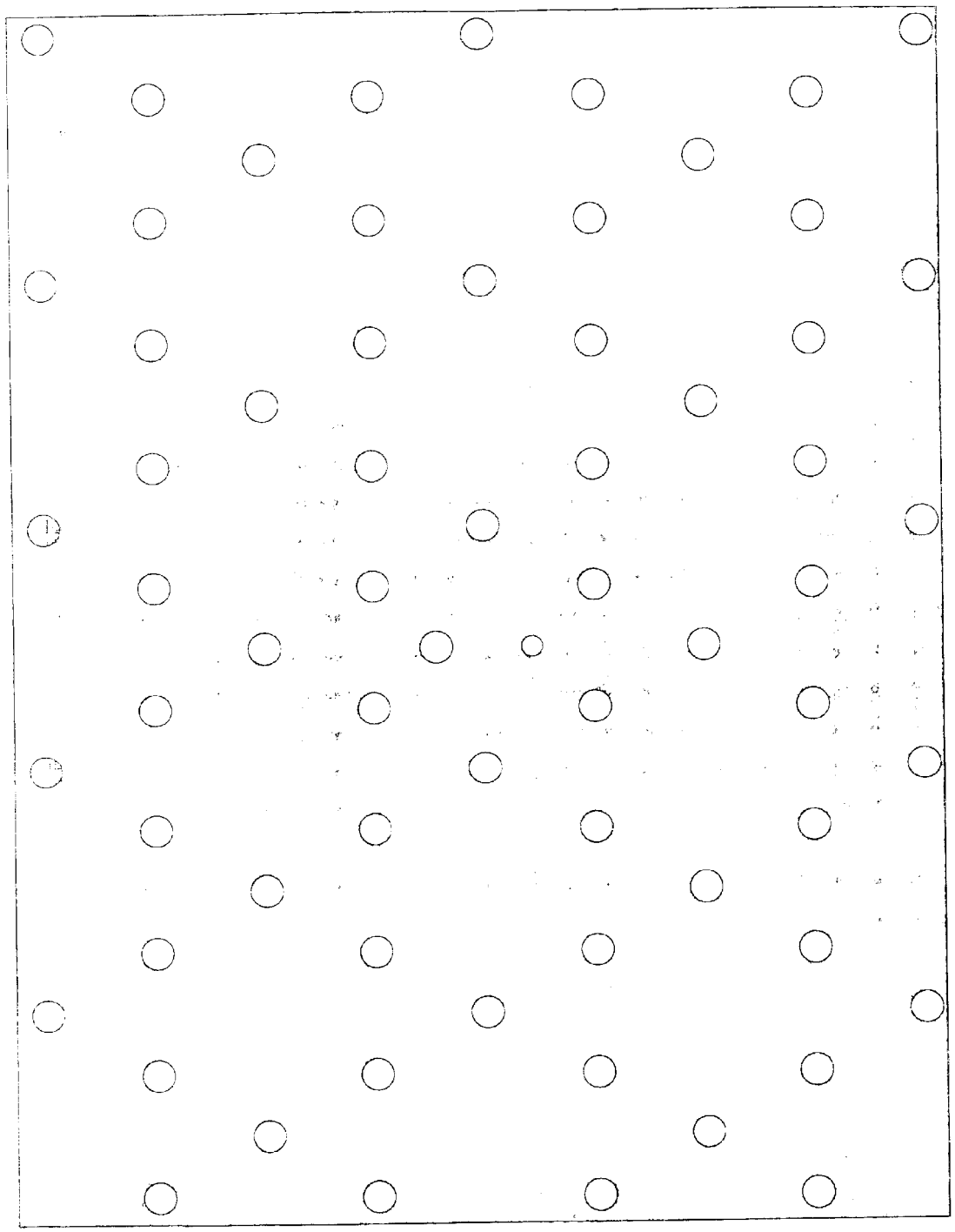
FIG. 45 shows two voids in the core cell, one void with dimensions as the voids defining the vertices of the Kagomé cladding call and the other void having smaller dimensions.
Figure 46:
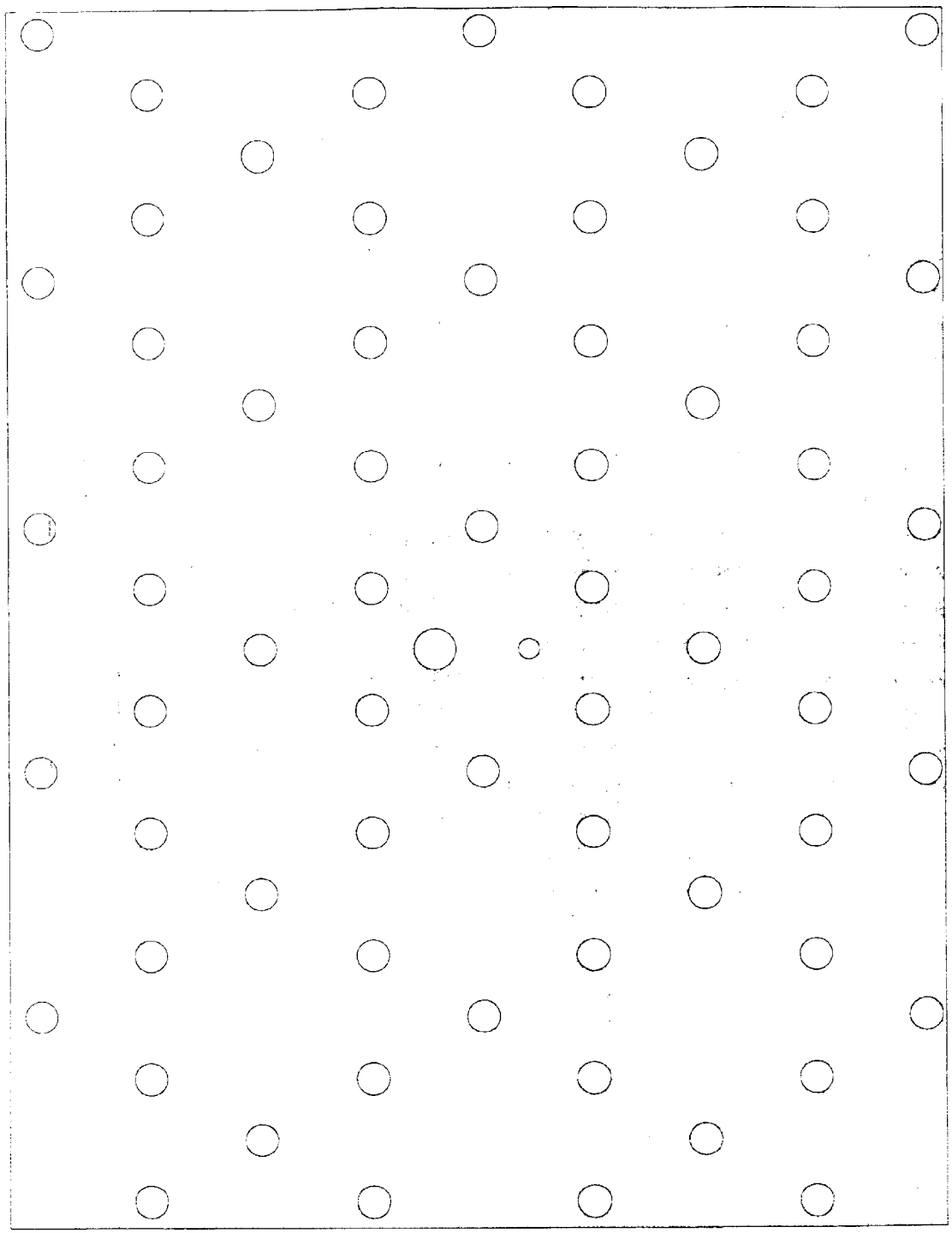
FIG. 46 shows two voids in the core cell, one void with dimensions smaller than the voids defining the vertices of the Kagomé cladding cell and the other void having larger dimensions.
Figure 42:
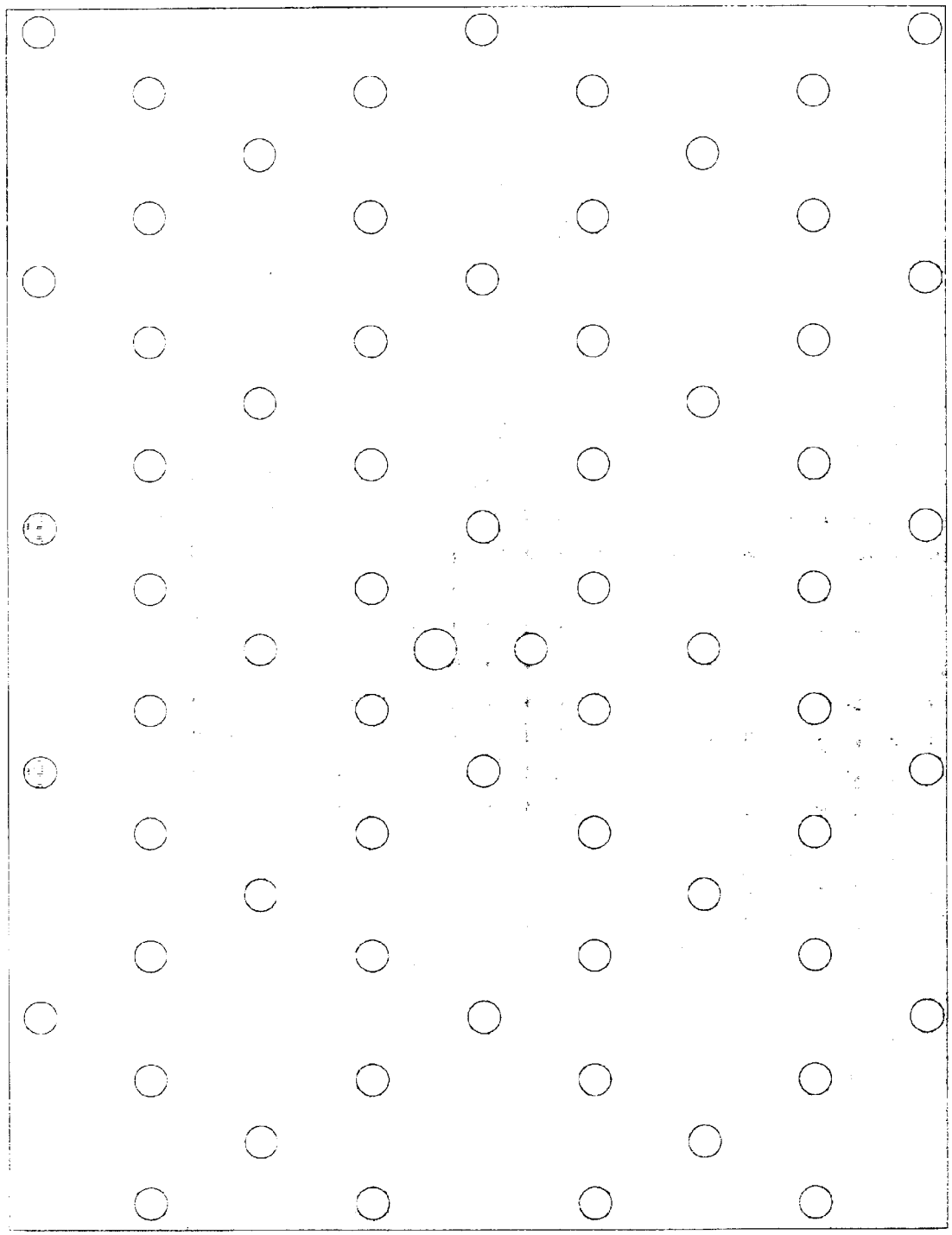
Figure 48:
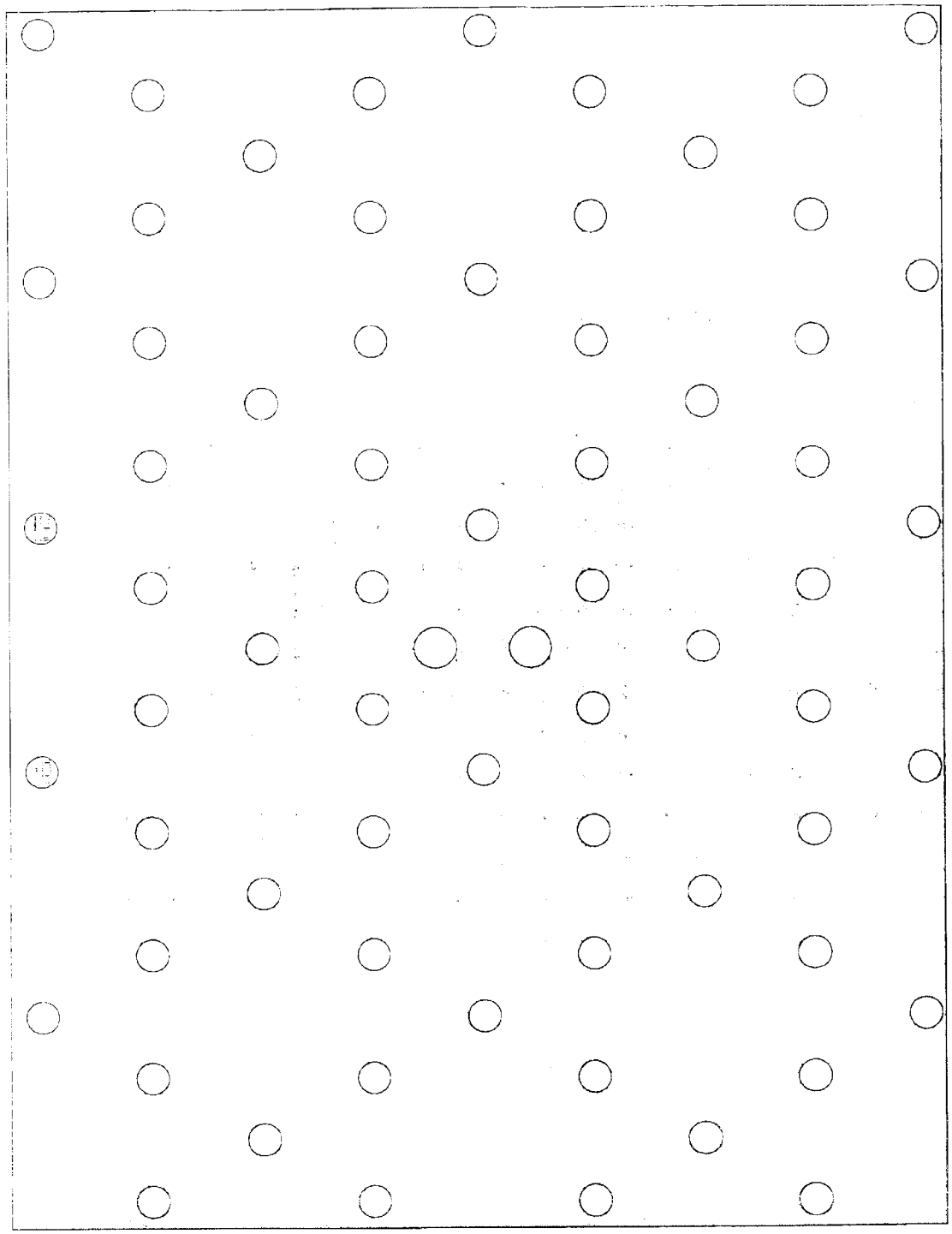
FIG. 48 shows two voids in the core cell, both voids having dimensions larger than the voids defining the vertices of the Kagomé cladding cell.
Figure 49:
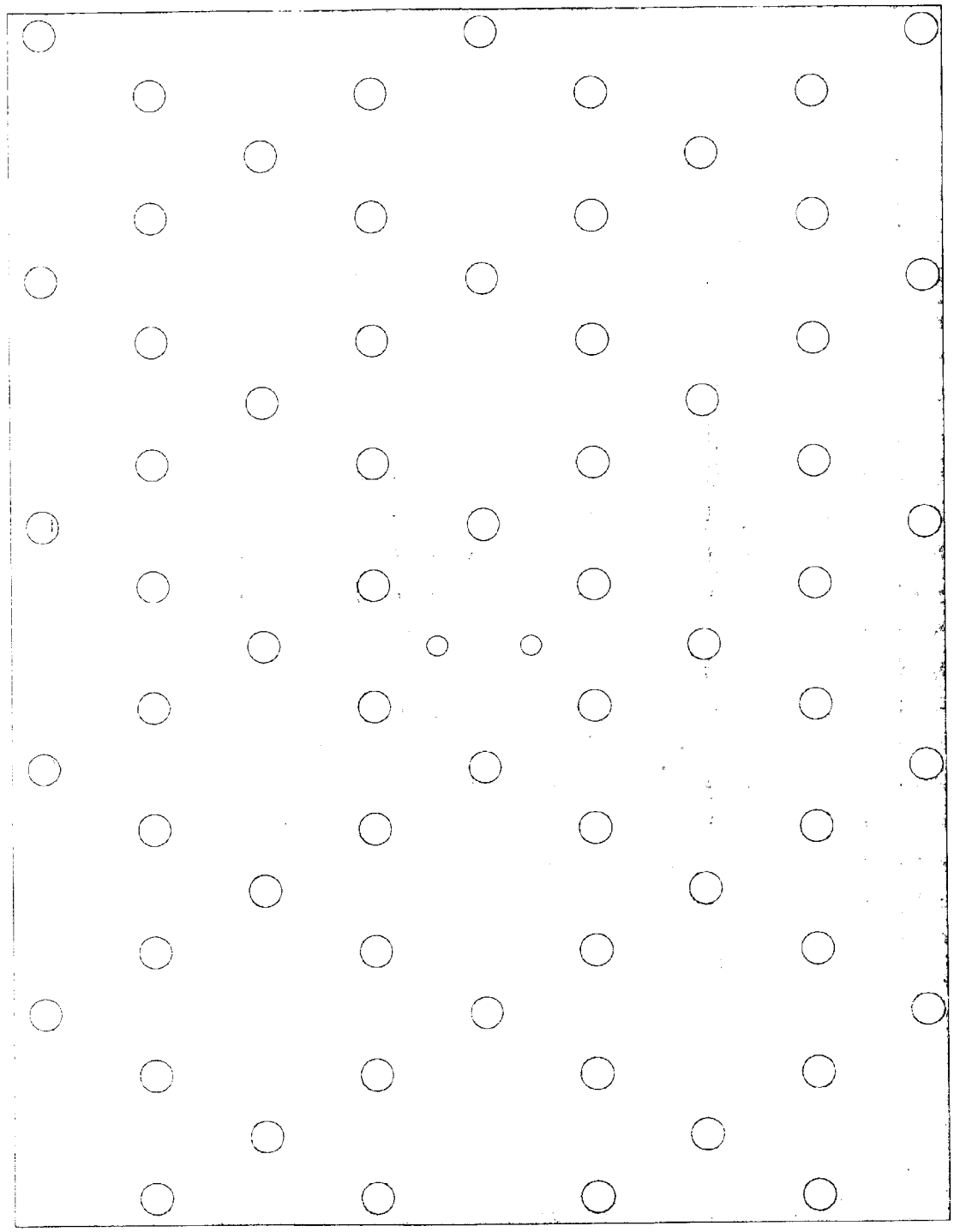
FIG. 49 shows two voids in the core cell, both voids having dimensions smaller than the voids defining the vertices of the Kagomé cladding cell.

Yet further examples as the one illustrated in FIG. 42 may use one void (50) of smaller dimensions than the voids forming the cladding cell (42) and the other (49) may be of larger dimensions. There may also be situations as illustrated in FIG. 43, where one void (50) may be of smaller dimensions as the voids forming the cladding cell (42) and the other (50) may be of equal dimensions. It should be noted that the examples presented in FIGS. 38–43, all have the same orientation of the line connection the two voids in the core cell, but this should in no way be seen as a preference to the possibility of placing the voids in the core cell. Indeed the two (or more) voids may not only have variable size, but they may also be placed in many different ways within the core cell, depending on the mode field shape requirements given by the specific application. Furthermore, even more voids than two may be placed in the core cell, and three, four or more voids may for specific applications be relevant for fibre fabrication. It should also be noted that the circular shaped cross-sections of the voids in the presented examples may be extended to include other shapes. Other possibilities include the introduction of groups of additional voids in different cladding structures than the Honeycomb cladding structure.

Examples of two-void defects in a Kagomé cladding structure is presented in FIGS. 44–49, where different detect forming void cross-section areas are applied. Note also that the chosen orientation of the defect forming two-void structure is not the only possibility, and an infinite number of alternative locations (including random location within the core cell may be used. Another important point is that the low-index spatial region, which forms the core, may extend much further than a single defect void/rod. Also connected voids/holes forming a single asymmetric super-void is covered by this invention.

The possibility of fabricating multi-core structures, is an interesting option for many future applications of optical fibres/waveguides, for instances in connection with spatial signal processing or as elements in complex coupler configurations. Such ideas have been suggested normal index-guiding waveguides, but the realisation of multi-core regions is technologically very difficult for standard fibres/waveguides. It is, therefore, a very attractive property of the PCPs that their fabrication (e.g., by stacking together tubes and rods) may allow relatively simple realisation of multi-core waveguides.

Figure 50:
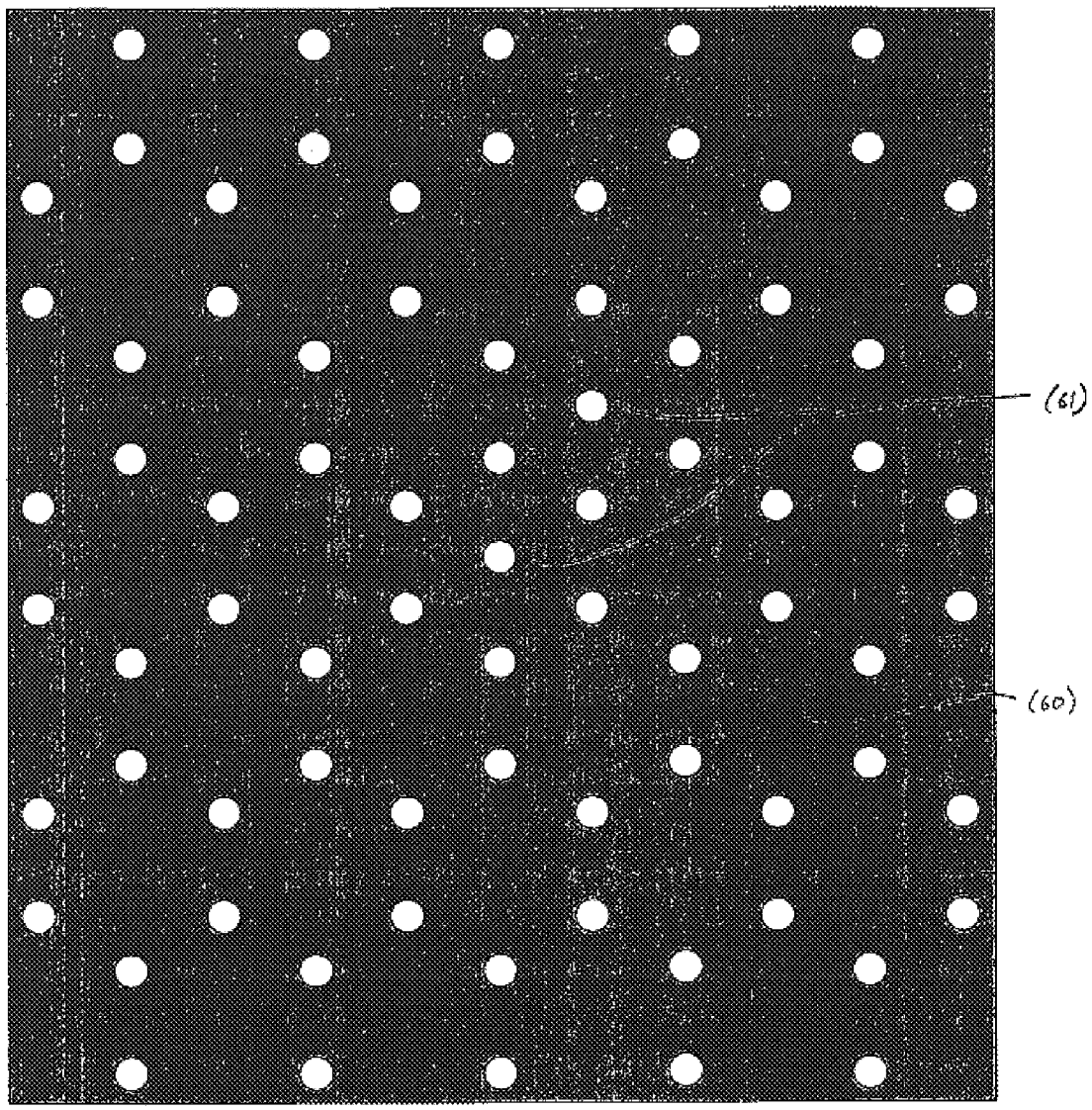
FIG. 50 shows two low-index defects which has been introduced in neighbouring cells to form a region in which guided mode(s) may propagate.
Figure 60:
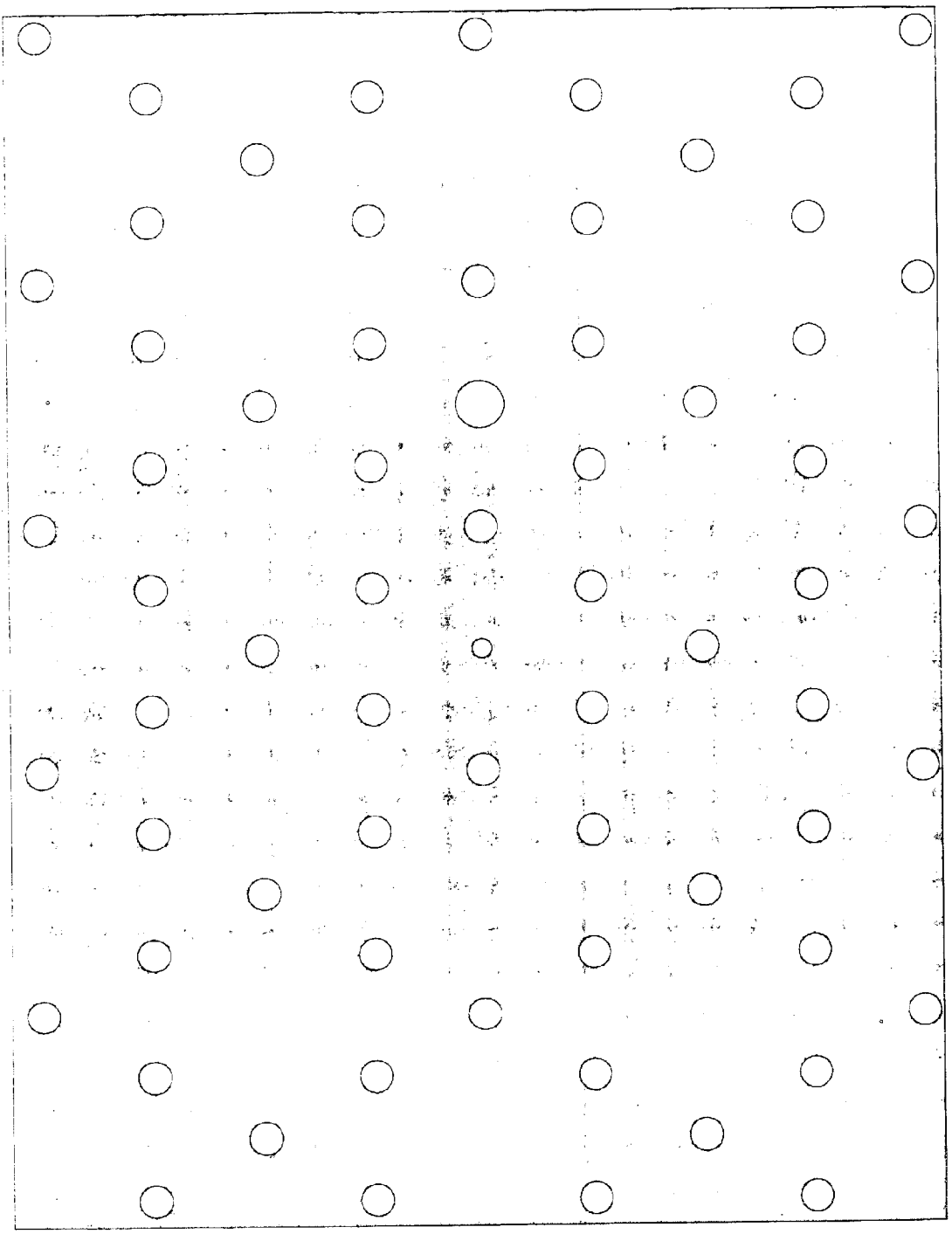
FIG. 60 shows two defect voids/holes, one void having a larger cross-section area than the voids defining the vertices of the Kagomé cladding structure, the other void having a smaller cross-section area than the voids defining the vertices of the cladding structure.

The present invention also includes such waveguides combining low-index core regions or low- and high-index regions, and among the examples of realistic embodiments are structures as shown in FIG. 50. In this example, the basic Honeycomb cell structure (60) has been used to form the photonic crystal cladding, and two low-index defects (61) has been introduced in neighbouring cells to form a region in which guided mode(s) may propagate. In FIG. 60, the defect voids have the same dimensions as the voids used to form the cladding structure.

Figure 51:
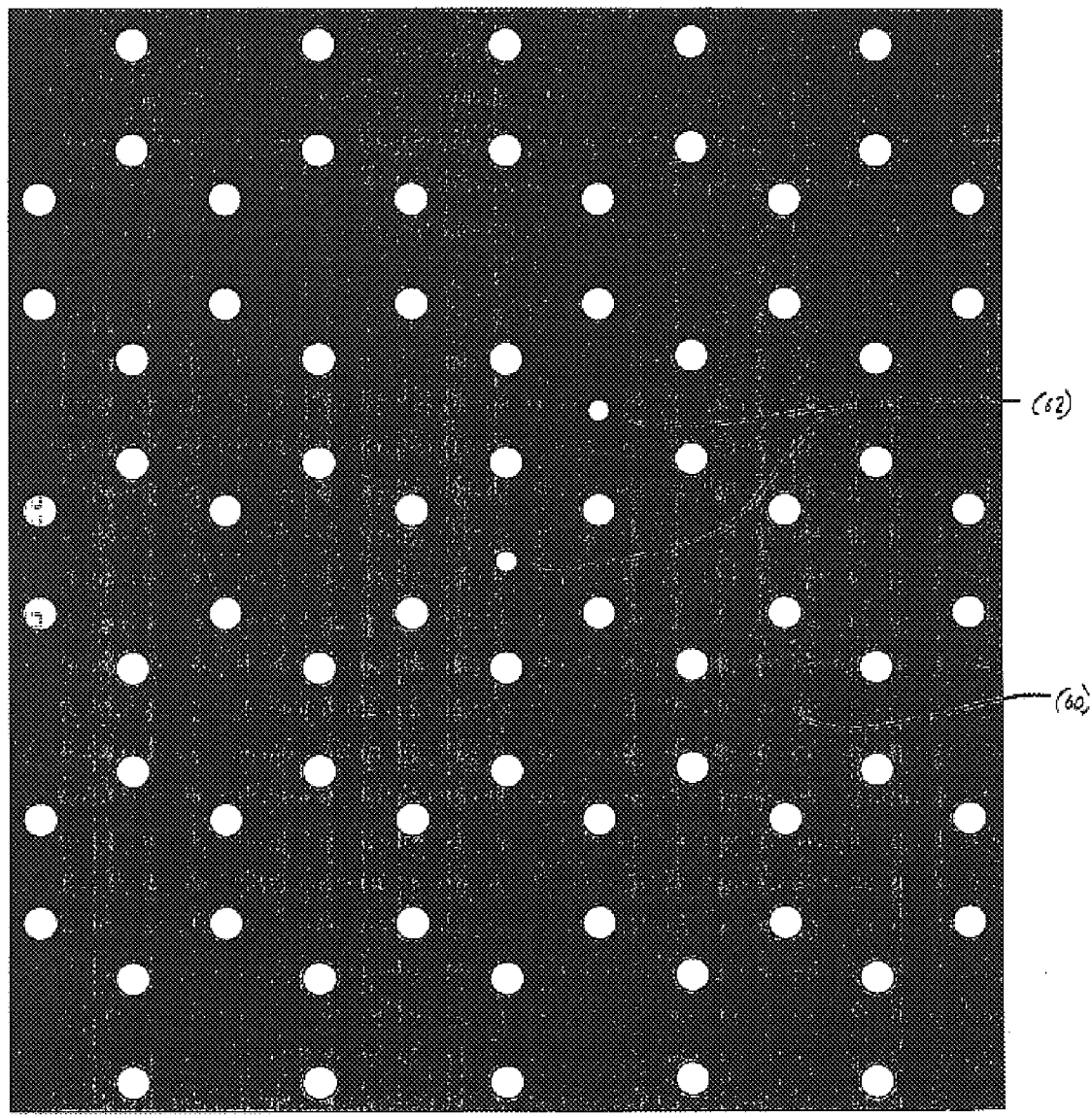
FIG. 51 shows defect voids/holes having smaller cross-section areas than the voids defining the vertices of the Honeycomb cladding structure.

Another example is presented in FIG. 51, in which the defect voids/holes (62) have smaller cross-section areas than the voids forming the cladding structure. By adjusting the relative sizes of the core (defect) voids compared to those of the cladding structure, means of mode shaping (and thereby waveguide property engineering) is obtained.

Figure 52:
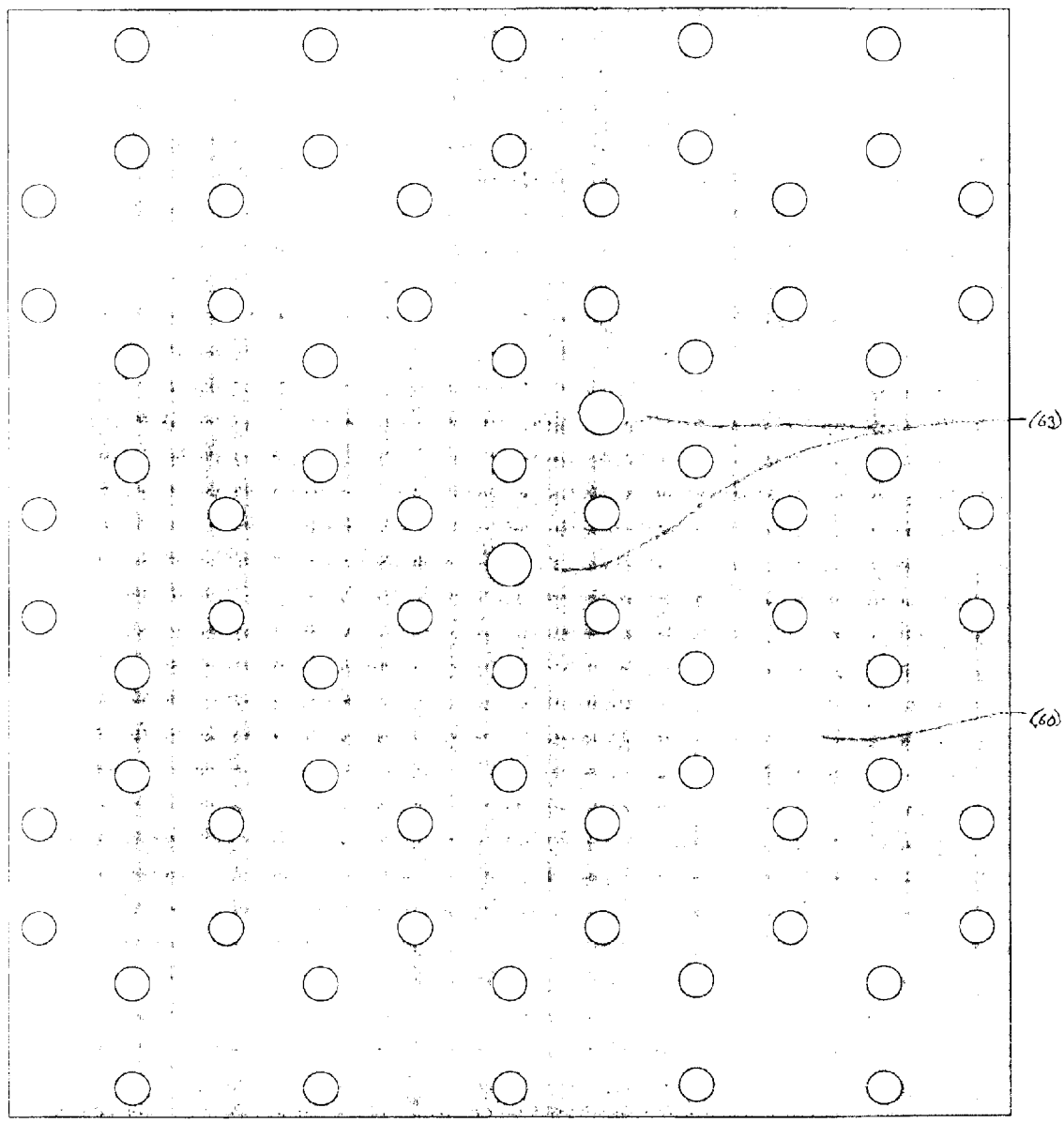
FIG. 52 shows defect voids/holes having larger cross-section areas than the voids defining the vertices of the Honeycomb cladding structure.
Figure 53:
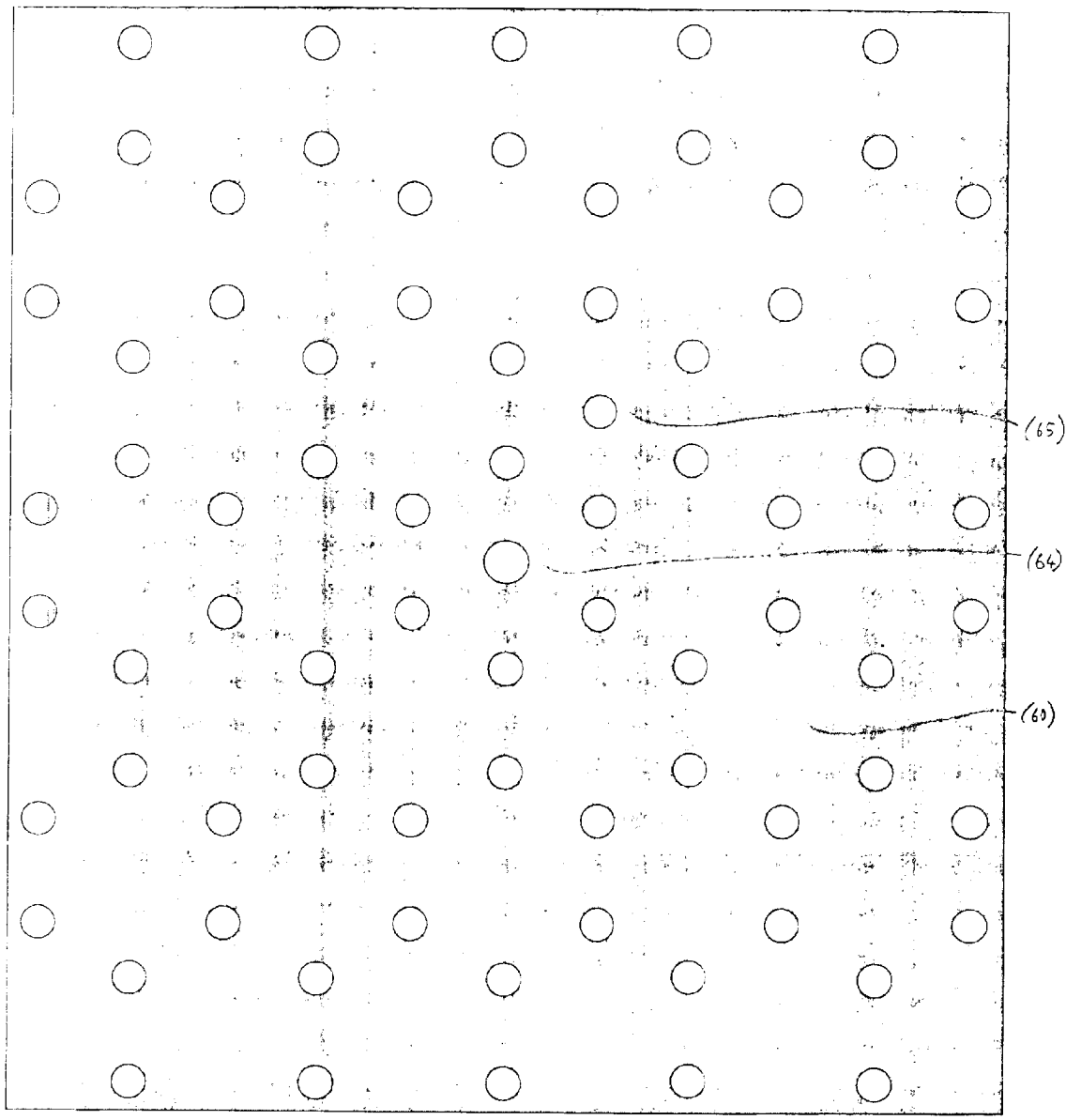
FIG. 53 shows two defect voids/holes, one void having a larger cross-section area than the voids defining the vertices of the Honeycomb cladding structure, the other void having a cross-section area as the voids defining the vertices of the cladding structure.

FIG. 52 illustrates an example in which the defect voids (63) have larger dimensions than the voids forming the Honeycomb cladding structure. It should be noted that the cross-sections of the defect voids/holes could be of any other shape than the circular one, and in the two core structure as discussed in this context, neither should the two defects have equal cross-sectional areas. A simple example of such a structure is shown in FIG. 53, where the two defect voids (64) and (65) have different cross-sectional areas. The void (64) has in this case a larger cross sectional area than the void (65), which has the same cross sectional-area as the voids forming the cladding structure.

Figure 54:
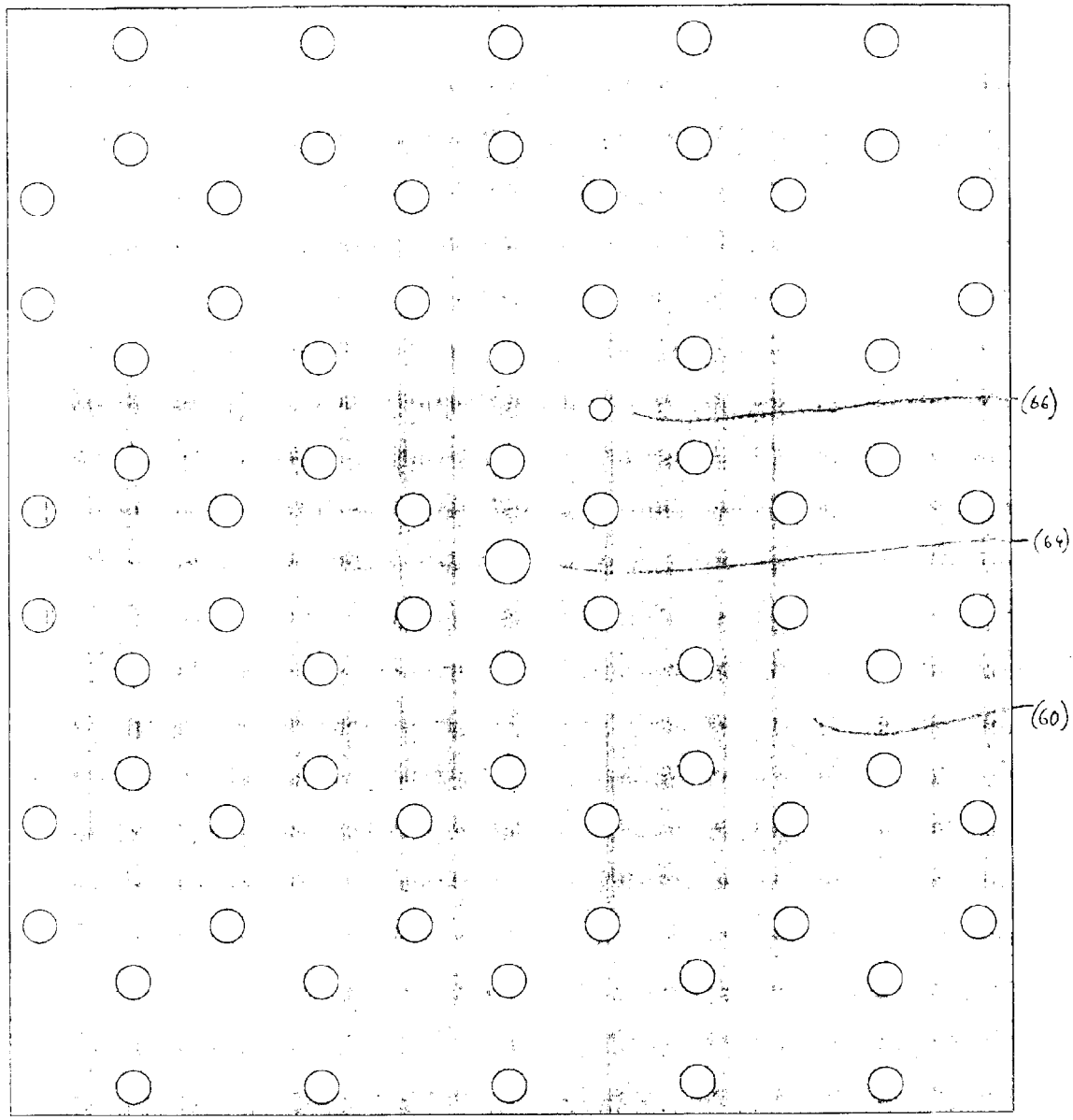
FIG. 54 shows two defect voids/holes, one void having a larger cross-section area than the voids defining the vertices of the Honeycomb cladding structure, the other void having a smaller cross-section area than the voids defining the vertices of the cladding structure.

Another possibility is shown in FIG. 54, where an embodiment with one void (64) of larger cross-sectional area and one void (66) of smaller cross-sectional area than the cladding forming voids is shown. Also here the simple Honeycomb structure with circular voids/holes has been shown as the example.

Figure 55:
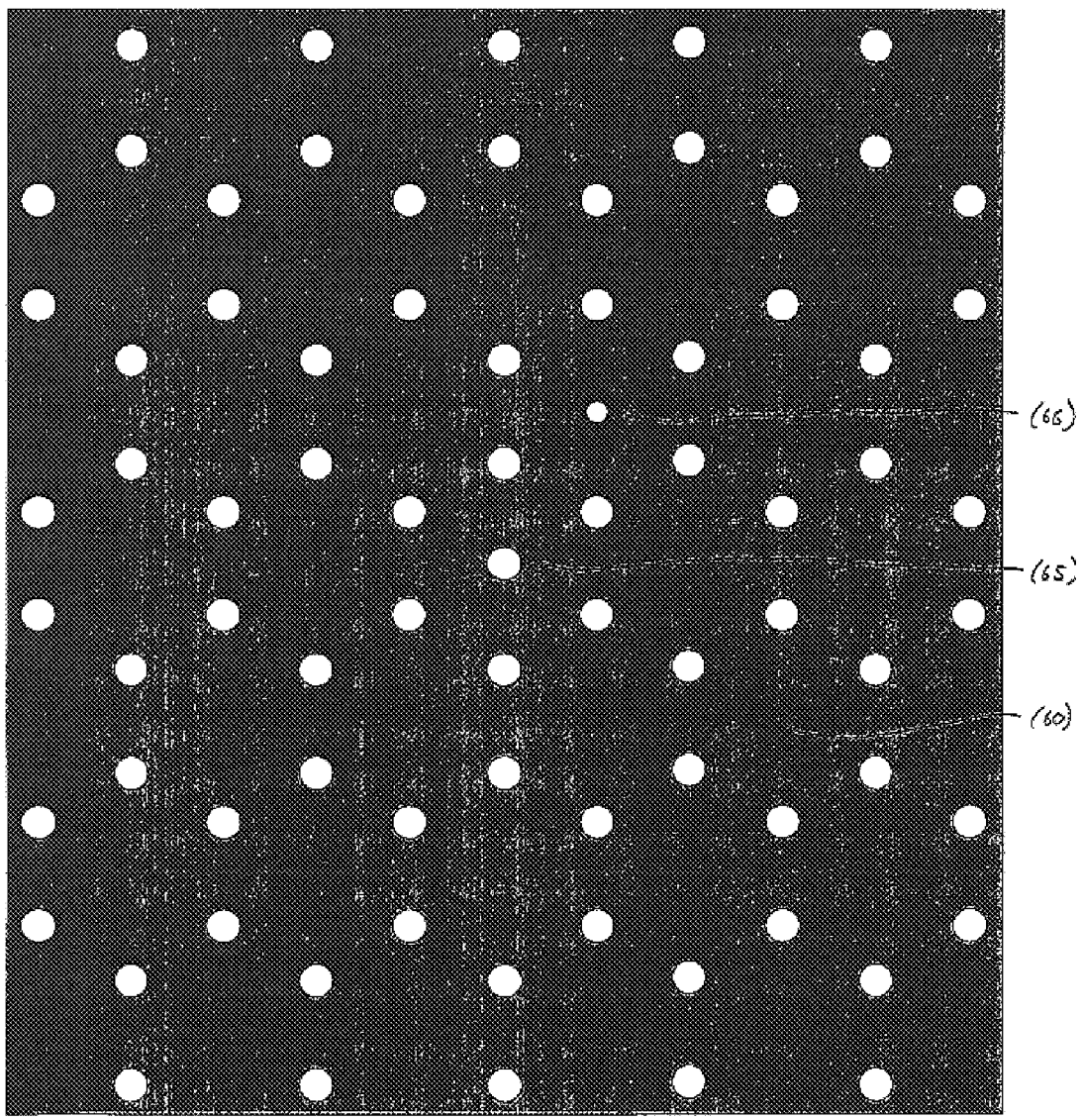
FIG. 55 shows two defect voids/holes, cell void having a smaller cross-section area than the voids defining the vertices of the Honeycomb cladding structure, the other void having a cross-section area as the voids defining the vertices of the cladding structure.

In FIG. 55 an alternative e>ample is given in which one void (66) of smaller cross-sectional area and one void (66) of equal cross-sectional area as the cladding forming voids is shown. In the specific examples shown in FIGS. 50–55, the defect voids have been placed centrally in the Honeycomb cells, but this is in no way a requirement within the present invention, since arbitrary locations of defect voids/holes within the unit cells may be applied with the purpose of engineering specific waveguiding properties. The idea of applying multiple defects in the periodic cladding cell structure is not limited to the simple Honeycomb unit cell, but may also be applied for other cladding structures.

Figure 56:
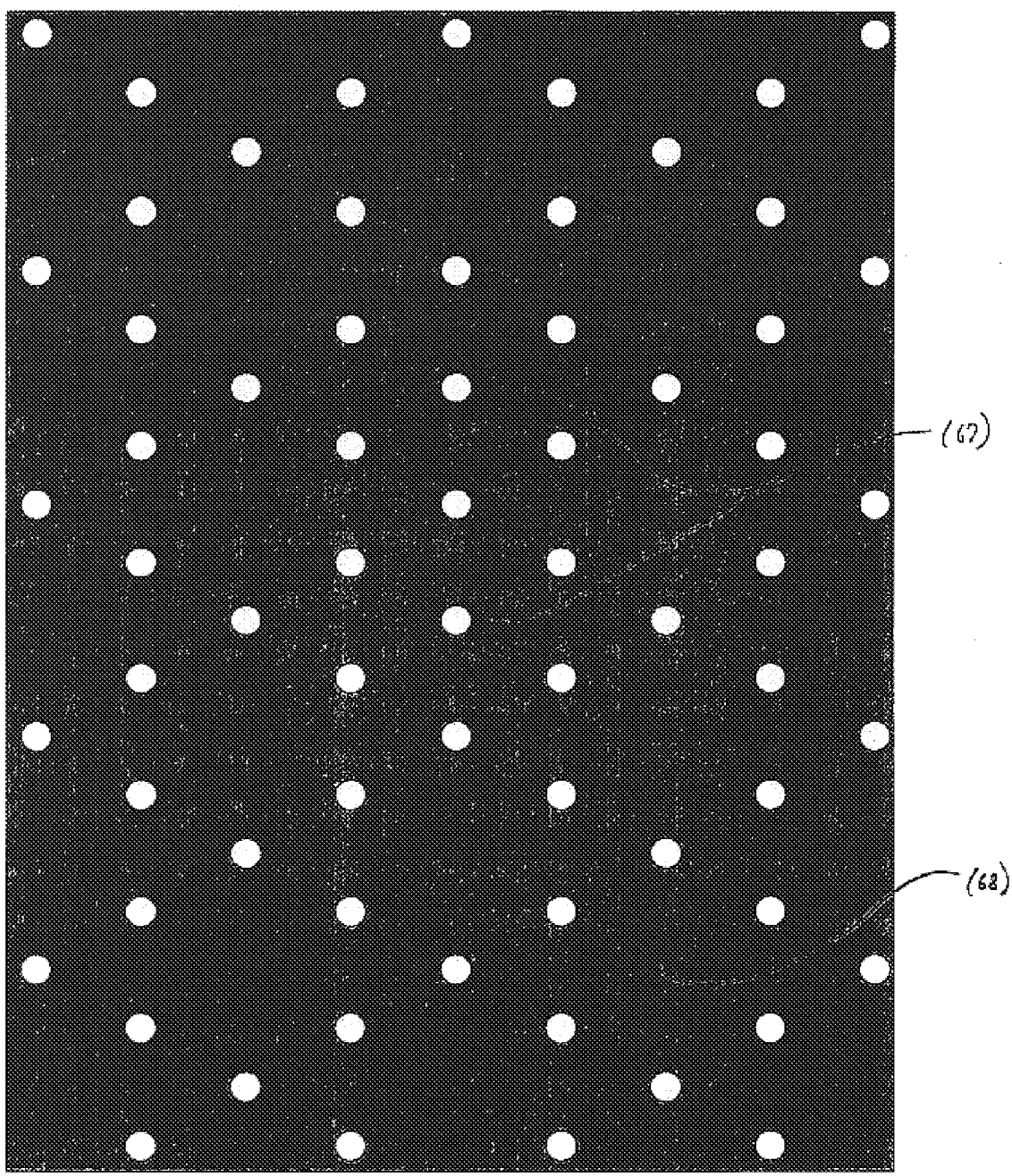
FIG. 56 shows two low-index defects which has been introduced in neighbouring cells to form a region in which guided mode(s) may propagate. The defect voids have the same dimensions as the voids used to form the Kagomé cladding structure.
Figure 52:
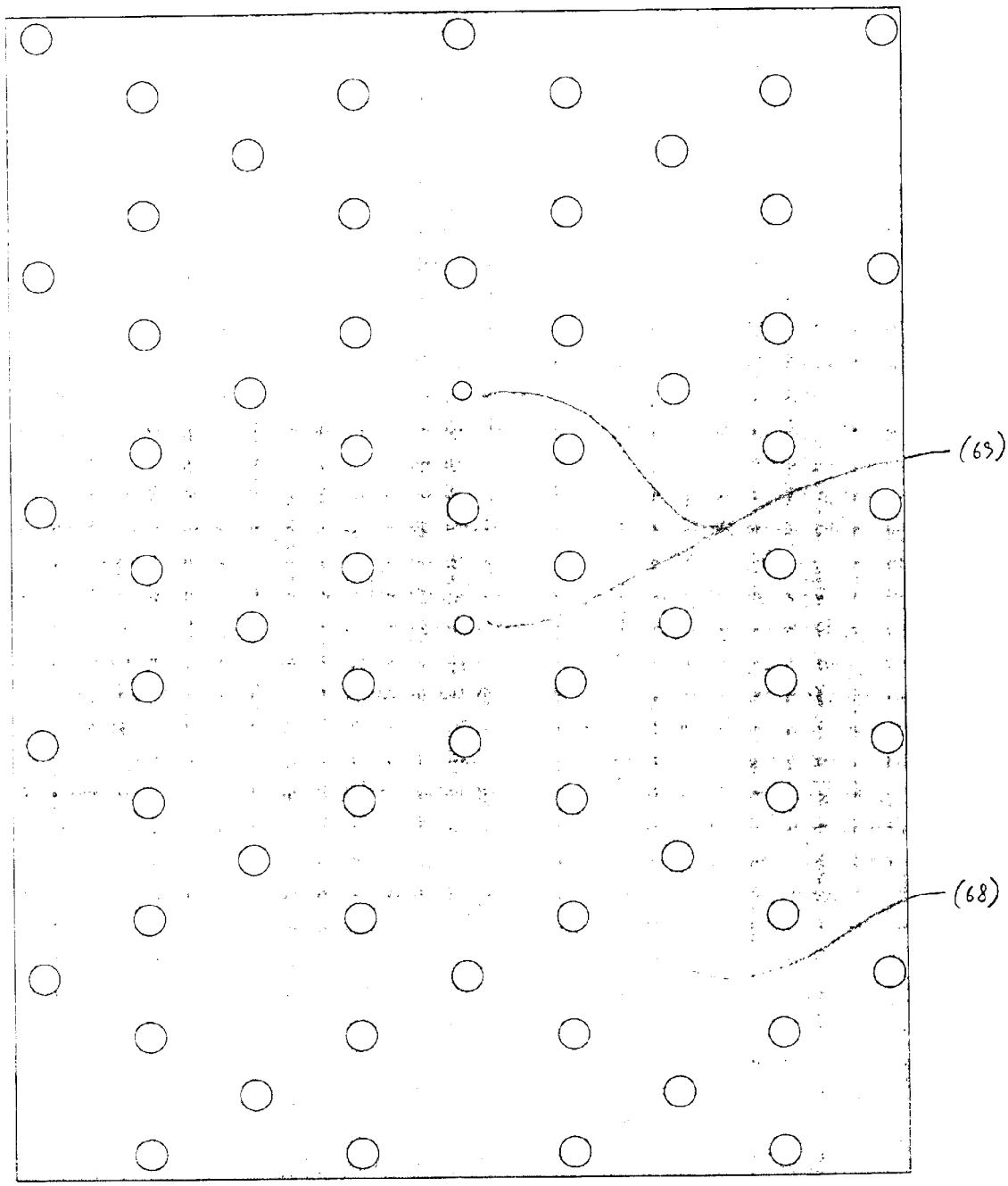
Figure 58:
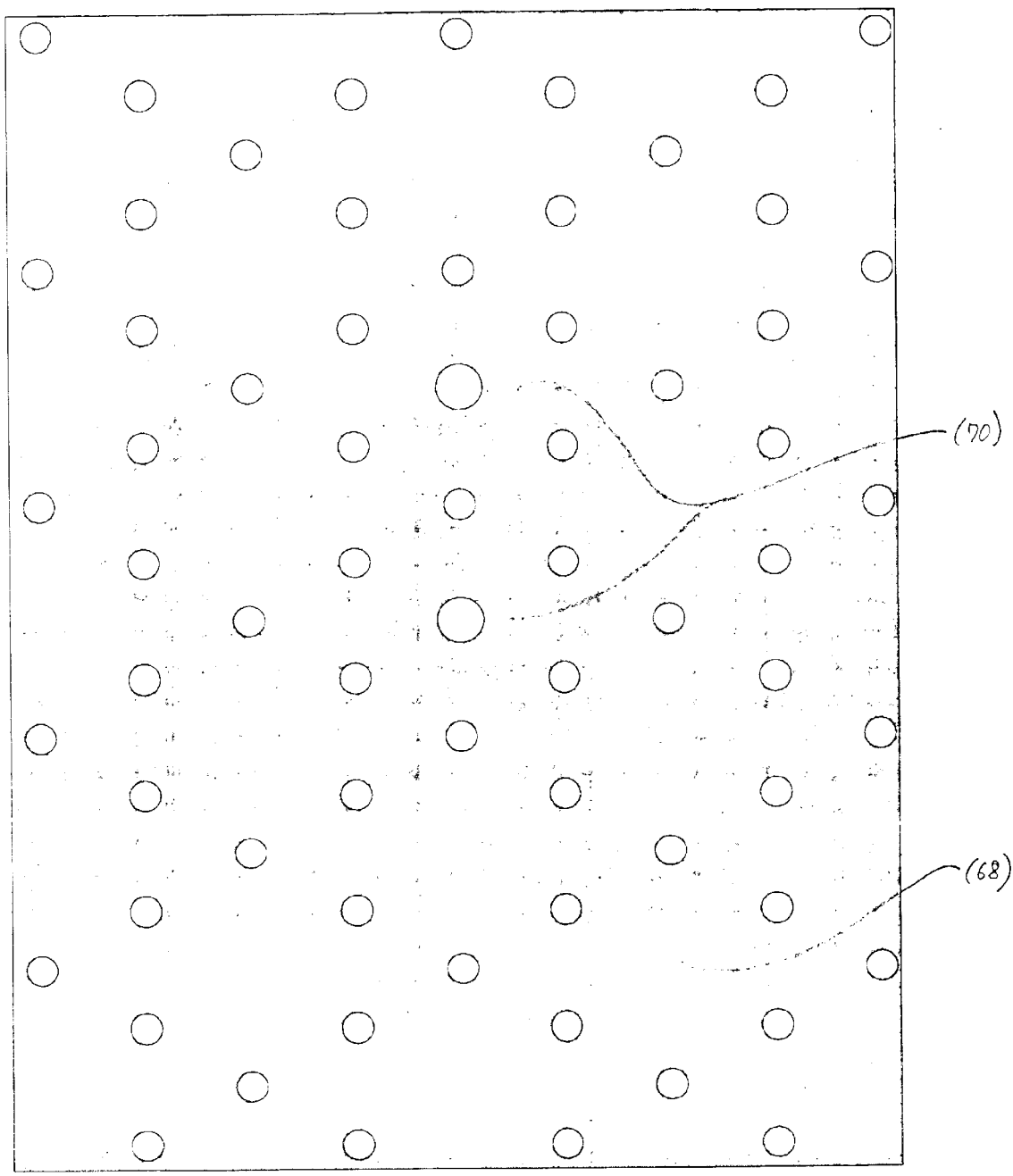
FIG. 58 shows defect voids/holes having larger cross-section areas than the voids defining the vertices of the Kagomé cladding structure.

One example is illustrated in FIG. 56, where an example is shown of a Kagomé cladding structure (68) with two detect voids (67) of equal dimensions as the voids used to form the cladding structure.

Figure 59:
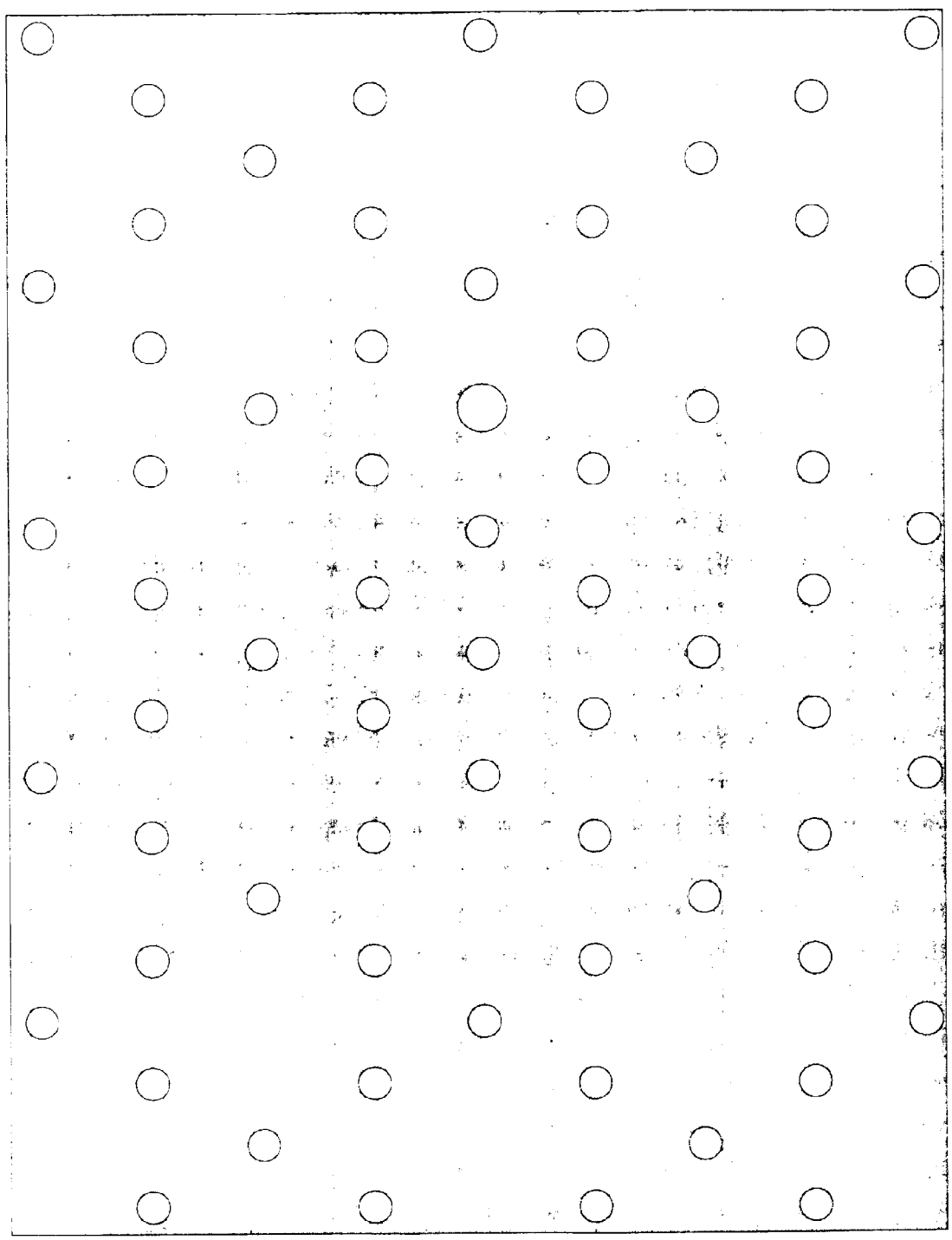
FIG. 59 shows two defect voids/holes, one void having a larger cross-section area than the voids defining the vertices of the Kagomé cladding structure, the other void having a cross-section area as the voids defining the vertices of the cladding structure.
Figure 61:
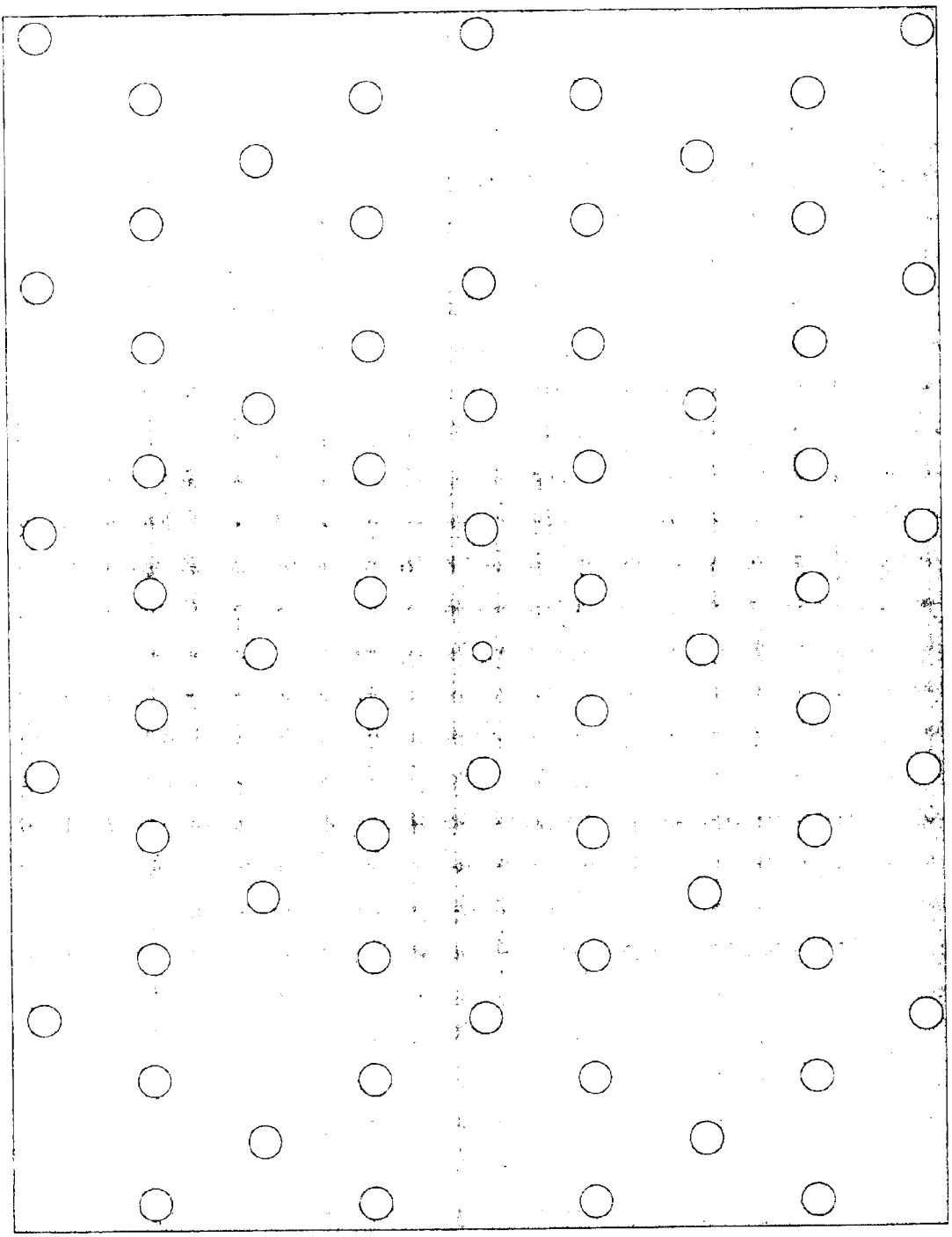
FIG. 61 shows two defect voids/holes, one void having a smaller cross-section area than the voids defining the vertices of the Kagomé cladding structure, the other void having a cross-section area as the voids defining the vertices of the cladding structure.
Figure 68:
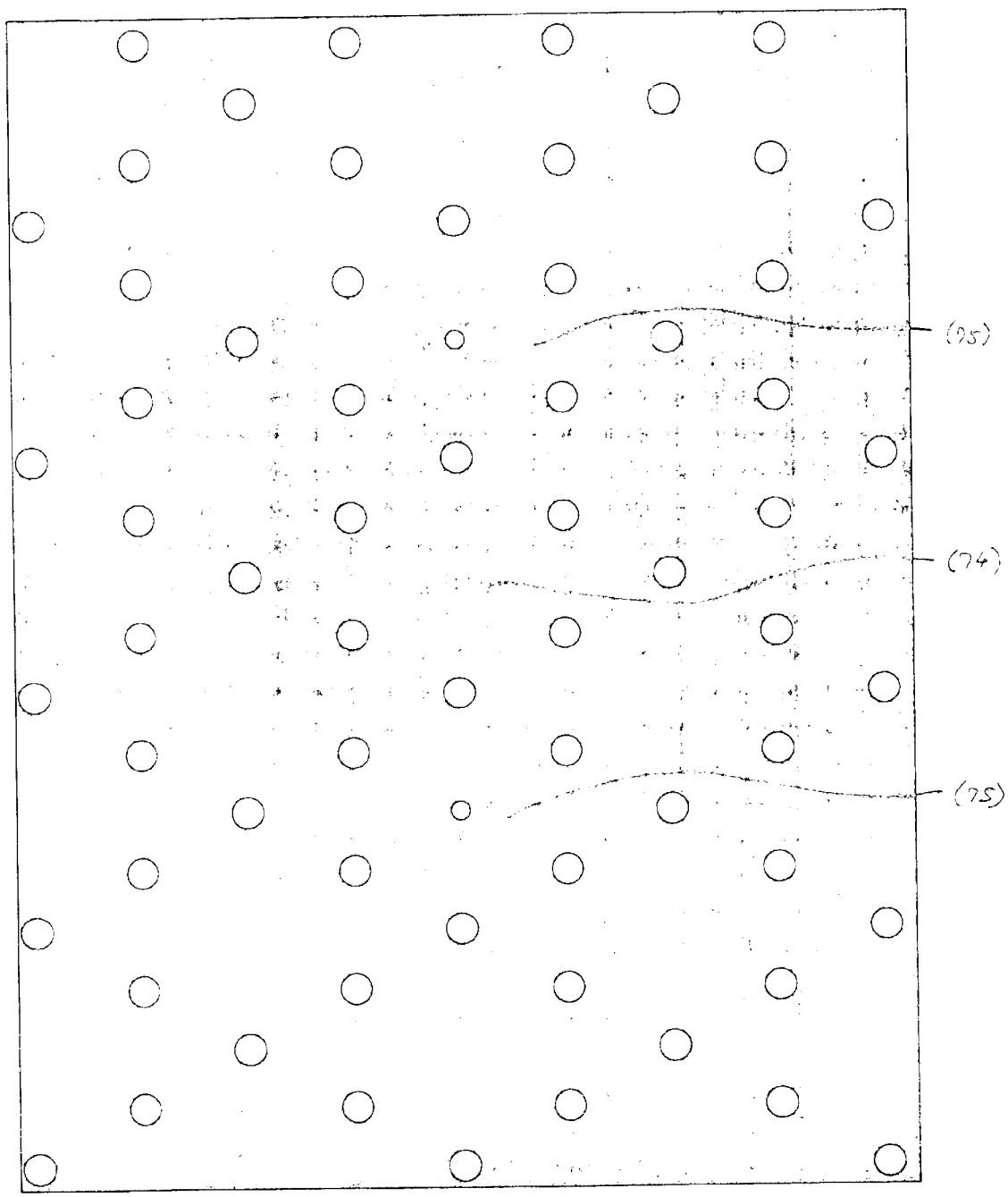
FIG. 68 shows a cell without a defect placed between two cells containing defect voids. The defect forming voids have smaller cross-sectional areas than the voids defining the vertices of the simple Kagomé cladding structure.

In FIG. 57, another embodiment shows a Kagomé cladding structure, which has been modified by two defect voids/holes (69) of smaller cross-section areas than the voids forming the cladding structure. In analogy with the simple Honeycomb cladding examples previously discussed, the defects may also be of larger cross-sectional areas than the cladding structure forming voids as shown in FIG. 68, and different examples of two defect holes of different cross-sectional areas are illustrated for the Kagomé cladding structure in FIGS. 59–61.

In all the examples shown in FIGS. 50–61, the two defect voids/holes were placed in neighbouring cells, but this is not always preferable. For instance in cases, where weaker coupling or even no power coupling is needed, it may be advantageous to apply larger spacing between the multiple defects (or core) areas.

Figure 62:
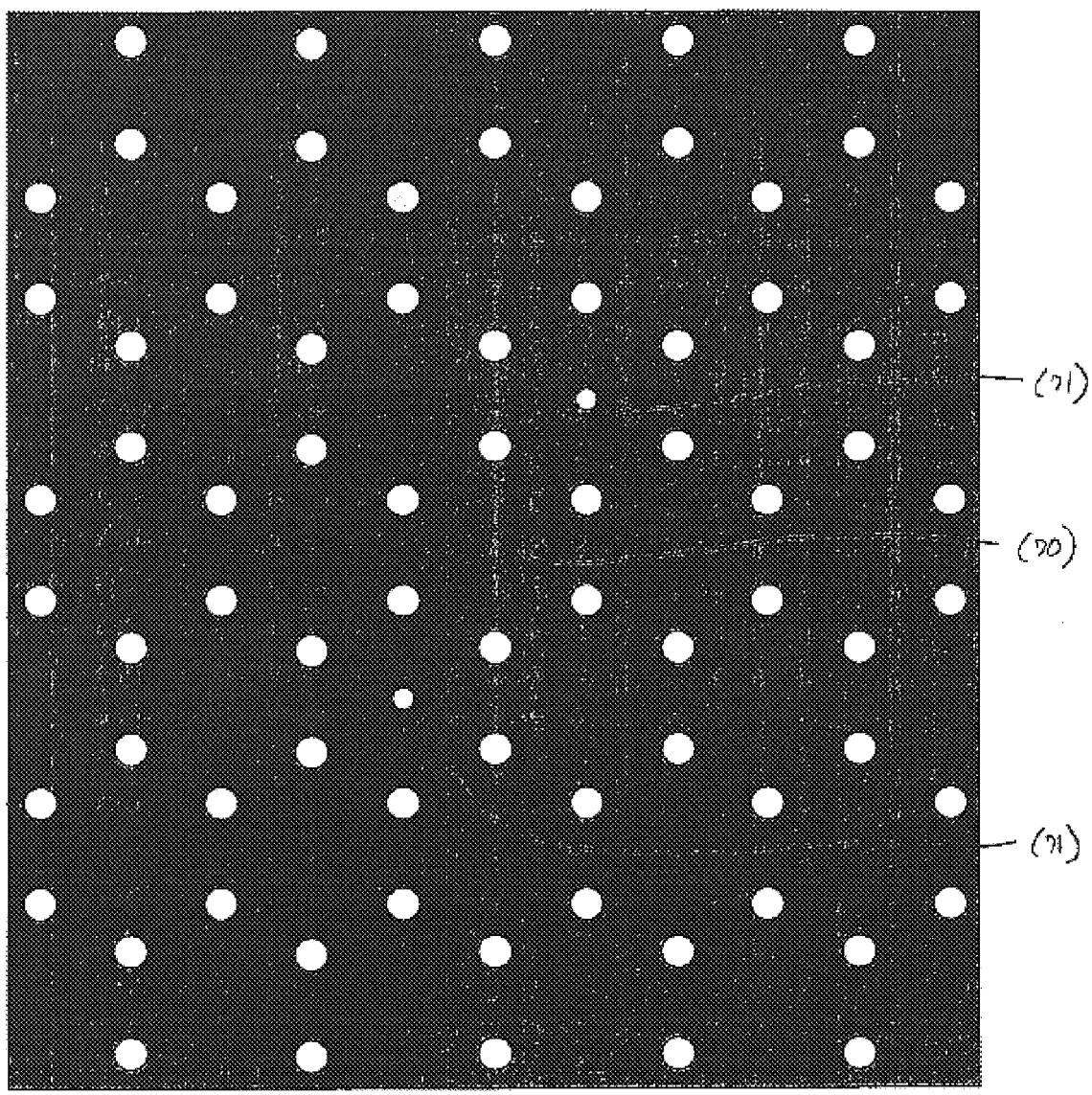
FIG. 62 shows a cell without a defect placed between two cells containing defect voids. The defect defining the vertices of voids have smaller cross-sectional areas than the voids defining the vertices of the simple Honeycomb cladding structure.

To exemplify this, the simple Honeycomb cladding structure has been shown together with two defects, which in FIG. 62 has been located in such a way that one cell (70) without defect is placed in between the two cells (71) containing defect voids. In the embodiment of FIG. 62, the defect forming voids have smaller cross-sectional areas than the voids forming the simple Honeycomb cladding structure.

Figure 63:
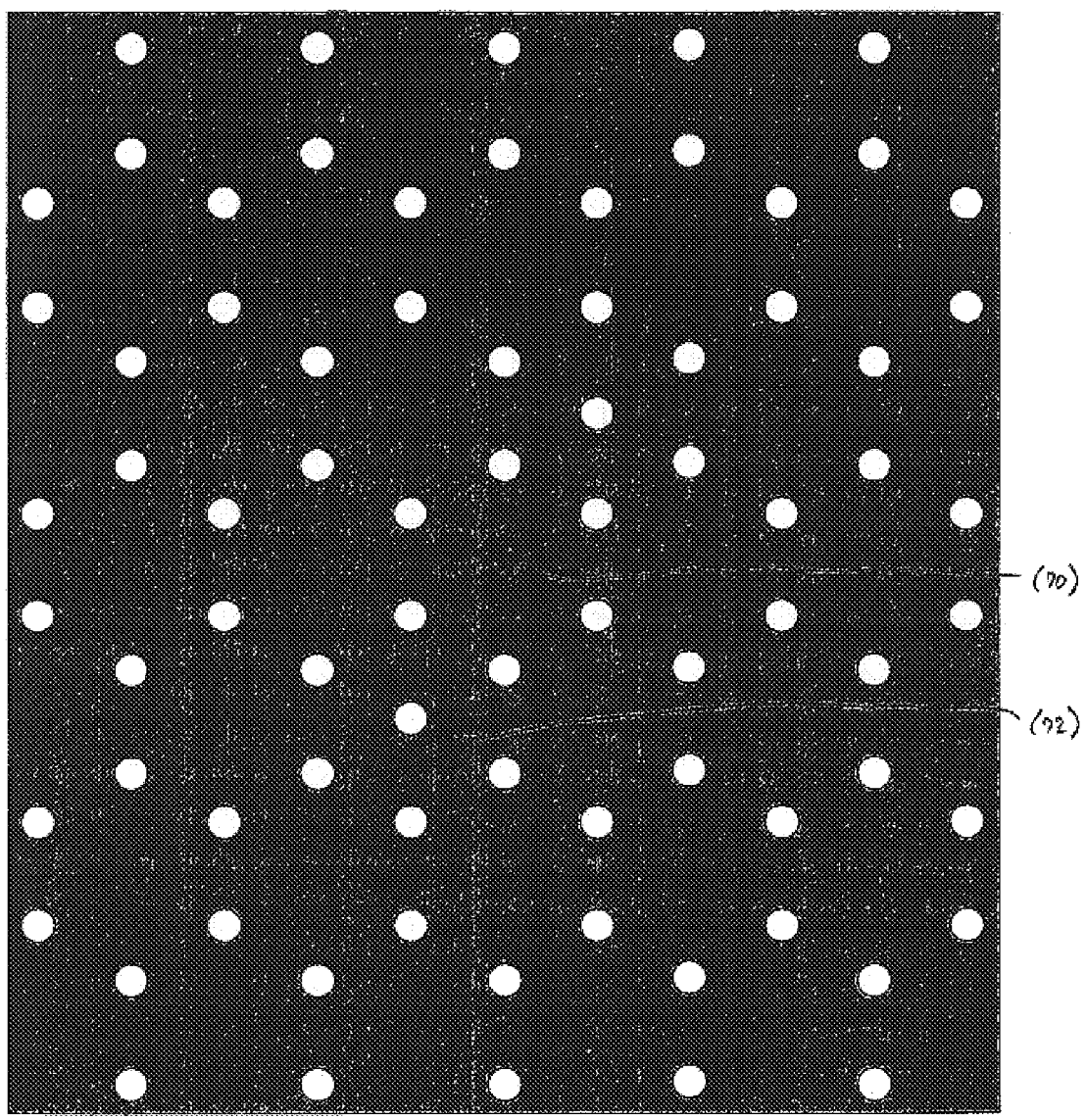
FIG. 63 shows a cell without a defect placed between two cells containing detect voids. The defect forming voids have cross-sectional areas as the voids defining the vertices of the simple Honeycomb cladding structure.

Another example is presented in FIG. 63, where cells (72) with defect forming voids of equal cross-sectional area as the cladding forming voids is shown. Also defect calls formed by voids/holes of different cross-sectional areas may be used.

Figure 64:
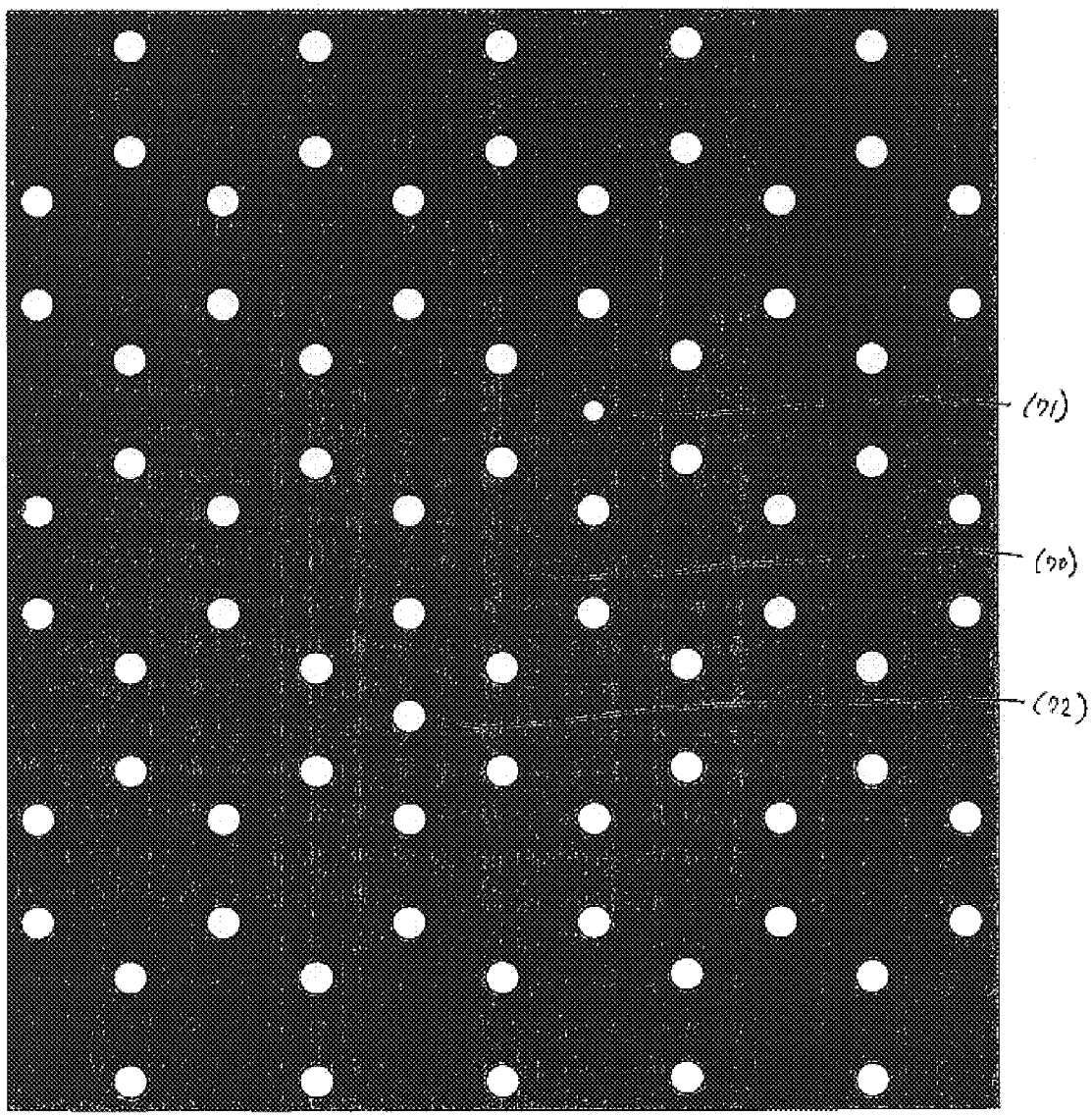
FIG. 64 shows a cell without a defect placed between two cells containing defect voids. One of the defect forming voids has a cross-sectional area as the voids defining the vertices of the simple Honeycomb cladding structure, the other defect forming void has a cross-sectional area smaller than the cladding structure.

In FIG. 64, an example is shown in which two detects have been located in such a way that one cell (70) without defect is placed in between one cell (71) containing a smaller defect void and another cell (72) containing an equal sized detect void as those voids forming the cladding structure.

Figure 65:
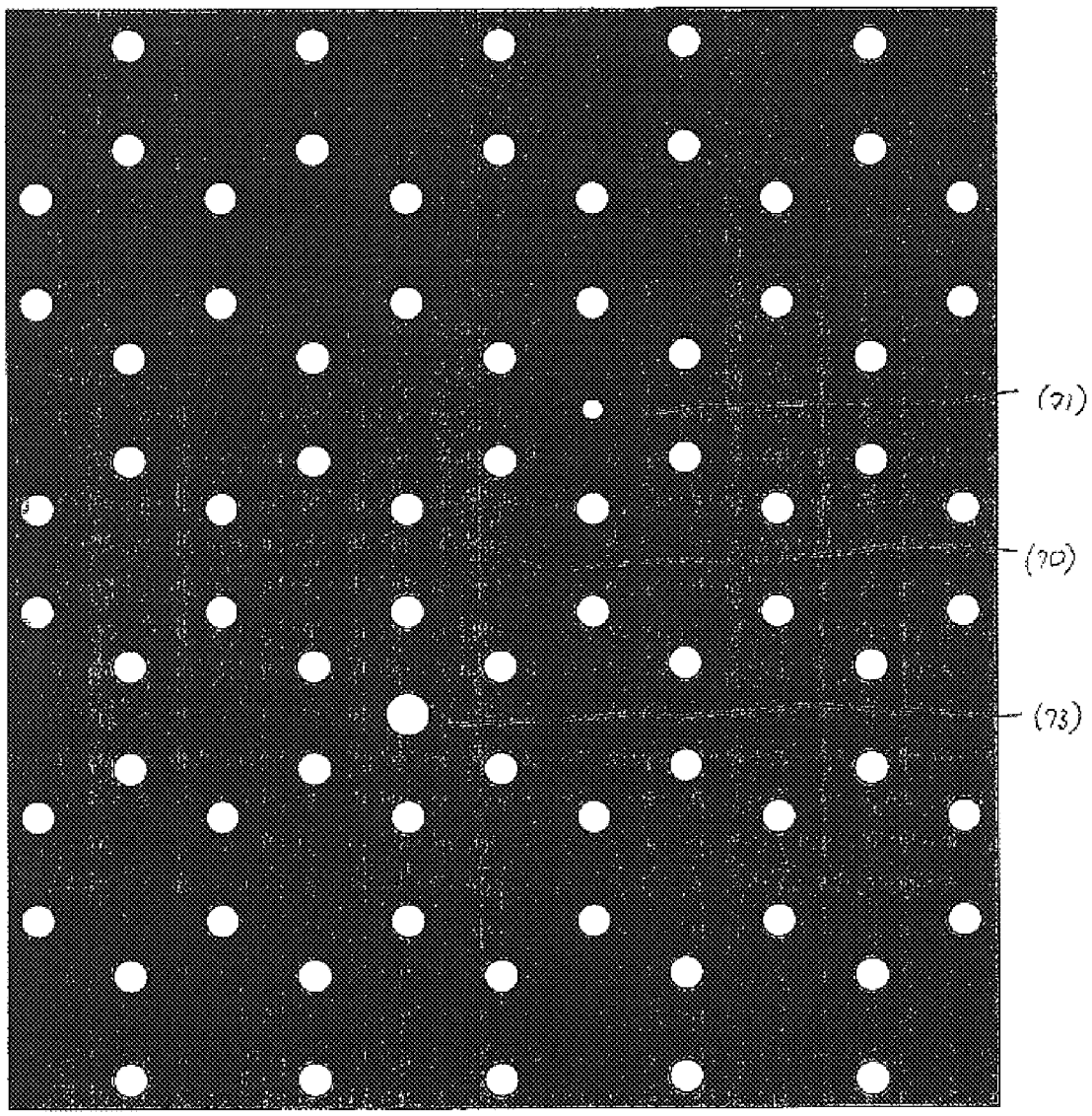
FIG. 65 shows a cell without a defect placed between two cells containing defect voids. One of the defect forming voids has a cross-sectional area smaller than the voids defining the vertices of the simple Honeycomb cladding structure, the other defect forming void has a cross-sectional area larger than the cladding structure.
Figure 66:
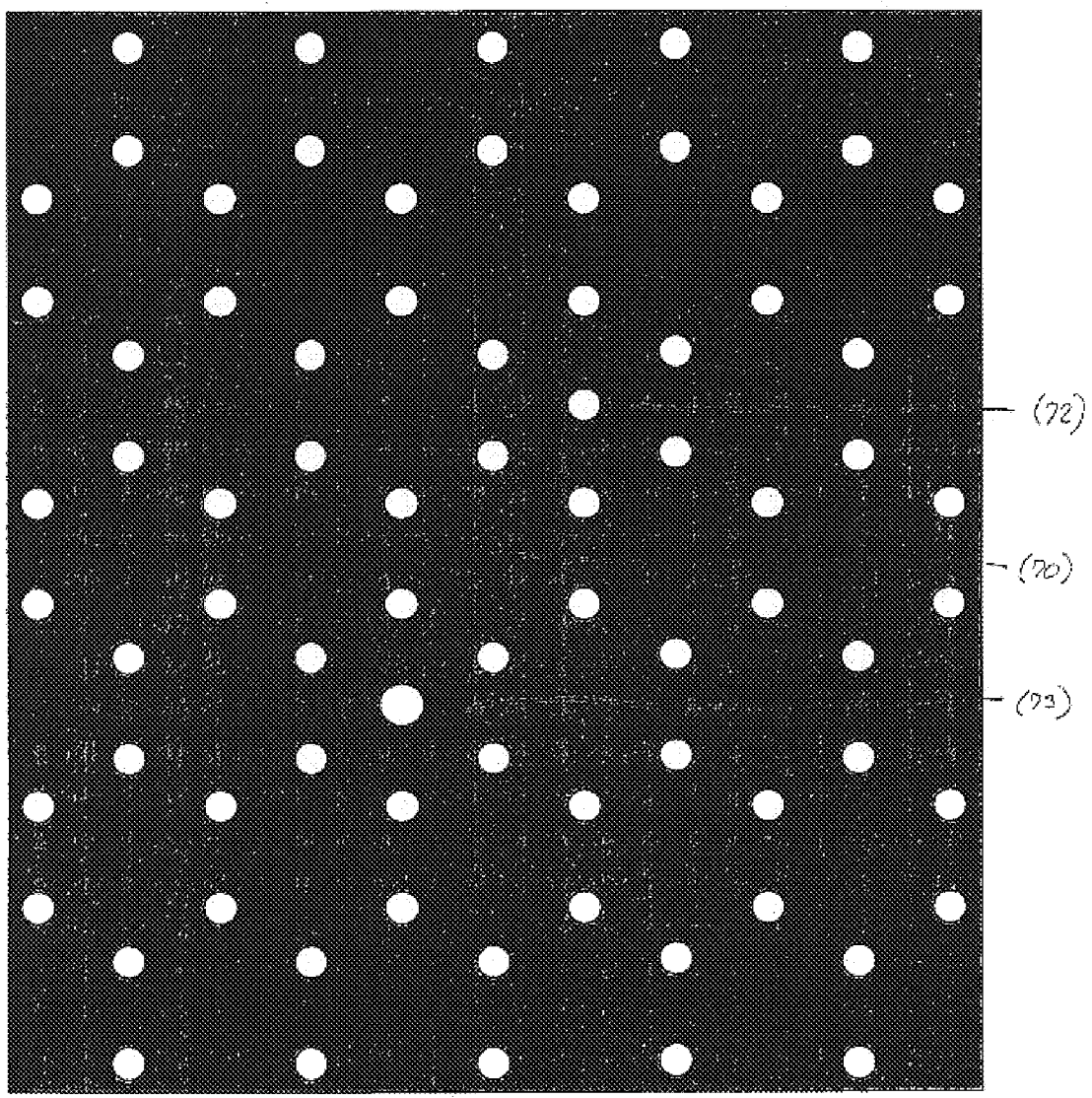
FIG. 66 shows a cell without a defect placed between two cells containing defect voids. One of the defect forming voids has a cross-sectional area as the voids defining the vertices of the simple Honeycomb cladding structure, the other defect forming void has a cross-sectional area larger than the cladding structure.
Figure 62:
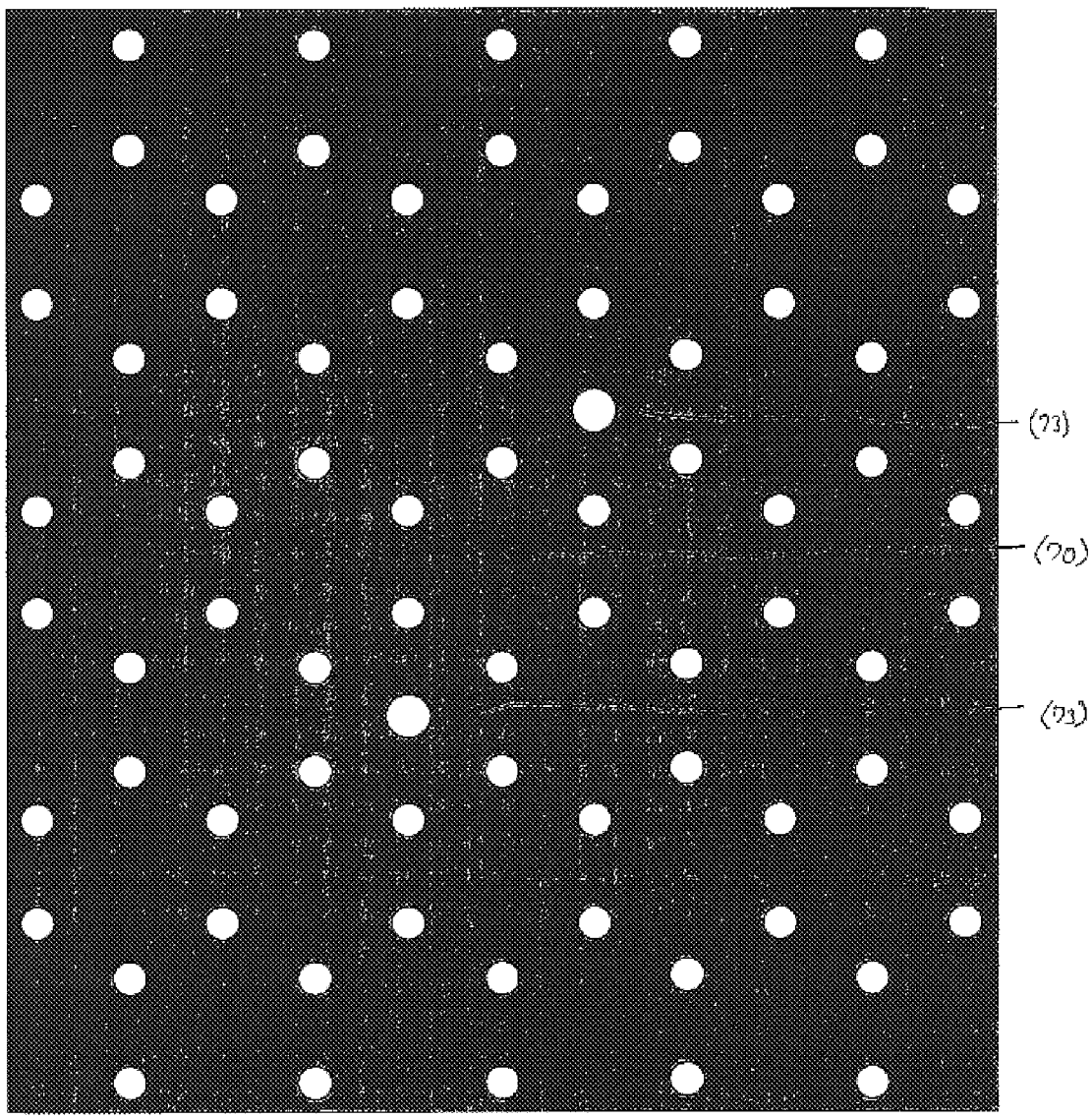

FIG. 65 shows an example where a cell (73) with a defect void of larger cross-section area is placed with a separation of one cell from another cell (71) with a smaller defect void. Two different combination examples with separated core areas in simple Honeycomb cladding structures are shown in FIGS. 68–67. It should also be stressed that more than one cladding cell could be used to separate defect containing cells, and also more than two defects may be included in a single fibre.

Multiple defects in the periodic cladding cell structure may also be applied for other cladding structures. One example is illustrated in FIG. 68, where an example is shown of a Kagomé cladding structure (74) with two defect voids (7) of smaller dimensions than the voids used to form the cladding structure, placed in with a separation of one cell (74) between the detect cells.

Figure 69:
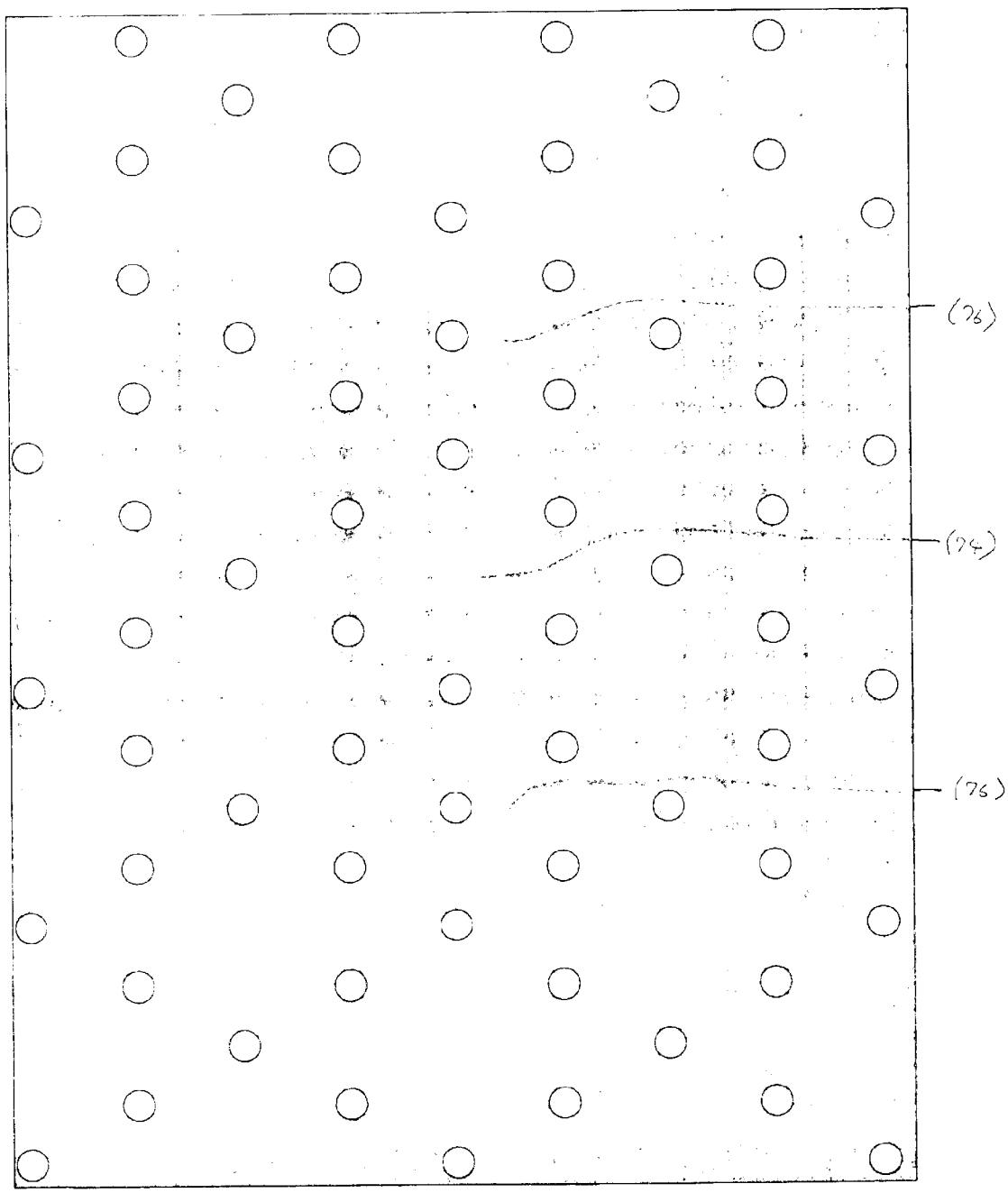
FIG. 69 shows a cell without a defect placed between two cells containing defect voids. The defect forming voids have cross-sectional areas as the voids defining the vertices of the simple Kagomé cladding structure.

In FIG. 69, another embodiment shows a Kagomé cladding structure, which has been modified by two defect voids/holes (76) of equal cross-section areas as the voids forming the cladding structure. Also here one cladding cell has been used to separate the two defect cells.

In analogy with the simple Honeycomb cladding examples previously discussed, the defects may also be of larger cross-sectional areas than the cladding structure forming voids or of non-equal size as shown in different examples in FIGS. 70–73, for the Kagomé cladding structure. As it previously has been discussed, the defects may be formed by a combination of several voids/holes, and this approach may also be combined with the multiple-core approach discussed in this part of the description. This leads to a wide range of design possibilities, where one defect may be constructed in one way (e.g., by a single void), while others may be constructed differently. This may not only be done with respect to cross-section but also with respect to the number of substructures that are to be used in the formation of the defects (for example may another defect be formed by three closely spaced triangular voids/holes).

It has previously been mentioned that the use of voids with non-circular cross-sections may be applied for mode shaping purposes and because the physical properties given by the fabrication process may shape the individual voids in specific cross sections. All these possibilities may be combined with all the previously mentioned combinations of different cladding structures, multi-element voids, single- or multiple defects etc. A few examples of voids with cross-sections different from the circular ones are shown in FIGS. 74–81.

Figure 74:
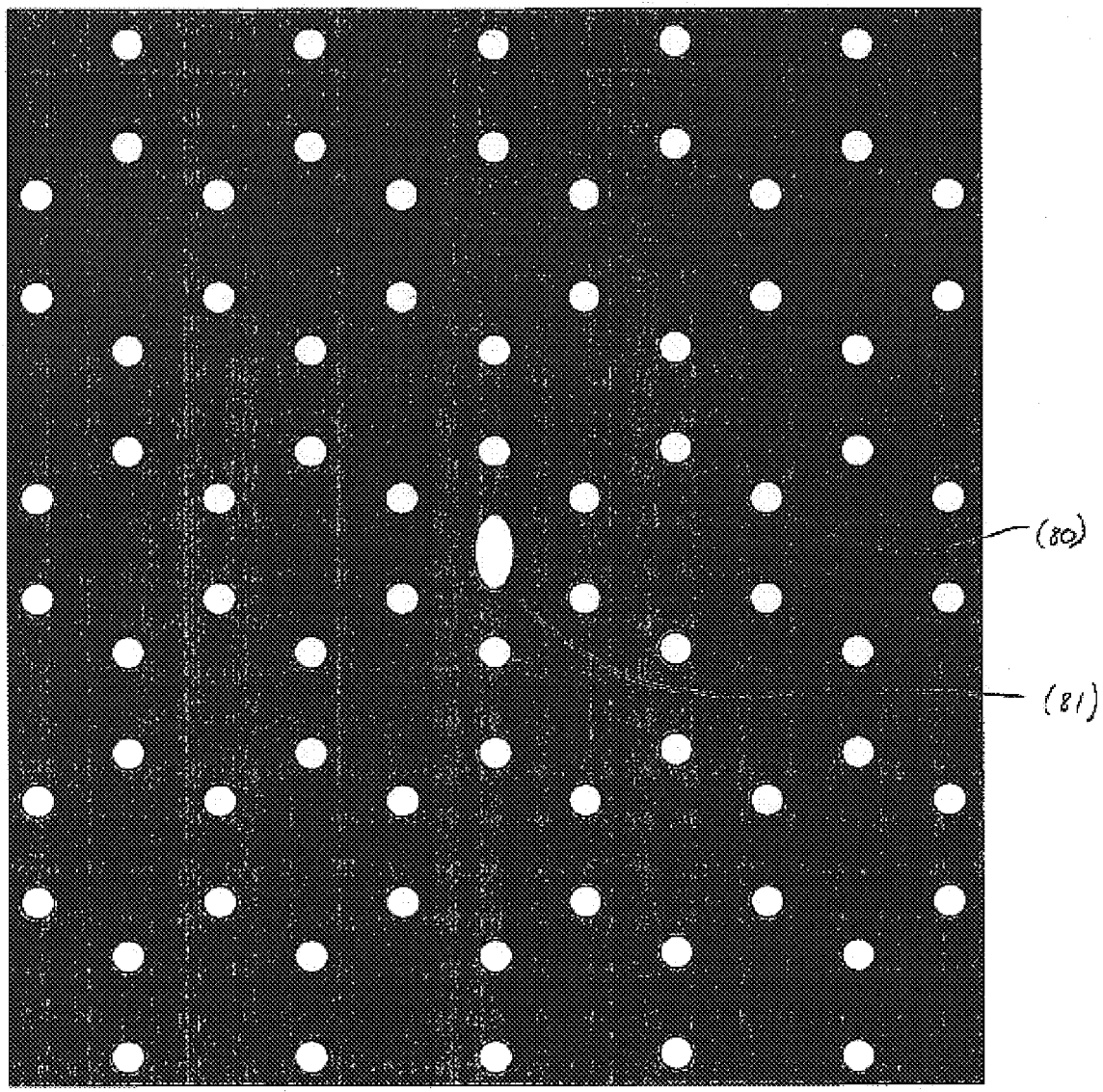
FIG. 74 shows a simple Honeycomb cladding structure with circular voids in the cladding cells for a case where the core (defect) site is formed by a void with elliptical cross section. The cross-sectional area of the elliptical core is larger than the cross-sectional area of the voids defining the vertices of the cladding structure.
Figure 75:
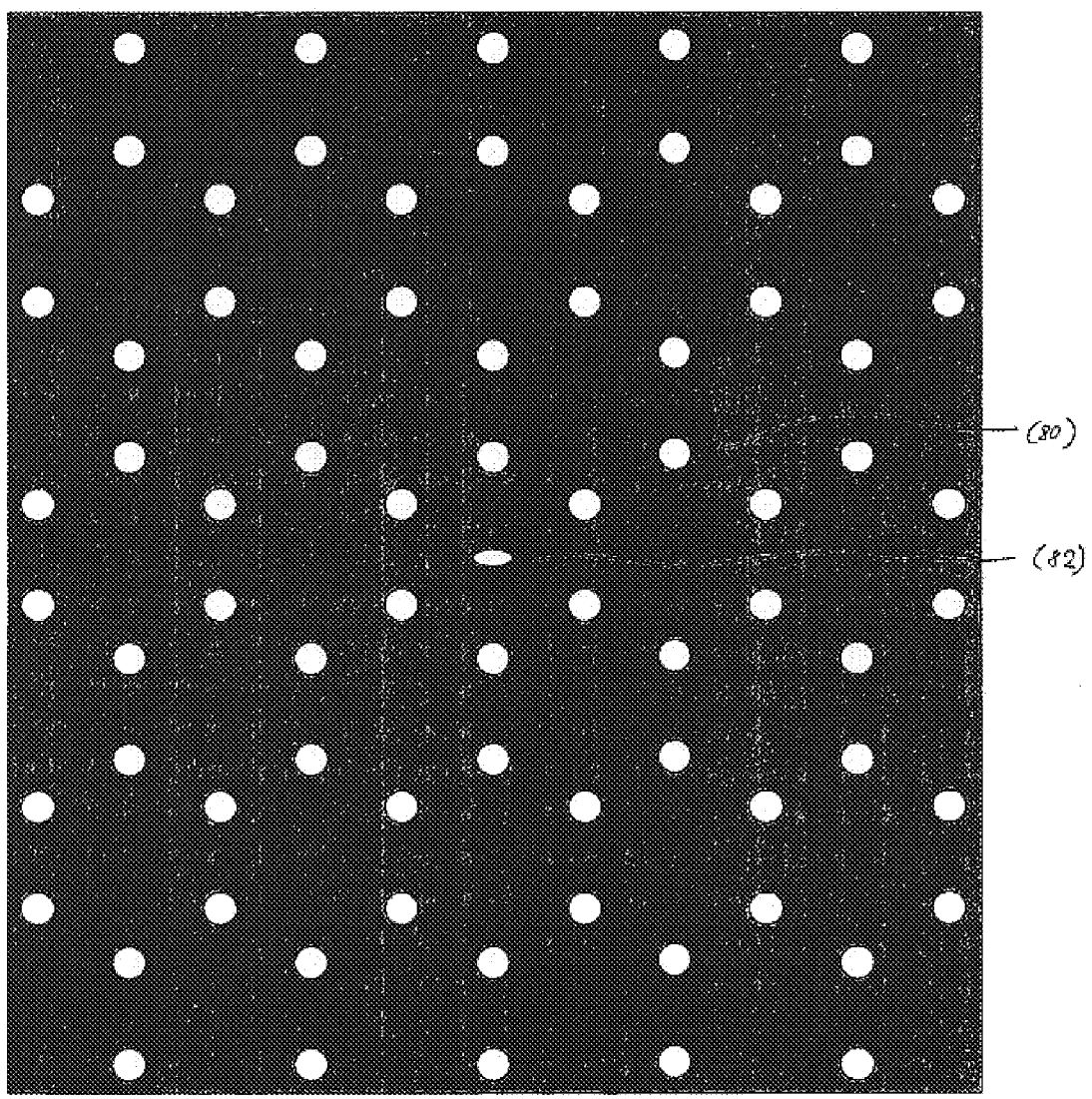
FIG. 75 shows a void/hole with elliptical cross section placed in a simple Honeycomb cladding structure. The cross-sectional area of the elliptical core is smaller than the cross-sectional area of the voids defining the vertices of the cladding structure.

In FIG. 74, a simple Honeycomb cladding structure with circular voids (80) in the cladding cells is shown for a case where the core (defect) site is formed by a void (81) with elliptical cross section. Such a design may provide a more pronounced birefringence. In FIG. 74, the cross-sectional area of the defect void (81) is larger than the cross-sectional area of the cladding forming voids (80). Another example is illustrated in FIG. 75, where a smaller void/hole (82) with elliptical cross section is placed in a simple Honeycomb cladding structure. Note that the elliptical voids have been placed centrally in the Honeycomb cells, but other placements and orientations of the elliptical major axes may also be made.

Figure 76:
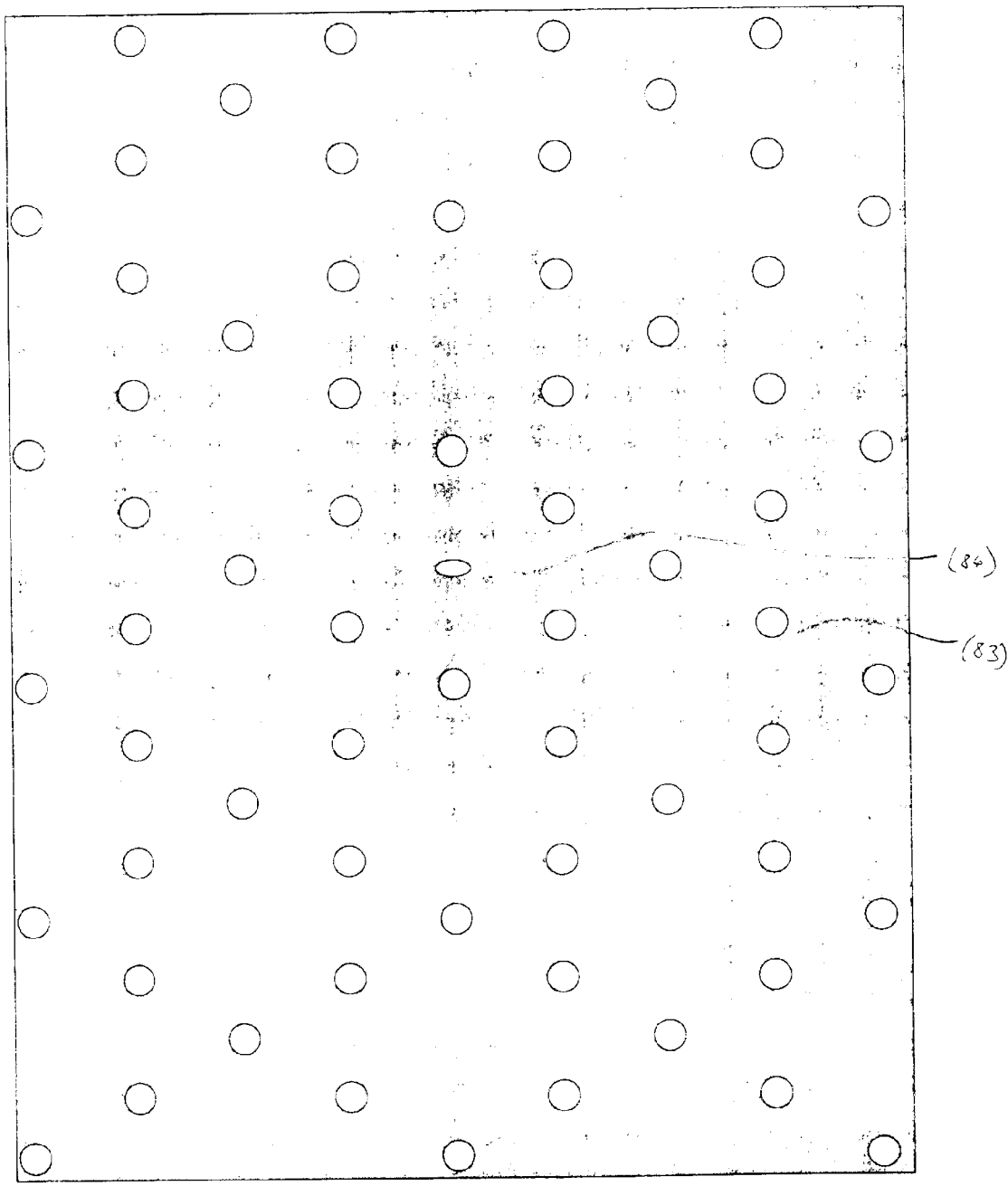
FIG. 76 illustrates an example in which an elliptical core void is placed centrally in a Kagomé cladding structure formed by circular voids. The cross-sectional area of the elliptical core is smaller than the cross-sectional area of the voids defining the vertices of the cladding structure.

FIG. 76 illustrates an example in which an elliptical core void (84) is placed centrally in a Kagomé cladding structure formed by circular voids (83). In this specific embodiment, the cross-sectional area of the defect forming void is smaller than the voids in the cladding.

Figure 77:
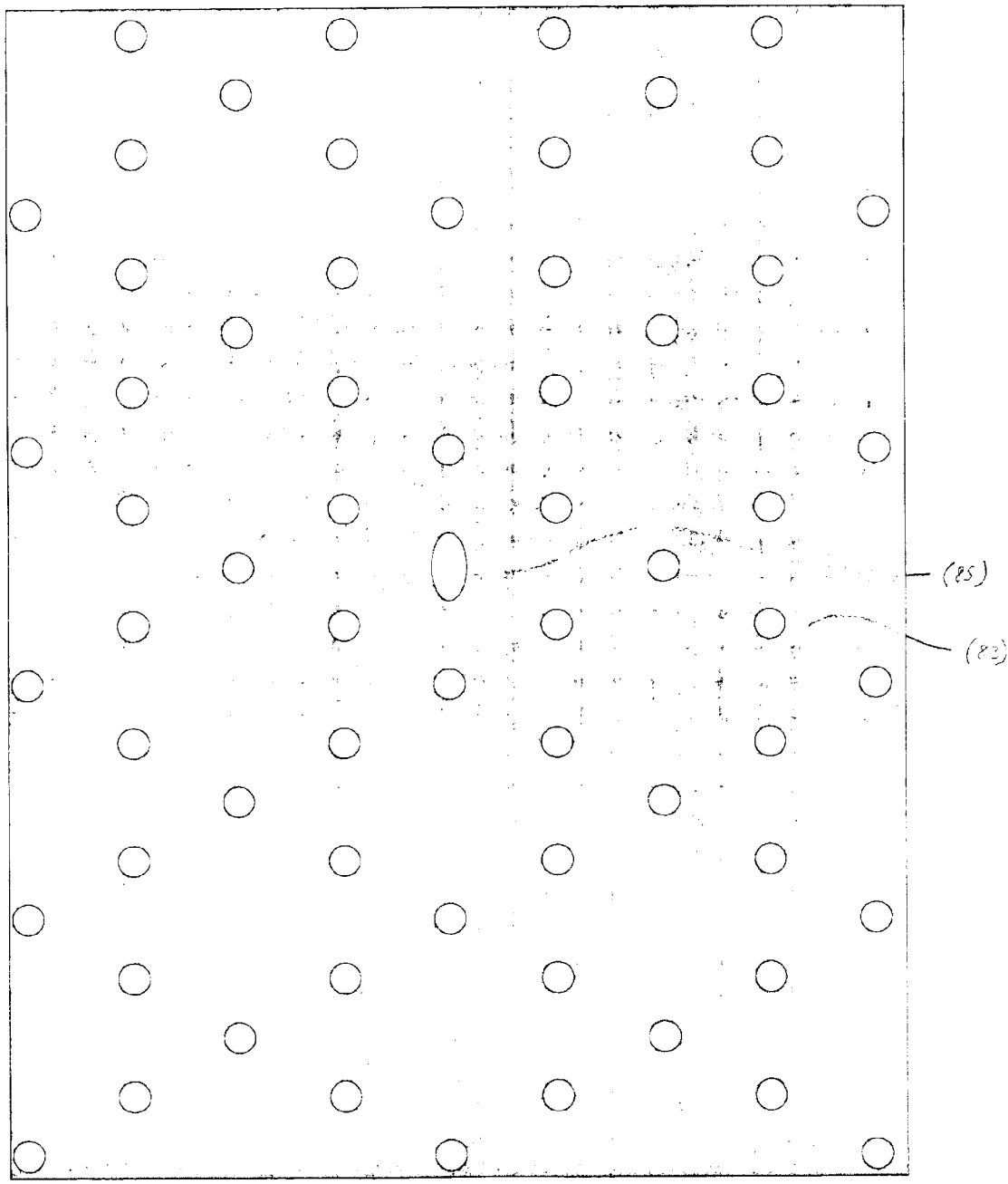
FIG. 77 shows a core region having an elliptical cross-sectional area, which is larger than the cross-sectional area of the Kagomé cladding forming voids.

Another realisation is shown in FIG. 77, only in this case the orientation of the major axes of the elliptical defect is tilted 30 degrees compared to FIG. 76, and in the case of the example of FIG. 77 the cross-sectional area is larger than the cross-sectional area of the cladding forming voids.

Figure 78:
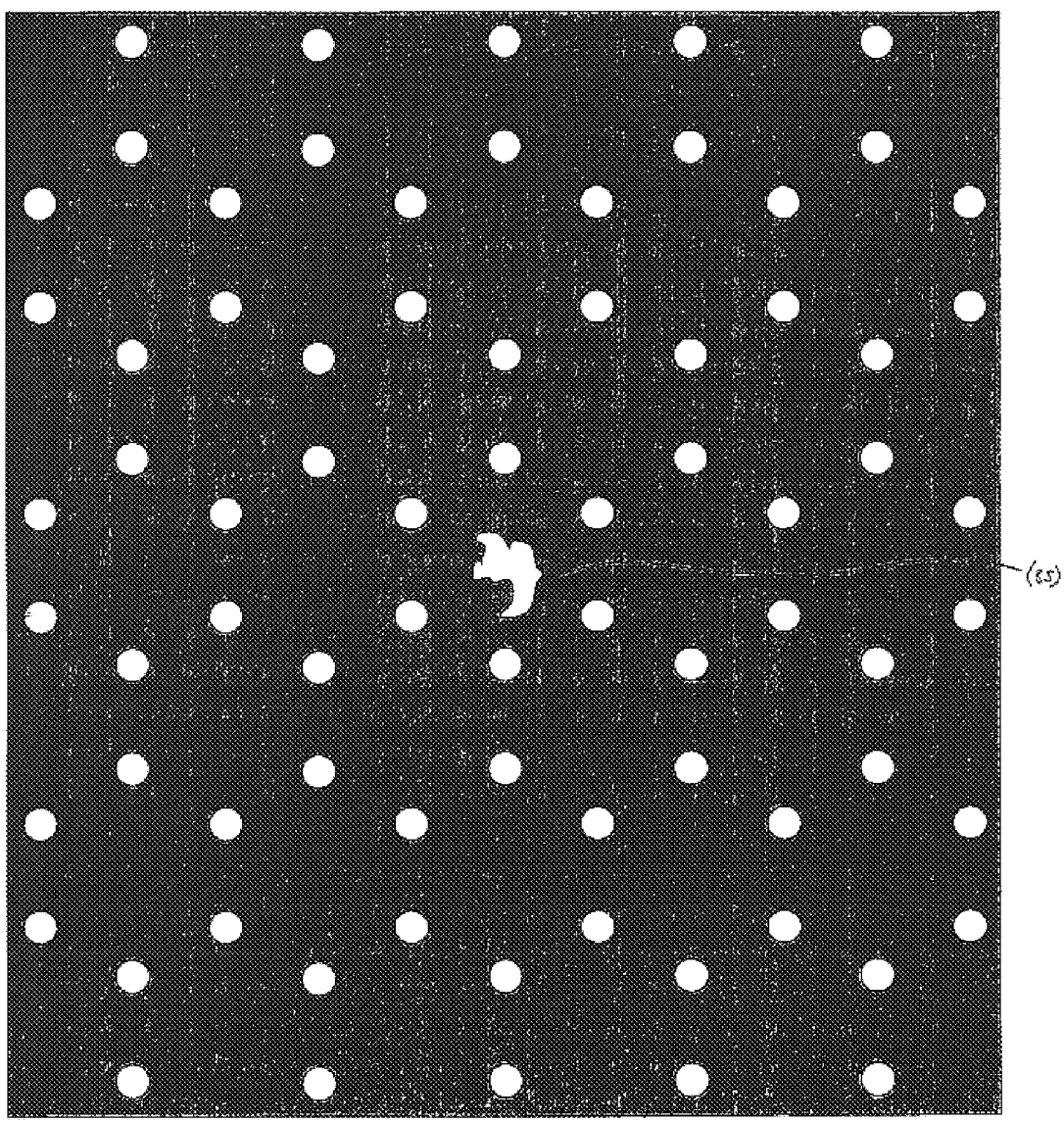
FIG. 78 shows a core defect of arbitrary cross section in a Honeycomb cladding structure.
Figure 79:
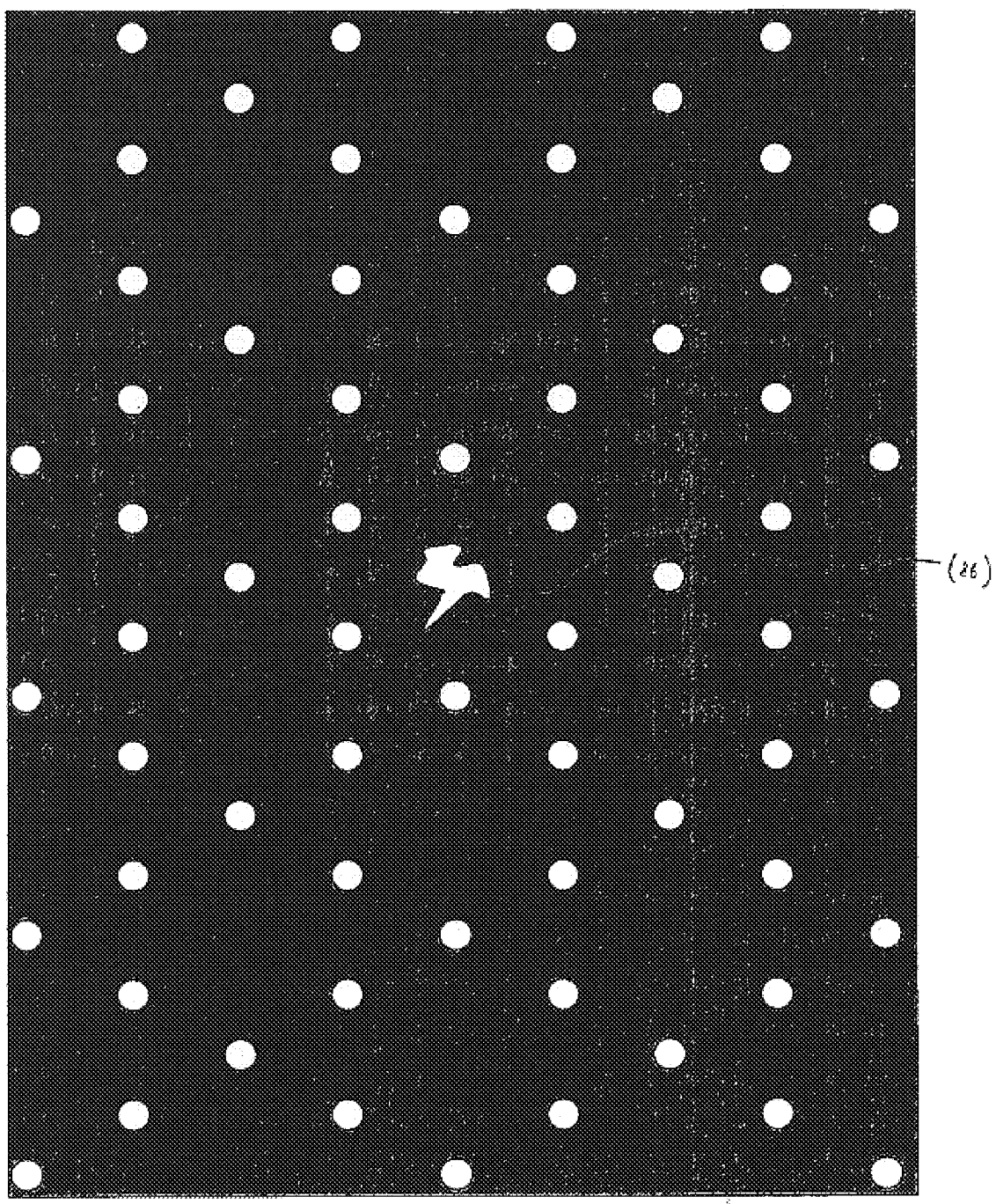
FIG. 79 shows a core defect of arbitrary cross-section in a Kagomé cladding structure.

In FIG. 78, a core defect of arbitrary cross section (85) is shown in a simple Honeycomb cladding structure, and in FIG. 79 a core defect (86) of arbitrary cross-section is shown for a Kagomé cladding structure.

Other combinations may also be considered in which the voids/holes forming the cladding structure have cross-sections different from the circular shape used in most examples.

Figure 80:
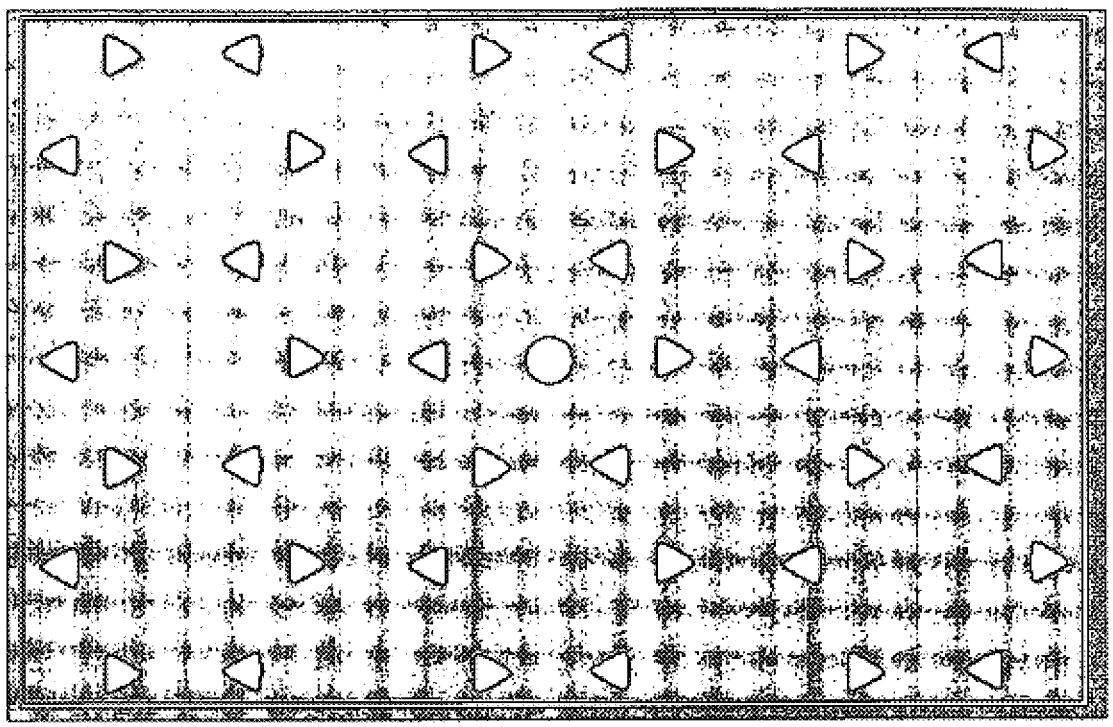
FIG. 80 shows a circular core forming defect void placed centrally in a simple Honeycomb cladding structure realised by near-triangular shaped voids.

Such an example is shown in FIG. 80 in which a circular core forming defect void (87) is placed centrally in a simple Honeycomb cladding structure realised by near-triangular shaped voids (8B). It should be noted that the orientation of the cladding forming near-triangular voids (or voids with any different cross-sectional shape) may be individually adjusted by rotation as long as the desired PBG effect of the cladding is realised. The shown orientation is an optimised configuration.

Figure 81:
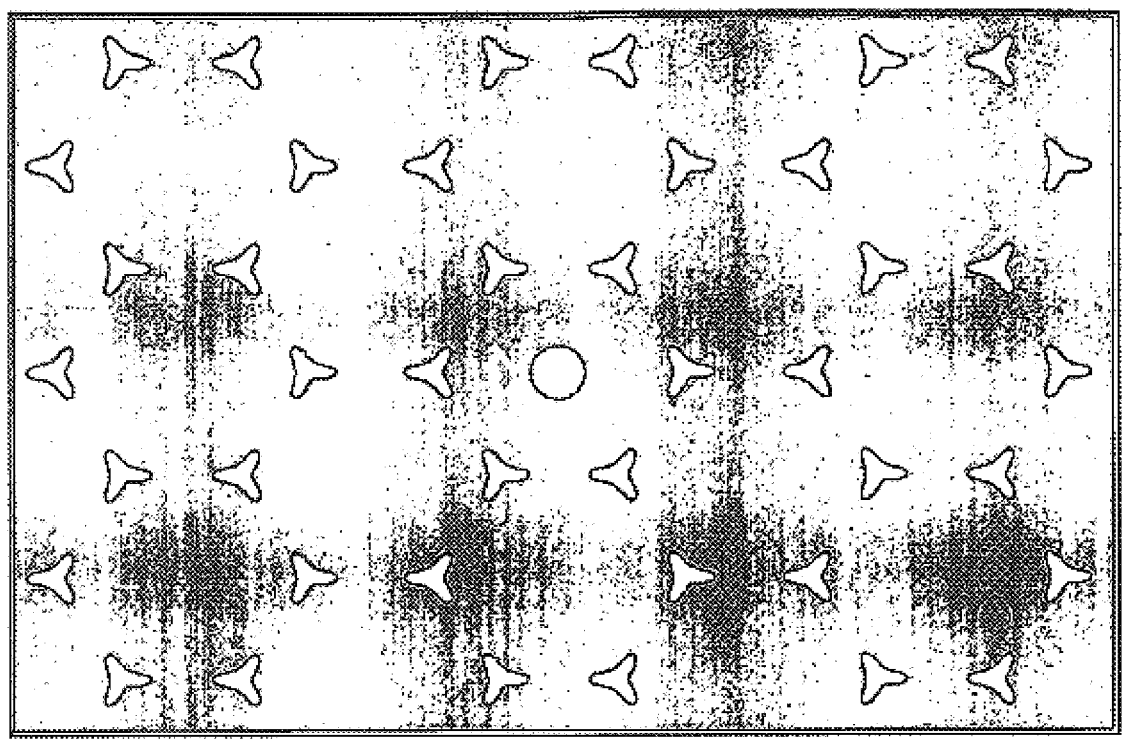
FIG. 81 shows a circular core forming defect void placed centrally in a simple Honeycomb cladding structure realised by "windmill" shaped voids.

FIG. 81 shows windmill shaped voids/holes forming the cladding in a Honeycomb structure. As in FIG. 80 it should be noted that the orientation of the cladding forming voids/holes may be individually adjusted by rotation as long as the desired PBG effect of the cladding is realised. The shown orientation is an optimised configuration.

Although the non-circular voids/holes in FIG. 80 and FIG. 81 have been illustrated for basic Honeycomb structures, non-circular voids/holes may as well be applied for defining Kagomé structures so as to adjust the PBG.

It should be noted that the combination of different cross-section shaped voids as shown in FIGS. 74–81 may be adapted to multi-core configurations as shown in FIG. 62–73.

Figure 82:
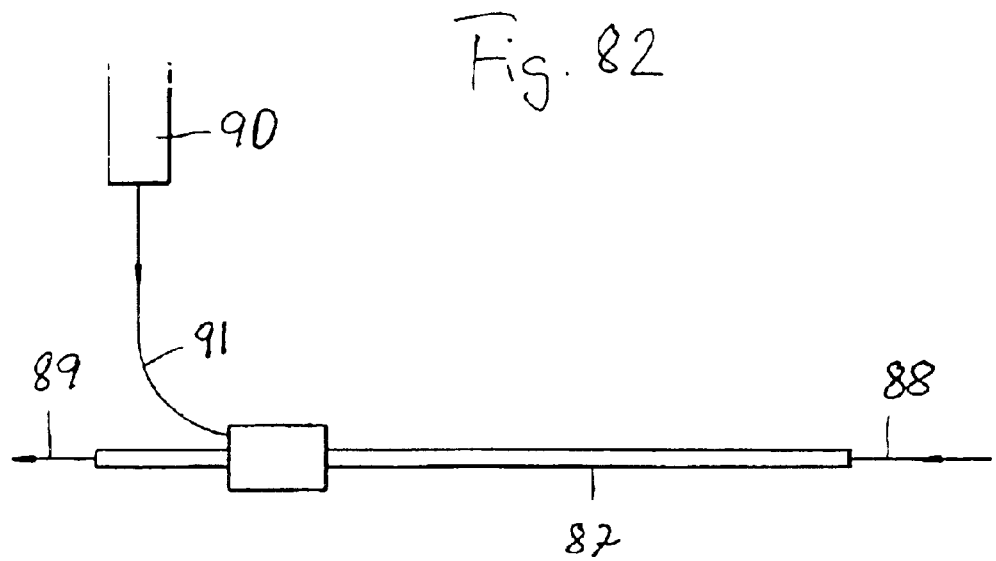
FIG. 82 shows a fibre amplifier for amplifying an optical signal using a length of the optical fibre according to the invention.

In FIG. 82 shows an example of a fibre amplifier comprising a length of the fibre according to the invention (87), an input signal which is to be amplified (88), an output signal which has been amplified (89) and a source of radiation (90) for providing a pump signal (91). The pump signal typically pumps a dopant which has been introduced into the length of fibre.

Figure 83:
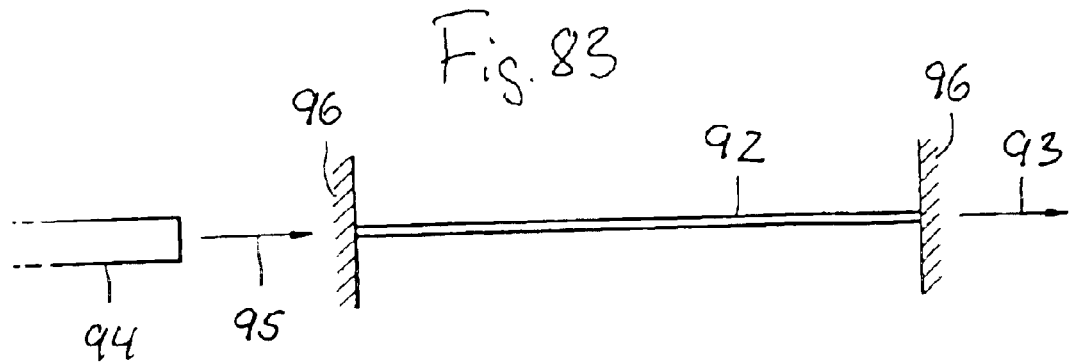
FIG. 83 shows a fibre laser for outputting an optical signal using a length of the optical fibre according to the invention.

In FIG. 83 shows an example of a fibre laser for providing laser radiation comprising a length of the fibre according to the invention (92), an output signal (93), and a source of radiation (94) for providing a pump signal (95). The fibre laser further comprises means for reflecting (96) the signal travelling inside the laser cavity.

The PBG effect, which is the fundamental element of the low-index guiding property is obtained by the periodicity of the cladding structure. However, only a very limited number of periods is necessary in order to confine the electromagnetic field, and it will, consequently, be possible to use conventional overcladding of the part of the preform that contains the periodicity.

The in case of optical fibres, this overcladding could further more improve the strength of the fibre so as to provide a fibre that is easier to splice and cleave. In a first aspect of the overcladded fibre, a circular outer fibre cross-section could be imagined, so that standard fibre fixtures may be used. However, also other overcladding tubes could be imagined, e.g., square or hexagonally shaped outer fibre cross-sections, which may be preferred in the case of highly polarisation preserving fibres, where the outer shape of the fibre could facilitate the localization of fibre primary axes etc.

As an alternative to the conventional overcladding approach, the strong mode confinement of the PBG fibres, could suggest another approach in which the fibre surrounding the core area is constructed by bundling capillary tubes into a close-packed arrangement according to the preferred design of the periodic cladding region. Outside of this periodic region, which have to be fixed in position, the outer fibre structure (corresponding to an outer cladding region) could be formed by packing of thinner glass rods, which could be mechanically shaken into place, because the key issue here not is to form a periodic structure. When the preform then later is drawn into a fibre, the outer cladding structure is melted together to form a (near) solid outer cladding. The only requirement for the outside placement of thin glass rods is that the surface tension due to an uneven distribution outside the periodic part of the fibre, do not result in a significant deformation of the periodicity.

PCF's with new functionalities may be fabricated by introducing regions within the fibres with special doping materials, or even materials that deviates significantly from the fibre basis material (e.g., glass, or polymers). These additional materials could for instance be rare-earth dopants, specially ultra-violet (UV) sensitive materials, or even semi-conductors or metals.

The fabrication process may comprise the introduction of thin rods of doped (or different) material at well-defined locations in the closely packed, periodic basis material structure. Alternatively, some of the capillary tubes could be made from a doped material, or the preform (or parts of it) could even be placed in solutions of materials that could diffuse or bind to the basis material rods and tubes. Since specific parts of the preform could be treated individually before further stacking or alternative processing would continue, this approach allows for a very high degree of flexibility.

What is claimed is:

1. An optical fibre with a waveguide structure having a longitudinal direction, said optical fibre having:
   a core region extending along the longitudinal direction,
   a cladding region extending along the longitudinal direction, said cladding region comprising an at least substantially two-dimensionally periodic structure comprising primary, elongated elements each having a centre axis extending in the longitudinal direction of the waveguide, the primary elements having a refractive index being lower than a refractive index of any material adjacent to the elongated elements,
   the periodic structure being defined, in a cross-section perpendicular to the longitudinal direction, by a unit cell, where the sum of all areas of elongated elements, which areas are comprised within the unit cell, is larger than 1.2 times the area of that primary element having its centre axis not positioned outside the unit cell and having the largest area; and
   wherein the periodic structure comprises secondary elongated elements having a refractive index being larger than that of any material adjacent thereto and to any material being adjacent to a primary element.

2. An optical fibre according to claim 1, wherein the sum of all areas of elongated elements comprised within the unit cell is larger than 1.3 times the area of that primary element having its centre axis not positioned outside the unit cell and having the largest area.

3. An optical fibre with a waveguide structure having a longitudinal direction, said optical fibre having:
  a core region extending along the longitudinal direction,
  a cladding region extending along the longitudinal direction, said cladding region comprising an at least substantially two-dimensionally periodic structure comprising primary, elongated elements each having a centre axis extending in the longitudinal direction of the waveguide, the primary elements having a refractive index being lower than a refractive index of any material adjacent to the primary elements,
the periodic structure being, in a cross-section perpendicular to the longitudinal direction, defined by a unit cell, where, in each unit cell:

$$n_d \Lambda_2 > n_{ud} \Lambda_1 (\sqrt{3})$$

where
  $n_d$ is the largest index of refraction within a first circle which is defined as a largest circle possible having a centre not positioned outside the unit cell and not enclosing any part of any primary element,
  $n_{ud}$ is a largest index of refraction not positioned outside the unit cell but outside any of the first circles of the unit cells,
  $\Lambda_1$ is a smallest distance between centre axes of two primary elements within the periodic structure,
  $\Lambda_2$ is a distance between the centre of the first circle of the unit cell and the centre of the first circle of an adjacent unit cell.

4. An optical fibre according to claim 3, wherein, for each unit cell: $n_d \Lambda_2 > 2 n_{ud} \Lambda_1$.

5. An optical fibre according to claim 3, wherein, in each unit cell, $n_d$ is at least substantially identical to $n_{ud}$.

6. An optical fibre according to claim 3, wherein, in each unit cell, $n_d > n_{ud}$.

7. An optical fibre according to claim 3, wherein $n_{ud}$ is and $n_d$ is selected within the interval of 1–10.

8. An optical fibre according to claim 3, wherein the unit cell comprises further elongated elements each having a centre axis extending in the longitudinal direction of the waveguide, the cross-sectional area of each of the further elements being less than ⅙ of a cross-sectional area of that primary element, having its centre within the unit cell, having the largest cross-sectional area.

9. An optical fibre according to claim 8, wherein:

$$n_d \Lambda_2 > (\sqrt{3}) n_{ud} \Lambda_3$$

where
  $n_d$ is the largest index of refraction within a first circle which is defined as a largest circle possible having a centre not positioned outside the unit cell and not enclosing any part of any primary element,
  $n_{ud}$ is a largest index of refraction not positioned outside the unit cell but outside any of the first circles of the unit cells,
  $\Lambda_3$ is a smallest distance between centre axes of two primary or further elements within the periodic structure,
  $\Lambda_2$ is a smallest distance between the centres of two adjacent first circles.

10. An optical fibre according to claim 9, wherein, for each unit cell: $n_d \Lambda_2 > 2 n_{ud} \Lambda_3$.

11. An optical fibre with a waveguide structure having a longitudinal direction, said optical fibre having:
  a core region extending along the longitudinal direction,
  a cladding region extending along the longitudinal direction, said cladding region comprising an at least substantially two-dimensionally periodic structure comprising primary, elongated elements each having a centre axis extending in the longitudinal direction of the waveguide, the primary elements each having a refractive index being lower than a refractive index of any material adjacent to the primary element,
the periodic structure being, in a cross-section perpendicular to the longitudinal direction, defined by a unit cell, and where a polygon is defined:
  having centres of primary elements in its vertices,
  not enclosing any centres of other primary elements than those having their centres at the vertices of the polygon, and
  having an area less than or equal to that of the unit cell, the polygon being a regular, hexagonal polygon; and
wherein the periodic structure further comprises one or more secondary elongated elements having a refractive index higher than that of any material adjacent thereto or adjacent to any primary elements, the secondary elements each has a centre axis extending in the longitudinal direction of the fibre.

12. An optical fibre according to claim 11, wherein one or more further elongated elements are provided each of which
  has an area not exceeding ⅙ of the area of that primary element having its centre within the unit cell and having the largest area,
  has a refractive index being lower than that of any material adjacent thereto,
where:
  further elements of two polygons sharing a common side are positioned symmetrically around a centre of the common side, and
  further elements of two polygons sharing a single primary element are positioned symmetrically around a centre of the single primary element.

13. An optical fibre according to claim 12, wherein the one or more further elongated elements each has an area not exceeding ⅛ of the area of that primary element having its centre within the unit cell and having the largest area.

14. An optical fibre according to claim 11, wherein, in the periodic structure, regular hexagonal polygons exist, all sides of which are shared with another regular hexagonal polygon.

15. An optical fibre according to claim 3, wherein the periodic structure further comprises one or more secondary elongated elements having a refractive index higher than that of any material adjacent thereto or adjacent to any primary elements, the secondary elements each has a centre axis extending in the longitudinal direction of the fibre.

16. An optical fibre according to claim 15, wherein, in each unit cell, a secondary element is provided having its centre axis within the first circle.

17. An optical fibre with a waveguide structure having a longitudinal direction, said optical fibre having:
  a core region extending along the longitudinal direction,
  a cladding region extending along the longitudinal direction, said cladding region comprising an at least substantially two-dimensionally periodic structure comprising primary, elongated elements each having a centre axis extending in the longitudinal direction of the waveguide, the primary elements each having a refractive index being lower than a refractive index of any material adjacent to the primary element, the periodic structure further comprising secondary, elongated elements each having a refractive index being larger than that of any material adjacent thereto and any material adjacent to a primary element, each secondary element having a centre axis extending in the longitudinal direction of the fibre.

18. An optical fibre according to claim 17, wherein the periodic structure is, in a cross-section perpendicular to the longitudinal direction, defined by at least one unit cell, where, for each unit cell, a first circle is defined as the largest circular area possible having a centre not positioned outside the unit cell and not enclosing any part of any primary elements, where a secondary element is provided having its centre axis within the first circle.

19. An optical fibre according to claim 18, wherein a plurality of first primary elements exist, parts of which exist within a distance of 1.2 or less times the radius of the first circle from the centre of the first circle, a polygon being defined as having its vertices at the centres of the plurality of first primary elements, the polygon being a regular, hexagonal polygon.

20. An optical fibre according to claim 19, wherein, in the periodic structure, hexagonal polygons exist, all sides of which are common to another hexagonal polygon.

21. An optical fibre according to claim 19, wherein the structure is defined by the hexagonal polygon and a regular triangle having a side length corresponding to that of the regular hexagonal polygon, and where hexagonal polygons exist, each side of which is common to a triangle.

22. An optical fibre according to claim 3, wherein the core region comprises a first additional elongated element extending in the longitudinal direction of the fibre.

23. An optical fibre according to claim 22, wherein the first additional element is a void.

24. An optical fibre according to claim 22, wherein the additional element or any material adjacent thereto comprises a dopant or a material showing higher order optical effects.

25. An optical fibre according to claim 22, wherein the core region comprises a second additional elongated element, the first and second additional elements being positioned at a distance where light travelling in one additional element is able to couple to the other additional element.

26. An optical fibre with a waveguide structure having a longitudinal direction, said optical fibre having:
    a core region extending along the longitudinal direction,
    a cladding region extending along the longitudinal direction, said cladding region comprising an at least substantially two-dimensionally periodic structure comprising primary, elongated elements each having a centre axis extending in the longitudinal direction of the waveguide, the primary elements each having a refractive index being lower than a refractive index of any material adjacent to the primary element,
the periodic structure being, in a cross-section perpendicular to the longitudinal direction, defined by a unit cell, and where a polygon is defined:
    having centres of primary elements in its vertices,
    not enclosing any centres of other primary elements than those having their centres at the vertices of the polygon, and
    having an area less than or equal to that of the unit cell,
the polygon being a regular, hexagonal polygon;
wherein the core region comprises a first additional elongated element extending in the longitudinal direction of the fibre.

27. An optical fibre according to claim 26, wherein the first additional element is a void.

28. An optical fibre according to claim 26, wherein the additional element or any material adjacent thereto comprises a dopant or a material showing higher order optical effects.

29. An optical fibre according to claim 26, wherein the core region comprises a second additional elongated element, the first and second additional elements being positioned at a distance where light travelling in one additional element is able to couple to the other additional element.

30. An optical fibre according to claim 17, wherein the core region comprises a first additional elongated element extending in the longitudinal direction of the fibre.

31. An optical fibre according to claim 30, wherein the first additional element is a void.

32. An optical fibre according to claim 30, wherein the additional element or any material adjacent thereto comprises a dopant or a material showing higher order optical effects.

33. An optical fibre according to claim 30, wherein the core region comprises a second additional elongated element, the first and second additional elements being positioned at a distance where light travelling in one additional element is able to couple to the other additional element.

34. An optical fibre according to claim 3, the fibre comprising a plurality of core regions.

35. An optical fibre according to claim 34, wherein the core regions are positioned symmetrically within the periodical structure, a period of the core regions being larger than a period of the periodical structure.

36. An optical fibre according to claim 26, the fibre comprising a plurality of core regions.

37. An optical fibre according to claim 36, wherein the core regions are positioned symmetrically within the periodical structure, a period of the core regions being larger than a period of the periodical structure.

38. An optical fibre according to claim 17, the fibre comprising a plurality of core regions.

39. An optical fibre according to claim 38, wherein the core regions are positioned symmetrically within the periodical structure, a period of the core regions being larger than a period of the periodical structure.

40. A sensor for sensing or detecting at least one characteristic of a liquid or gas, the sensor comprising:
    a length of the optical fibre according to claim 3, wherein the core region comprises at least a first additional element, the first element being a void extending along the longitudinal direction of the fibre,
    means for providing the liquid or gas into the void of the core region,
    means for introducing light into the core region, the light being adapted to interact with the gas or liquid in a manner so that the characteristic of the liquid or gas may be determined,
    means for detecting light emitted from the fibre and for determining the characteristic of the liquid or gas.

41. A sensor according to claim 40, wherein the introducing means are adapted to introduce the light into the first additional element.

42. A sensor according to claim 40, wherein the core region comprises a second, elongated element extending in the longitudinal direction of the fibre, where the first and second additional elements are positioned at a distance where light travelling in one additional element is able to couple to the other additional element, and wherein the introducing means are adapted to introduce the light into the second additional element.

43. A sensor for sensing or detecting at least one characteristic of a liquid or gas, the sensor comprising:
- a length of the optical fibre according to claim 11, wherein the core region comprises at least a first additional element, the first element being a void extending along the longitudinal direction of the fibre,
- means for providing the liquid or gas into the void of the core region,
- means for introducing light into the core region, the light being adapted to interact with the gas or liquid in a manner so that the characteristic of the liquid or gas may be determined,
- means for detecting light emitted from the fibre and for determining the characteristic of the liquid or gas.

44. A sensor according to claim 43, wherein the introducing means are adapted to introduce the light into the first additional element.

45. A sensor according to claim 43, wherein the core region comprises a second, elongated element extending in the longitudinal direction of the fibre, where the first and second additional elements are positioned at a distance where light travelling in one additional element is able to couple to the other additional element, and wherein the introducing means are adapted to introduce the light into the second additional element.

46. A sensor for sensing or detecting at least one characteristic of a liquid or gas, the sensor comprising:
- a length of the optical fibre according to claim 17, wherein the core region comprises at least a first additional element, the first element being a void extending along the longitudinal direction of the fibre,
- means for providing the liquid or gas into the void of the core region,
- means for introducing light into the core region, the light being adapted to interact with the gas or liquid in a manner so that the characteristic of the liquid or gas may be determined,
- means for detecting light emitted from the fibre and for determining the characteristic of the liquid or gas.

47. A sensor according to claim 46, wherein the introducing means are adapted to introduce the light into the first additional element.

48. A sensor according to claim 46, wherein the core region comprises a second, elongated element extending in the longitudinal direction of the fibre, where the first and second additional elements are positioned at a distance where light travelling in one additional element is able to couple to the other additional element, and wherein the introducing means are adapted to introduce the light into the second additional element.

49. A fibre amplifier for amplifying an optical signal, said fibre amplifier comprising:
- a length of optical fibre according to claim 3, wherein the core region comprises a dopant material along at least part of the length, and
- means for providing pump radiation to the dopant material for pumping the dopant material so as to amplify the optical signal.

50. A fibre amplifier for amplifying an optical signal, said fibre amplifier comprising:
- a length of optical fibre according to claim 11, wherein the core region comprises a dopant material along at least part of the length, and
- means for providing pump radiation to the dopant material for pumping the dopant material so as to amplify the optical signal.

51. A fibre amplifier for amplifying an optical signal, said fibre amplifier comprising:
- a length of optical fibre according to claim 17, wherein the core region comprises a dopant material along at least part of the length, and
- means for providing pump radiation to the dopant material for pumping the dopant material so as to amplify the optical signal.

52. A fibre laser for outputting laser radiation, said fibre laser comprising:
- a length of optical fibre according to claim 3, wherein the core region comprises a dopant material along at least part of the length,
- means for providing pump radiation to the dopant material for pumping the dopant material so as to amplify the optical signal, and
- feedback means for selectively feeding back at least part of the amplified optical signal so as to repeatedly pass the amplified optical signal through the length of the optical fibre so as to further amplify the optical signal.

53. A fibre laser for outputting laser radiation, said fibre laser comprising:
- a length of optical fibre according to claim 11, wherein the core region comprises a dopant material along at least part of the length,
- means for providing pump radiation to the dopant material for pumping the dopant material so as to amplify the optical signal, and
- feedback means for selectively feeding back at least part of the amplified optical signal so as to repeatedly pass the amplified optical signal through the length of the optical fibre so as to further amplify the optical signal.

54. A fibre laser for outputting laser radiation, said fibre laser comprising:
- a length of optical fibre according to claim 17, wherein the core region comprises a dopant material along at least part of the length,
- mean for providing pump radiation to the dopant material for pumping the dopant material so as to amplify the optical signal, and
- feedback means for selectively feeding back at least part of the amplified optical signal so as to repeatedly pass the amplified optical signal through the length of the optical fibre so as to further amplify the optical signal.

* * * * *